US012807680B2

(12) United States Patent
Choi et al.

(10) Patent No.: US 12,807,680 B2
(45) Date of Patent: Nov. 24, 2026

(54) HETERODIMERIC FC FUSION PROTEIN, AND COMPOSITION, USE, AND METHOD RELATED TO SAME

(71) Applicant: MEDYTOX INC., Cheongju-si (KR)

(72) Inventors: Eun Shik Choi, Yongin-si (KR); Hyun Kyu Park, Yongin-si (KR)

(73) Assignee: MEDYTOX INC., Chungcheongbuk-Do (KR)

( * ) Notice: Subject to any disclaimer, the term of this patent is extended or adjusted under 35 U.S.C. 154(b) by 757 days.

(21) Appl. No.: 18/102,438

(22) PCT Filed: Jul. 28, 2021

(86) PCT No.: PCT/KR2021/009835
§ 371 (c)(1),
(2) Date: Jan. 27, 2023

(87) PCT Pub. No.: WO2022/025643
PCT Pub. Date: Feb. 3, 2022

(65) Prior Publication Data

US 2024/0254196 A1 Aug. 1, 2024

(30) Foreign Application Priority Data

Jul. 29, 2020 (KR) ........................ 10-2020-0094232

(51) Int. Cl.

| | |
|---|---|
| ***C07K 14/705*** | (2006.01) |
| ***C07K 14/475*** | (2006.01) |
| ***C07K 14/71*** | (2006.01) |
| ***C07K 14/715*** | (2006.01) |
| ***C07K 19/00*** | (2006.01) |

(52) U.S. Cl.
CPC ........ *C07K 14/7155* (2013.01); *C07K 14/475* (2013.01); *C07K 14/705* (2013.01); *C07K 14/71* (2013.01); *C07K 19/00* (2013.01); *C07K 2317/52* (2013.01); *C07K 2317/53* (2013.01); *C07K 2317/64* (2013.01); *C07K 2319/00* (2013.01); *C07K 2319/30* (2013.01); *C07K 2319/32* (2013.01)

(58) Field of Classification Search
CPC .. C07K 14/705; C07K 19/00; C07K 2319/00; C07K 2319/30; C07K 2319/32; C07K 14/715
See application file for complete search history.

(56) References Cited

U.S. PATENT DOCUMENTS

| | | | | |
|---|---|---|---|---|
| 7,666,622 | B2 | 2/2010 | Sharma et al. | |
| 2002/0012962 | A1* | 1/2002 | Stahl | A61P 35/00 435/325 |
| 2008/0292590 | A1* | 11/2008 | Becher | C07K 14/7155 530/350 |
| 2016/0175458 | A1* | 6/2016 | Alvarez | A61P 7/04 435/219 |
| 2016/0264685 | A1 | 9/2016 | Fouque et al. | |
| 2018/0289825 | A1 | 10/2018 | Alvarez et al. | |
| 2019/0077881 | A1 | 3/2019 | Ast et al. | |
| 2021/0171608 | A1 | 6/2021 | Moore et al. | |

FOREIGN PATENT DOCUMENTS

| | | | |
|---|---|---|---|
| JP | 2014530848 | A | 11/2014 |
| JP | 2018500328 | A | 1/2018 |
| JP | 2019512272 | A | 5/2019 |
| KR | 1020150092367 | A | 8/2015 |
| KR | 1020150129685 | A | 11/2015 |
| KR | 1020160048028 | A | 5/2016 |
| WO | 2013088259 | A2 | 6/2013 |
| WO | 2014126582 | A1 | 8/2014 |
| WO | 2016100788 | A1 | 6/2016 |
| WO | 2016146594 | A1 | 9/2016 |
| WO | 2017165464 | A1 | 9/2017 |

OTHER PUBLICATIONS

Bhattacharya et al. Impact of genetic variation on three dimensional structure and function of proteins. PLoS ONE 12(3): e0171355, 2017.*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Doerks et al. Protein annotation: detective work for function prediction. Trends in Genetics 14:248-250, 1998.*
Fenton et al. Rheostat positions: a new classification of protein positions relevant to pharmacogenomics. Medicinal Chem Res 29: 1133-1146, 2020.*
Guo et al. Protein tolerance to random amino acid change. Proc Natl Acad Sci USA 101(25): 9205-9210, 2004.*
Ha et al. Immunoglobulin Fc heterodimer platform technology: from design to applications in therapeutic antibodies and proteins. Front Immunol 7: 394, 2016 (16 total pages).*
Skolnick et al. From genes to protein structure and function: novel applications of computational approaches in the genomic era. Trends Biotechnol 18(I):34-39 2000.*
Smith et al. The challenges of genome sequence annotation or "the devil is in the details". Nature Biotechnol 15: 1222-1223, 1997.*
Tokuriki et al. Stability effects of mutations and protein evolvability. Curr Opin Structural Biol 19: 596-604, 2009.*

(Continued)

*Primary Examiner* — Bridget E Bunner
(74) *Attorney, Agent, or Firm* — CANTOR COLBURN LLP

(57) ABSTRACT

Provided are heterodimeric Fc fusion proteins that are not only fast, simple, and efficient to purify, but also exhibit desirable therapeutic properties, such as increased FcRn binding capacity or increased FcγR binding capacity, and compositions, uses, methods related thereto.

19 Claims, 65 Drawing Sheets

Specification includes a Sequence Listing.

(56) References Cited

OTHER PUBLICATIONS

Weidle et al. Genetically Engineered Fusion Proteins for Treatment of Cancer. Cancer Genomics Prot 9: 357-372, 2012.*
Fischer et al., "Exploiting light chains form the scalable generation and platform purification of native human bispecific IgG", Nature Communications, 2015, p. 1-12, 6: 6113 DOI: 10.1038/ncomms7113.
1st Office Action issued dated Mar. 19, 2024 of Japanese Patent Application No. 2023-506124.
Extended European Search Report issued Jul. 11, 2024 of European Patent Application No. 21848914.4.

* cited by examiner

| | SAMPLE NAME | RETENTION TIME (MINUTE) | HEIGHT (μV) | AREA | AREA(%) |
|---|---|---|---|---|---|
| 1 | IL1T | 5.470 | 638 | 8052 | 0.42 |
| 2 | IL1T | 6.344 | 2670 | 99416 | 5.20 |
| 3 | IL1T | 7.142 | 66205 | 1583687 | 82.88 |
| 4 | IL1T | 7.893 | 6255 | 219555 | 11.49 |

| | SAMPLE NAME | RETENTION TIME (MINUTE) | HEIGHT (μV) | AREA | AREA(%) |
|---|---|---|---|---|---|
| 1 | PET101 | 5.314 | 921 | 12516 | 0.75 |
| 2 | PET101 | 6.037 | 3106 | 66196 | 3.99 |
| 3 | PET101 | 6.836 | 71741 | 1453080 | 87.57 |
| 4 | PET101 | 7.757 | 5742 | 127513 | 7.68 |

| | SAMPLE NAME | RETENTION TIME (MINUTE) | HEIGHT (μV) | AREA | AREA(%) |
|---|---|---|---|---|---|
| 1 | PET101 | 6.040 | 538 | 10409 | 0.69 |
| 2 | PET101 | 6.838 | 79681 | 1492460 | 99.31 |

Chromatogram Results

| | SAMPLE NAME | RETENTION TIME (MINUTE) | HEIGHT (µV) | AREA | AREA(%) |
|---|---|---|---|---|---|
| 1 | PET101 knob κκ | 5.515 | 53297 | 1567949 | 100.00 |
| 2 | PET101 | 5.521 | 1009 | 26786 | 1.98 |
| 3 | PET101 | 7.840 | 1324830 | 1324830 | 98.02 |
| 4 | PET101 hole λλ | 10.694 | 912588 | 912588 | 100.00 |

● PET101 (EC50 = 44 pM)
○ Rilonacept (EC50 = 37 pM)
□ Canakinumab (EC50 = 2678 pM)

118T3v01: 250 kDa
hIL-1β: 18.4kDa
hIL-18: 18.4kDa
118T3v01:hIL-18:hIL-1β = 1.00:1.03:1.06

M: Marker
1: MabSelect PRIMARY PURIFIED ELUATE
2: KappaSelect SECONDARY PURIFIED ELUATE
3: LambdaFabSelect TERTIARY PURIFIED ELUATE

HETERODIMERIC FC FUSION PROTEIN, AND COMPOSITION, USE, AND METHOD RELATED TO SAME

CROSS-REFERENCE TO RELATED APPLICATIONS

This application is a U.S. National Stage Application of PCT/KR2021/009835, filed on Jul. 28, 2021, and claims priority to Korean Patent Application No. 10-2020-0094232, filed on Jul. 29, 2020, and all the benefits accruing therefrom under 35 U.S.C. § 119, the content of which in its entirety is herein incorporated by reference.

INCORPORATION OF ELECTRONICALLY-FILED MATERIAL

The Instant Application contains a Sequence Listing which has been submitted electronically under WIPO Standard ST.25 in ASCII TXT format and is hereby incorporated by reference in its entirety. Said ASCII TXT copy, created on Sep. 1, 2026, is named "GN-65379-US_Amended_ST25_260901" and is 76,413 bytes in size.

TECHNICAL FIELD

The present disclosure relates to Fc fusion technology, and more specifically, to heterodimeric Fc fusion proteins and related compositions, uses, and methods thereof.

BACKGROUND ART

Immunoglobulin Fc Fusion Technology

Fc fusion technology, which binds a protein of interest to an Fc residue of human immunoglobulin (typically an IgG), is a useful tool for improving the therapeutic properties of biologically active proteins. A fusion protein in which an Fc region is bound to a target protein has extended half-life in blood due to reducing endosomal degradation by binding to a neonatal Fc receptor (FcRn). In addition, the Fc region may increase the immune effector function of the fusion protein by mediating responses of Fcγ receptors to immune cells.

The Fc region of naturally occurring IgGs tends to form homodimers. Therefore, the simplest method of developing a therapeutic protein based on Fc fusion technology is binding a biologically active target protein (that is, a ligand, an extracellular domain receptor, or a cytokine) to the Fc region and expressing it in an appropriate host cell to produce homodimeric Fc proteins, which may be easily isolated by using an affinity reagent specific for the IgG Fc.

In some situations, heterodimeric Fc fusion is required. Many proteins, including cytokines and their receptors, naturally exist and function as heterodimers, and some proteins exhibit increased pharmacological properties when produced as heterodimers with partner proteins which are chosen for therapeutic purposes.

Knob-into-hole mutagenesis technology for constructing an asymmetric bi-specific antibody in the form of a human IgG1 generates many by-products such as knob-knob and hole-hole homodimers and monomers. Purification for removing these by-products and securing heterodimers requires a complicated process. In particular, when physicochemical properties of a heterodimer are similar to that of a homodimer and a monomer, it is very difficult to separate and purify the heterodimers to a level suitable for using as therapeutic agents for humans. Strategies known to overcome this include, in the case of an antibody, antibody variable region engineering, which makes the physicochemical properties of a heterodimer to be distinguished from that of a homodimer and a monomer, and a method of purely separating heterodimers by using specific resins for kappa light chains and lambda light chains, by constituting the light chain regions of a heterodimer with a kappa light chain and a lambda light chain, respectively (for example: International Publication No. WO2016-146594). However, unlike antibodies, in the case of a heterodimeric Fc fusion protein in which two different proteins present in nature are asymmetrically bound to Fc, there are many limitations in protein sequence engineering for heterodimer separation.

Interleukin-1 (IL-1)

Interleukin-1 (IL-1) is a potent pro-inflammatory cytokine produced by a variety of cell types, including mononuclear phagocytes, in infection and inflammatory responses. The IL-1 family consists of seven agonists, including IL-1α and IL-1β, and three naturally occurring receptor antagonists, including an IL-1 receptor antagonist (IL-1Ra). Two IL-1 receptors, IL-1R type I, and IL-1R type II were identified. These two receptors are capable of interacting with all three types of IL-1 family molecules. Although IL-1RI mediates IL-1-induced cellular activity, an IL-1/IL-1RI complex is unable to transduce a signal by itself, and is dependent on involvement of a second receptor chain, an IL-1R accessory protein (IL1RAP). In addition to IL1-signaling, IL1RAcP plays a critical role in mediating effects of IL33 through an ST2/IL1RAP complex, and mediating effects of IL36 through an IL1Rrp2/IL1RAP complex. IL-1 is known to be involved in various diseases including joint, bone and muscle diseases such as rheumatoid arthritis and osteoarthritis; hereditary systemic auto-inflammatory diseases such as familial Mediterranean fever; systemic auto-inflammatory diseases such as systemic juvenile idiopathic arthritis, and adult-type Still's disease; common inflammatory diseases such as gout and type 2 diabetes; acute onset ischemic diseases such as myocardial infarction; and cancer. Many therapies for blocking IL-1 activity have been approved and are under development. IL-1 targeting began in 1993 with the introduction of anakinra (Kineret; Amgen). Anakinra is a recombinant form of a natural IL-1 receptor antagonist (IL-1Ra), and blocks activity of both IL-1α and IL-1β. Neutralizing IL-1 with antibodies or soluble receptors has also been shown to be effective, and a soluble decoy rilonacept (Arcalyst; Regeneron) and an anti-IL-1β neutralizing monoclonal antibody canakinumab (Ilaris; Novartis) have been approved. In addition, International Publication No. WO 2014/126582 discloses a heterodimeric protein including extracellular regions of human IL-1R1 and human IL-1RAcP, wherein the IL-1R1 region and the IL-1RAcP region are each fused to a different mutant of a Fc region of a human IgG1.

Inflammasome

Inflammasome is an intracellular protein complex that promotes secretion of IL-1β and IL-18 in response to pathogens or cell damage and induces pyroptosis. Secretion of IL-1β and IL-18 by inflammasomes mainly occurs in myeloid cells, and when pyroptosis is induced, secretion of alarmin proteins, IL-1α and high mobility group box 1 (HMGB1), through gasdermin pores is also stimulated. Although normal inflammasome plays an important role in innate immunity, abnormal activity of inflammasome acts as a cause of various diseases such as inflammatory diseases, neurodegenerative diseases, and cancer. Treatment strategies for diseases related to inflammasome activity include 1) inhibition of inflammasome sensor proteins such as Nlrp3, 2) inhibition of caspase, an enzyme mediating gasdermin pore formation and cytokine secretion, and 3) inhibition of effector proteins. In particular, since effector protein inhibition is capable of controlling the inflammatory response by inflammasome regardless of the upstream signaling pathway, effector protein inhibition may be expected to be efficient in various related diseases.

Transforming Growth Factor β (TGF-β)

In human tumors, not only cancer cells but also immune cells such as cytotoxic T cells and natural killer cells that inhibit tumor growth are observed, and in addition, regulatory T cells (Treg), and myeloid-derived suppressor cells (MDSC), which are immunosuppressive cells that promote tumor growth are observed. MDSC is generated by abnormal differentiation of myeloid cells due to chronic inflammation, and pro-inflammatory cytokines such as IL-1 and IL-6 that cause chronic inflammation, and chemokines play a key role in the generation and intratumoral infiltration of MDSC. Distribution and activity of immune cells and immunosuppressive cells within a tumor is called tumor immune microenvironment (TIME), and is known to significantly contribute to a response to immune-anticancer drugs such as PD-1 antibodies. MDSC and Treg, major immunosuppressive cells in tumors, are known to decrease functions of cytotoxic T cells and natural killer cells through various mechanisms. In particular, transforming growth factor β (TGF-β), which is secreted from these immunosuppressive cells and cancer cells has been shown to play a key role in immunosuppression. Recently, it has been reported that inhibition of TGF-β in mice and humans significantly improves the response to immune-anticancer drugs. However, as TGF-β is an anti-inflammatory cytokine, TGF-β1 deficiency causes severe inflammatory diseases in mice, and inhibition of the TGF-β signaling pathway in cancer cells has been reported to increase intratumoral infiltration of MDSC. The transforming growth factor beta (TGF-β) receptor family consists of TGF-βRI, TGF-βRII, and TGF-βRIII, and in particular, TGF-βRII is known to bind to TGF-β1 and TGF-β3 with high affinity, and to bind to TGF-β2 with a relatively low binding capacity.

DESCRIPTION OF EMBODIMENTS

Technical Problem

An object of the present disclosure is to provide heterodimeric Fc fusion proteins that are not only fast, simple, and efficient to purify, but also exhibit desirable therapeutic properties, such as increased FcRn binding capacity or increased FcγR binding capacity.

Another object of the present disclosure is to provide compositions related to the heterodimeric Fc fusion proteins.

Still another object of the present disclosure is to provide uses related to the heterodimeric Fc fusion proteins.

Still another object of the present disclosure is to provide methods related to the heterodimeric Fc fusion proteins.

Solution to Problem

The first aspect of the present disclosure provides a heterodimeric Fc fusion protein, including:

i) a first polypeptide including a first target protein, a first linker, and a first Fc region of an immunoglobulin, in the N-terminus to C-terminus direction; and ii) a second polypeptide including a second target protein, a second linker, and a second Fc region of an immunoglobulin in the N-terminus to C-terminus direction, wherein the first target protein and the second target protein are different proteins from each other, and the first linker and the second linker are a κ light chain constant region ($C_L κ$) or a variant thereof, and a λ light chain constant region ($C_L λ$) or a variant thereof, respectively.

The second aspect of the present disclosure provides a pharmaceutical composition including the heterodimeric Fc fusion protein as an active ingredient, and a pharmaceutically acceptable carrier.

The third aspect of the present disclosure provides a composition for use as a linker between a target protein and an Fc region, including a κ light chain constant region ($C_{Lκ}$) or a variant thereof, and a λ light chain constant region ($C_{Lλ}$) or a variant thereof, in the heterodimeric Fc fusion proteins including the target protein and the immunoglobulin Fc region.

The fourth aspect of the present disclosure provides a use of the κ light chain constant region ($C_{Lκ}$) or a variant thereof, and the λ light chain constant region ($C_{Lλ}$) or a variant thereof, as linkers between a target protein and an Fc region, in the heterodimeric Fc fusion proteins including the target protein and the immunoglobulin Fc region.

The fifth aspect of the present disclosure provides a method of using the κ light chain constant region ($C_{Lκ}$) or a variant thereof, and the λ light chain constant region ($C_{Lλ}$) or a variant thereof, in the heterodimeric Fc fusion proteins as linkers between a target protein and an Fc region, in the heterodimeric Fc fusion proteins including the target protein and the immunoglobulin Fc region.

The sixth aspect of the present disclosure provides a method of preparing the heterodimeric Fc fusion proteins, including introducing each of the κ light chain constant region ($C_{Lκ}$) or a variant thereof, and the λ light chain constant region ($C_{Lλ}$) or a variant thereof, as linkers between a target protein and an Fc region.

The seventh aspect of the present disclosure provides a method of purifying the heterodimeric Fc fusion proteins, including purifying the heterodimeric Fc fusion proteins based on affinity of the κ light chain constant region ($C_{Lκ}$) and the λ light chain constant region ($C_{Lλ}$).

The eighth aspect of the present disclosure provides a method of increasing FcRn binding capacity of the heterodimeric Fc fusion proteins, including introducing each of the κ light chain constant region ($C_{Lκ}$) or a variant thereof, and the λ light chain constant region ($C_{Lλ}$) or a variant thereof, as linkers between a target protein and an Fc region.

The ninth aspect of the present disclosure provides a method of increasing half-life of the heterodimeric Fc fusion proteins, including introducing each of the κ light chain constant region ($C_{Lκ}$) or a variant thereof, and the λ light chain constant region ($C_{Lλ}$) or a variant thereof, as linkers between a target protein and an Fc region.

The tenth aspect of the present disclosure provides a method of increasing FcγR binding capacity of the heterodimeric Fc fusion proteins, including introducing each of the κ light chain constant region ($C_{Lκ}$) or a variant thereof, and the λ light chain constant region ($C_{Lλ}$) or a variant thereof, as linkers between a target protein and an Fc region.

The eleventh aspect of the present disclosure provides a method of increasing antibody-dependent cell-mediated cytotoxicity (ADCC) of the heterodimeric Fc fusion proteins, including introducing each of the κ light chain constant region ($C_{Lκ}$) or a variant thereof, and the λ light chain constant region ($C_{L\lambda}$) or a variant thereof, as linkers between a target protein and an Fc region.

Advantagea-ous Effects of Disclosure

According to the present disclosure, heterodimeric Fc fusion proteins, that are not only fast, simple and efficient to purify, but also exhibit desirable therapeutic properties, such as increased FcRn binding capacity or increased FcγR binding capacity, and compositions, uses, methods related thereto are provided.

BRIEF DESCRIPTION OF DRAWINGS

FIGS. 7K, 7L, 7M, 7N, and 7O show results of analyzing binding capacity of canakinumab to human IL-1α, human IL-1β, monkey IL-1β, mouse IL-1α, and mouse IL-1β, respectively by using surface plasmon resonance (SPR).

BEST MODE

Definition

Figure 1:
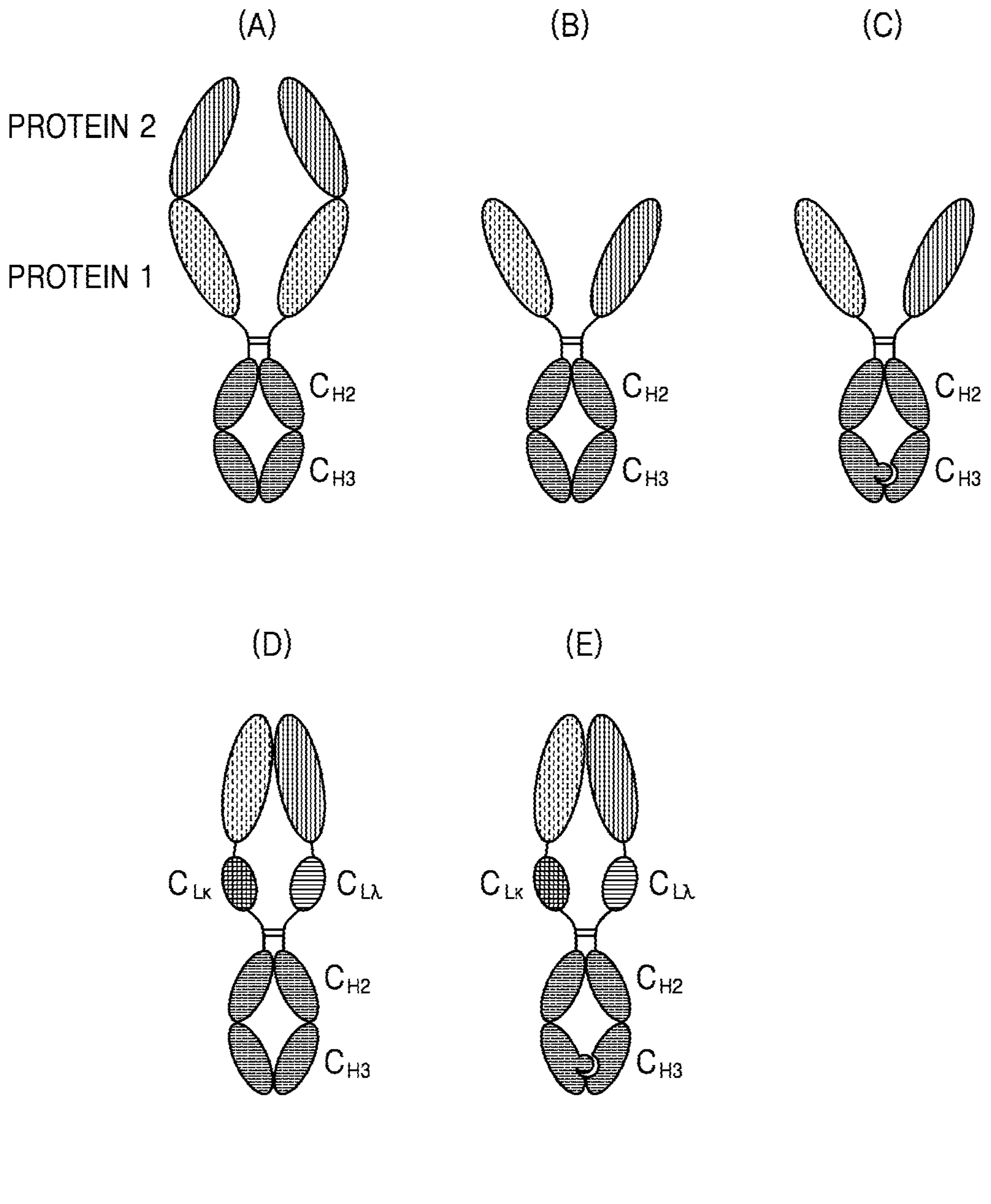
FIGS. 1A-1E show a schematic diagram of a method of preparing an Fc fusion protein in which two different proteins are bound.

Unless otherwise defined, technical or scientific terms used herein have the same meanings as generally understood in the art to which the present disclosure belongs. The following definitions will be applied for understanding of the disclosure, the singular of a term used herein includes the plural, and vice versa.

The terms 'polypeptide' and 'protein', used herein, may be used interchangeably to refer to a long chain peptide having an amino acid sequence of a natural protein or an amino acid sequence having one or more mutations, such as deletions, substitutions, additions, and/or insertions, in one or more amino acid residues.

The term 'fusion protein' refers to a protein having two or more moieties covalently linked together, wherein each moiety is derived from a different protein.

The terms 'Fc', 'Fc region', and 'Fc region' refer to a region consisting of a hinge region or a part thereof, and CH2 and CH3 regions of an antibody molecule. The Fc region of the IgG class refers to, for example, a region from the 226th cysteine to the C terminus, or a region from the 230th proline to the C terminus, by EU numbering (also called EU INDEX), but is not limited thereto. An Fc moiety may be appropriately obtained by partially digesting IgG1, IgG2, IgG3, or IgG4 monoclonal antibodies with a proteolytic enzyme such as pepsin or papain, and then re-eluting the fraction adsorbed to the Protein A column or Protein G column.

The term 'heterodimer' refers to a polypeptide composed of two polypeptides having different amino acid sequences.

The term 'linker' refers to a nucleic acid, amino acid, or non-peptide moiety that may be inserted between one or more molecules, for example, one or more component regions. For example, a linker may be used to provide a desired site of interest between components to facilitate manipulation. A linker may also be provided to enhance expression of a fusion protein from the host cell, and reduce steric hindrance so that the components can assume their optimal tertiary structure and/or interact properly with the target molecule. A linker sequence may include one or more amino acids naturally linked to the receptor component, or may be a sequence added to enhance expression of a fusion protein, to provide a desired site of interest, to allow the component region to form an optimal tertiary structure, and/or to enhance interaction of the component with its target molecule. Preferably, a linker increases flexibility of components of a fusion protein without interfering with the structure of each functional component in the fusion protein.

Heterodimeric Fc Fusion Proteins

An aspect of the present disclosure provides a heterodimeric Fc fusion protein, including:

i) a first polypeptide including a first target protein, a first linker, and a first Fc region of an immunoglobulin, in the N-terminus to C-terminus direction; and ii) a second polypeptide including a second target protein, a second linker, and a second Fc region of an immunoglobulin in the N-terminus to C-terminus direction, wherein the first target protein and the second target protein are different proteins from each other, and the first linker and the second linker are a κ light chain constant region ($C_{L\kappa}$) or a variant thereof, and a λ light chain constant region ($C_{L\lambda}$) or a variant thereof, respectively.

In order to overcome difficulties in purification of heterodimeric Fc fusion proteins, the present inventors devised κλ Fc fusion protein technology, in which an antibody κ light chain constant region ($C_{L\kappa}$) and an λ light chain constant region ($C_{L\lambda}$) are introduced between the C-terminus of two different target proteins and the N-terminus of a hinge region of the Fc region, respectively. The κλ Fc fusion protein technology according to the present disclosure makes it possible to quickly and simply isolate heterodimeric Fc fusion proteins with high purity, by utilizing commercially produced $C_{L\kappa}$-specific resins and $C_{L\lambda}$-specific resins.

Since the $C_{L\kappa}$ and $C_{L\lambda}$ regions each have a molecular weight of about 12.5 kDa, an increase in the molecular weight of the Fc fusion protein due to the introduction of $C_{L\kappa}$ and $C_{L\lambda}$ regions is expected to be about 25 kDa. The κλ Fc fusion protein technology according to the present disclosure may improve convenience and efficiency of separation and purification of heterodimers, without causing significant changes in molecular weight, stability, and safety of the fusion proteins.

In an embodiment, the $C_{L\lambda}$ mutant may have a serine (Ser) at the C-terminus deleted. Specifically, the C-terminus serine (Ser) may be at position 215 based on Kabat numbering.

In an embodiment, the $C_{L\kappa}$ variant and/or the $C_{L\lambda}$ variant may be one in which cysteine (Cys), which forms a disulfide bond with the heavy chain constant region CH1, is substituted with serine (Ser), alanine (Ala), or valine (Val). Specifically, the cysteine (Cys) forming a disulfide bond with the heavy chain constant region CH1 may be at position 214, based on Kabat numbering.

In FIG. 1, A is an inline homodimeric Fc fusion protein, in which a polypeptide linking two different proteins (proteins 1 and 2) with a single chain is bound to the N-terminus of the hinge region of the Fc region of human immunoglobulin G (IgG); B is a heterodimeric Fc fusion protein, in which two different proteins are each linked to the N-terminus of the hinge region of the IgG Fc region; C is a knob-into-hole heterodimeric Fc fusion protein (KiH heterodimeric Fc fusion protein), in which a mutation promoting heterodimer formation is introduced in the CH3 region of IgG Fc; D is a κλ heterodimeric Fc fusion protein, in which two different proteins are respectively linked by a single chain to a human immunoglobulin kappa light chain constant region ($C_{L\kappa}$) and lambda light chain constant region ($C_{L\lambda}$), and then, bound to the N-terminus of the hinge region of the Fc region; and E is a knob-into-hole κλ heterodimeric Fc fusion protein (KiH κλ-Fc fusion protein), in which a mutation promoting heterodimer formation is introduced in the CH3 region of Fc. In FIGS. 1, A, B and C correspond to the related art, and D and E, particularly E, fall within the scope of the present disclosure.

In an embodiment, the heterodimeric Fc fusion protein may further include a third target protein at one or more of the C-terminus of the first polypeptide, and the C-terminus of the second polypeptide.

In an embodiment, the heterodimeric Fc fusion protein may have mono-specificity or multi-specificity. The term 'mono-specificity' means being capable of specifically binding to one target, and 'multi-specificity' means being capable of specifically binding to two or more distinct targets. For example, a fusion protein has bi-specificity, including a region specifically binding to a first target and a region specifically binding to a second target.

In an embodiment, the target protein may be a ligand, a receptor, a cytokine, an enzyme, or a peptide. In an embodiment, the receptor may be a cytokine receptor. In an embodiment, the cytokine and/or receptor may be one that naturally exists and functions as a heterodimer, for example, may be at least one selected from the group consisting of Interleukin-1 (IL1), Interleukin-2 (IL2), Interleukin-3 (IL3), Interleukin-4 (IL4), Interleukin-5 (IL5), Interleukin-6 (IL6), Interleukin-11 (IL11), Interleukin-13 (IL13), interleukin-15 (IL15), interleukin-18 (IL18), interleukin-23 (IL23), interleukin-31 (IL31), interleukin-33 (IL33), interleukin-35 (IL35), interleukin-36 (IL36), leukemia inhibitory factor (LIF), oncostatin M (OSM), granulocyte macrophage colony stimulating factor (GM-CSF), gamma-interferon (IFN-γ), thymic stromal lymphopoietin (TSLP), transforming growth factor-beta (TGF-β), vascular endothelial growth factor (VEGF), and tumor necrosis factor-alpha (TNF-α), but is not limited thereto.

Figure 2:
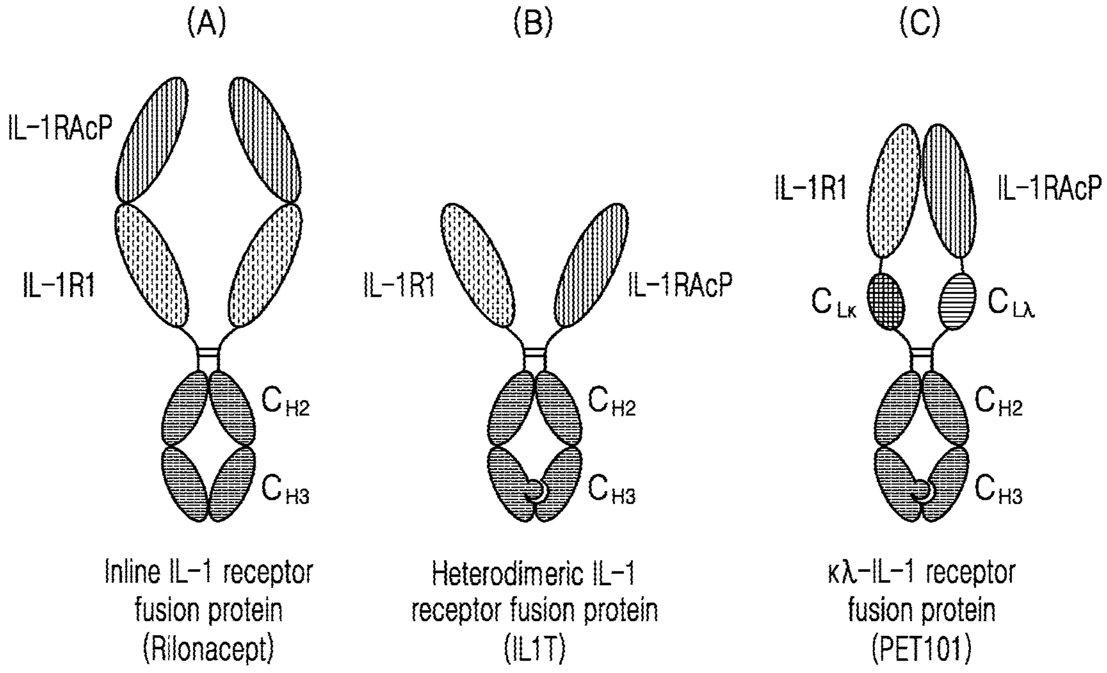
FIGS. 2A-2C show a schematic diagram of a method of preparing an IL-1 receptor Fc fusion protein.

As a specific example, the present inventors have constructed an Fc fusion protein, to which extracellular regions of the IL-1 receptors (IL-1R1 and IL-1RAcP) which are formed as heterodimers in nature were bound, by using the three kinds (inline homodimer (FIG. 1A), KiH heterodimer (FIG. 1C), and KiH κλ heterodimer (FIG. 1E)), which are expected to have a high formation rate of fusion proteins simultaneously having two polypeptides bound to Fc, and is expected to be relatively easily purified. In FIG. 2, A is an IL-1 specific inline homodimeric Fc fusion protein, in which the extracellular region of the IL-1 receptor is bound to Fc according to the structure A of FIG. 1, and is a fusion protein having the same sequence as rilonacept (related art), as an example of an IL-1 specific inline homodimeric Fc fusion protein; B is an IL-1 specific heterodimeric Fc fusion protein (IL1T) (related art), in which the extracellular region of the IL-1 receptor is bound to Fc according to the structure C of FIG. 1; and C is an example of an IL-1 specific heterodimeric Fc fusion protein, an IL-1 specific heterodimeric Fc fusion protein (PET101) constructed by linking the extracellular region of the IL-1 receptor to $C_{L\kappa}$ and $C_{L\lambda}$ according to the structure E of FIG. 1, and then linking to Fc (an embodiment of the present disclosure).

As in the above embodiment, one of the first target protein and the second target protein may be interleukin-1 receptor type 1 (IL1R1), and the other may be interleukin-1 receptor accessory protein (IL1RAcP). For example, the first target protein may be interleukin-1 receptor type 1 (IL1R1), the first linker may be a κ light chain constant region ($C_{L\kappa}$) or a variant thereof, the second target protein may be an interleukin-1 receptor accessory protein (IL1RAP), and the second linker may be a λ light chain constant region ($C_{L\lambda}$) or a variant thereof. For example, interleukin-1 receptor type 1 (IL1R1) and an interleukin-1 receptor accessory protein (IL1RAcP) may each be an ectodomain thereof.

As another specific example, the present inventors constructed a dual inhibitor in a form in which an interleukin-18-binding protein (IL18BP), a natural human IL-18A inhibitory protein, is fused to the C-terminus region of an IL-1 receptor Fc fusion protein, in order to develop a simultaneous inhibitor of the inflammasome effector cytokines IL-1α, IL-1β, and IL-18. Among IL-1 inhibitors, rilonacept, an inline homodimer, has a molecular weight of about 250 kDa, so that when IL18BP is fused, there may be a problem of decreased tissue permeability due to an additional increase of molecular weight. Therefore, the present inventors prepared an IL-1/IL-18 dual inhibitor in a form in which IL1T and PET101, heterodimeric IL-1 inhibitors having a relatively small molecular weight, are fused with IL18BP.

Figure 23:
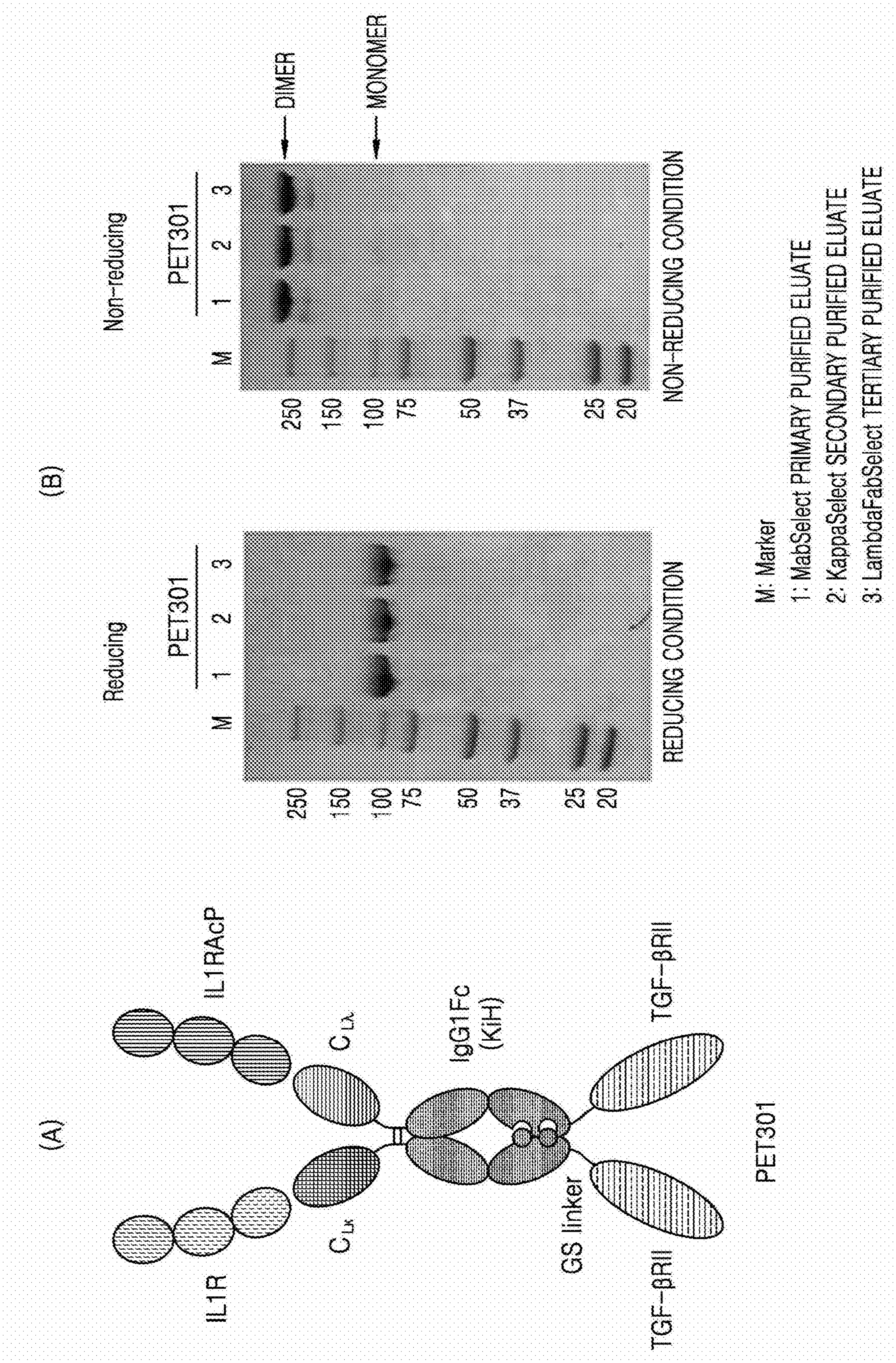
FIG. 23 shows a schematic diagram of IL-1/TGF-β bi-specific heterodimer PET301 (A), and SDS-PAGE results (B) of the products of each purification step of PET301 under reducing and non-reducing conditions.

As another specific example, the present inventors prepared an IL-1/TGF-β dual inhibitor based on PET101, considering that inhibition of IL-1 has a possibility to reduce MDSC formation and inflammation caused by TGF-β inhibition, and to increase anticancer efficacy. Specifically, in order to prepare an Fc fusion protein having bi-specificity for human IL-1 and TGF-β, PET301 construct, in which the extracellular domain of TGF-βRII is bound to the C-terminus of the Fc region of PET101, was designed (A of FIG. 23).

Accordingly, according to an embodiment, the heterodimeric Fc fusion protein may include interleukin-18 binding protein (IL18BP) or type II transforming growth factor-beta receptor (TGFβR II) as the third target protein.

Specifically, an interleukin-18 binding protein (IL18BP) may be included at one of the C-terminus of the first polypeptide and the C-terminus of the second polypeptide. More specifically, an interleukin-18 binding protein (IL18BP) may be included at the C-terminus of the second polypeptide.

In another example, the heterodimeric Fc fusion protein may include a type II transforming growth factor-beta receptor (TGFβRII) at both the C-terminus of the first polypeptide and the C-terminus of the second polypeptide.

In an embodiment, the heterodimeric Fc fusion protein may be one in which the CH3 region is mutated to promote heterodimer formation in the first Fc region and the second Fc region. Mutations for promoting heterodimer formation are known in the art, and these mutations may be included without particular limitation. For example, the CH3 region of the first Fc region and the second Fc region may include a knob-into-hole mutation.

In an embodiment, a first linker, a second linker, or both may be bound to the N-terminus of the Fc region hinge in the heterodimeric Fc fusion protein. The term 'hinge' refers to a portion of an antibody heavy chain polypeptide that connects the CH1 domain and the CH2 domain in a wild-type antibody heavy chain (for example, approximately from about position 216 to about position 320, or about position 226 to about position 230, according to the Kabat EU numbering system), which usually has 25 or less amino acid residues and has flexibility so that the binding sites with which it is associated are capable of moving independently. For example, a hinge may have an amino acid sequence of DKTHTCPXCP, HTCPXCP, or CPXCP (wherein X is S or P), but is not limited thereto.

In an embodiment, the heterodimeric Fc fusion protein may further include a third linker between the C-terminus of the first and/or the second polypeptide and the third target protein. In an embodiment, the linker moiety is a peptide linker having a length of 2 to 100 amino acids. Examples of linkers include linear peptides having at least two amino acid residues, such as Gly-Gly, Gly-Ala-Gly, Gly-Pro-Ala, Gly(G)n, and Gly-Ser (GS) linkers. GS linkers include, but are not limited to, (GS)n, (GSGSG)n (SEQ ID NO:16), $(G_2S)n$, $G_2S_2G$ (SEQ ID NO:17), $(G_2SG)n$ (SEQ ID NO:18), $(G_3S)n$ (SEQ ID NO:19), $(G_4S)n$ (SEQ ID NO:20), (GGSGG)nGn (SEQ ID NO:21) and $GSG_4SG_4SG$ (SEQ ID NO:22), wherein n is 1 or more. In certain instances, the linker may be $(G_4S)_2$ (SEQ ID NO:23).

In an embodiment, the immunoglobulin Fc region may be an Fc region derived from IgG, IgA, IgD, IgE, or IgM, or a combination or hybrid thereof. Specifically, the immunoglobulin Fc region may be an IgG Fc region, in particular an IgG1 Fc region, but is not limited thereto.

Compositions, Uses and Methods

The contents described above with respect to the heterodimeric Fc fusion protein are equally applicable to the following compositions, uses, methods, and the like.

Another aspect of the present disclosure provides a pharmaceutical composition including the heterodimeric Fc fusion protein as an active ingredient, and a pharmaceutically acceptable carrier.

A pharmaceutically acceptable carrier enhances or stabilizes the composition or facilitates preparation of the composition. The pharmaceutically acceptable carrier includes physiologically compatible solvents, dispersion media, coating agents, antibacterial and antifungal agents, isotonic agents, absorption delaying agents, and the like.

The pharmaceutical compositions of the present disclosure may be administered by a variety of methods known in the art. The route and/or mode of administration will depend on the desired outcome. Administration may be intravenous, intramuscular, intraperitoneal, or subcutaneous, or the pharmaceutical composition may be administered adjacent to the target site. A pharmaceutically acceptable carrier should be suitable for intravenous, intramuscular, subcutaneous, parenteral, spinal, or epidermal administration (for example, by injection or infusion). The compositions have to be sterile and fluid. The compositions may be in a lyophilized form. Isotonic agents, for example, sugars, polyalcohols such as mannitol or sorbitol, and sodium chloride may be included in the composition. The pharmaceutical compositions of the present disclosure may be prepared according to methods well known and commonly practiced in the related art.

Dosage levels of the active ingredient of the pharmaceutical composition may be varied to obtain an amount of the active ingredient effective to achieve a desired therapeutic response for a particular patient, composition, and mode of administration without being toxic to the patient. The selected dosage level will depend on a variety of pharmacokinetic factors, for example, the particular composition of the present disclosure used, or route of administration, time of administration, rate of excretion, duration of treatment, other drugs, compounds, and/or substances used in combination, age, sex, weight, condition, general health, and previous medical history of the patient being treated, and other factors. As a non-limiting example, dosages range from about 0.0001 mg/kg body weight to 100 mg/kg body weight, more generally, 0.1 mg/kg body weight to 20 mg/kg body weight. An example treatment regimen entails administration once every week, or once every two weeks, or once every month, or once every 3 months to 6 months.

In an embodiment, the composition may be for preventing or treating an immune-related disease or disorder. In an embodiment, the immune related disease or disorder may be cancer, an autoimmune disease, or an inflammatory disease.

In an embodiment, the composition may further include one or more therapeutic agents. In an embodiment, the therapeutic agent may be an immune checkpoint inhibitor, for example, one or more of a PD1 inhibitor, a PD-L1 inhibitor, and a CTLA4 inhibitor.

Still another aspect of the present disclosure provides a composition for use as a linker between a target protein and an Fc region, including a κ light chain constant region ($C_{L\kappa}$) or a variant thereof, and a λ light chain constant region ($C_{L\lambda}$) or a variant thereof, in the heterodimeric Fc fusion proteins including the target protein and the immunoglobulin Fc region.

Still another aspect of the present disclosure provides a use of the κ light chain constant region ($C_{L\kappa}$) or a variant thereof, and the λ light chain constant region ($C_{L\lambda}$) or a variant thereof, as linkers between a target protein and an Fc region, in the heterodimeric Fc fusion proteins including the target protein and the immunoglobulin Fc region.

Still another aspect of the present disclosure provides a method of using the κ light chain constant region ($C_{L\kappa}$) or a variant thereof, and the λ light chain constant region ($C_{L\lambda}$) or a variant thereof, in the heterodimeric Fc fusion proteins as linkers between a target protein and an Fc region, in the heterodimeric Fc fusion proteins including the target protein and the immunoglobulin Fc region.

Still another aspect of the present disclosure provides a method of preparing the heterodimeric Fc fusion proteins, including introducing each of the κ light chain constant region ($C_{L\kappa}$) or a variant thereof, and the λ light chain constant region ($C_{L\lambda}$) or a variant thereof, as linkers between a target protein and an Fc region.

Still another aspect of the present disclosure provides a method of purifying the heterodimeric Fc fusion proteins, including purifying the heterodimeric Fc fusion proteins based on the affinity of the κ light chain constant region ($C_{L\kappa}$) and the λ light chain constant region ($C_{L\lambda}$). In an embodiment, a purification method may include:

1) performing immunoglobulin affinity chromatography;
2) performing affinity chromatography of the κ light chain constant region ($C_{L\kappa}$); and
3) performing affinity chromatography of the λ light chain constant region ($C_{L\lambda}$).

Various Fc variants may be used to increase binding to neonatal Fc receptor (FcRn) and increase half-life in the serum. The binding of the Fc region to FcRn prevents degradation by endosomes when the antibody or Fc fusion protein is endocytosed, and induces re-release into the blood through pH-dependent dissociation, resulting in a long drug half-life, and high exposure in blood, mediating pharmacokinetic properties of antibodies and Fc fusion proteins. However, many Fc fusion proteins exhibit low FcRn binding capacity compared to antibodies due to interference between a Fc region and a binding protein, and low FcRn binding strength correlates with the short half-life of the Fc fusion protein.

The present inventors considered that κλ Fc fusion protein technology may have an advantage of increased FcRn binding capacity by increasing the distance between the Fc region and the binding protein by locating the $C_{L\kappa}$ and $C_{L\lambda}$ regions at the N-terminus of the hinge region and reducing interference by each other, in addition to the advantage in purification, and this was confirmed through experiments.

Accordingly, still another aspect of the present disclosure provides a method of increasing FcRn binding capacity of the heterodimeric Fc fusion proteins, including introducing each of the κ light chain constant region ($C_{L\kappa}$) or a variant thereof, and the A light chain constant region ($C_{L\lambda}$) or a variant thereof, as linkers between a target protein and an Fc region.

In addition, provided is a method of increasing half life of the heterodimeric Fc fusion proteins, including introducing each of the κ light chain constant region ($C_{L\kappa}$) or a variant thereof, and the λ light chain constant region ($C_{L\lambda}$) or a variant thereof, as linkers between a target protein and an Fc region.

The Fc region of an antibody mediates the immune effector function of the antibody by binding to the Fc gamma receptor (Fcγ receptor) on the surface of immune cells, in addition to FcRn. The present inventors tested the possibility that the κλ Fc fusion protein technology has an advantage of increased binding capacity to Fc gamma receptors as well as FcRn, and confirmed that the fusion protein has increased binding ability to FcγRI and FcγRIIIa.

Antibody-dependent cell-mediated cytotoxicity (ADCC) refers to a cell-mediated reaction in which non-specific cytotoxic cells expressing FcγR recognize antibodies bound to a target cell and subsequently cause lysis of the target cell. ADCC correlates with binding to FcγRIIIa, and increased binding to FcγRIIIa leads to an increase in ADCC activity.

Accordingly, still another aspect of the present disclosure provides a method of increasing FcγR binding capacity of the heterodimeric Fc fusion proteins, including introducing each of the κ light chain constant region ($C_{L\kappa}$) or a variant thereof, and the λ light chain constant region ($C_{L\lambda}$) or a variant thereof, as linkers between a target protein and an Fc region.

In addition, provided is a method of increasing antibody-dependent cell-mediated cytotoxicity (ADCC) of the heterodimeric Fc fusion proteins, including introducing each of the κ light chain constant region ($C_{Lκ}$) or a variant thereof, and the λ light chain constant region ($C_{Lλ}$) or a variant thereof, as linkers between a target protein and an Fc region.

Hereinafter, the present disclosure will be described in more detail with reference to specific examples, but this is only intended to help understanding of the present disclosure and is not intended to limit the scope of the present disclosure in any way.

Comparative Example 1: Preparation of IL-1 Specific Heterodimeric Fc Fusion Protein (IL1T)

In order to implement an IL-1 specific heterodimeric Fc fusion protein having the configuration of FIG. 2(B), by applying a knob-into-hole mutagenesis technique to the Fc region (SEQ ID NO:1) of human immunoglobulin G1 (IgG1), gene sequences encoding polypeptides of Fc with a knob mutation (S354C and T366W; SEQ ID NO:2), and Fc with a hole mutation (Y349C, T366S, L368A, Y407V; SEQ ID NO:3) were obtained. Gene sequences encoding 1 to 333 amino acid residues constituting the signal peptide and extracellular domain of human IL-1R1 (GenBank: AAM88423.1), or 1 to 359 amino acid residues constituting the signal sequence and extracellular domain of human IL-1RAcP (GenBank: BAA25421.1) were chemically synthesized (Integrated DNA Technologies, IA, USA), and cloned into each vector. Vectors capable of expressing polypeptides corresponding to IL-1R-hinge region-CH2-CH3 (S354C, T366W) (SEQ ID NO:4) and IL-1RAcP-hinge region-CH2-CH3 (Y349C, T366S, L368A, Y407V) (SEQ ID NO:5) were referred to as P001 and P002, respectively.

Figure 3A:
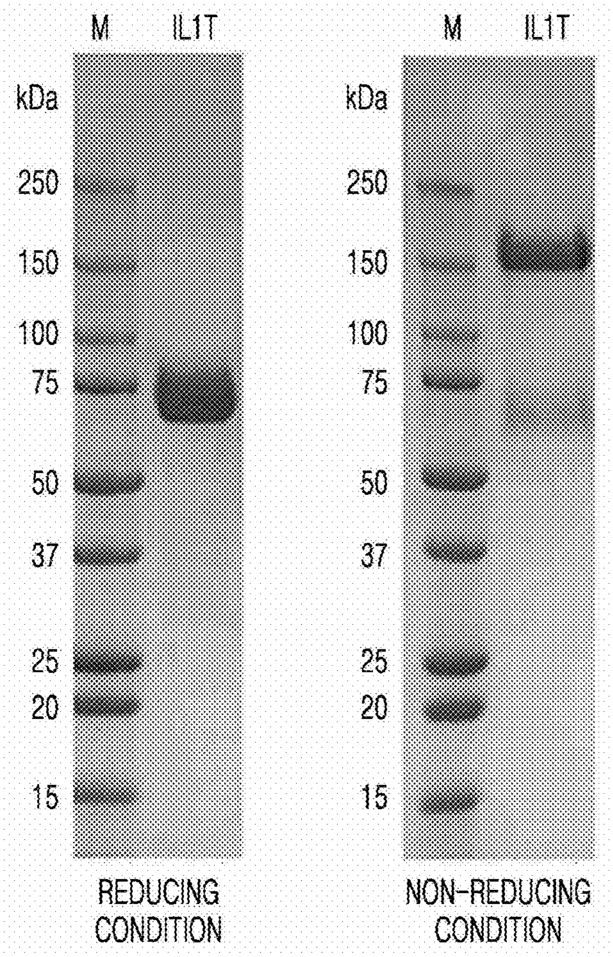
FIGS. 3A and 3B show results of SDS-PAGE analysis (FIG. 3A), and results of size exclusion chromatography analysis (FIG. 3B) of IL1T, a heterodimeric IL-1 trap.
Figure 3B:
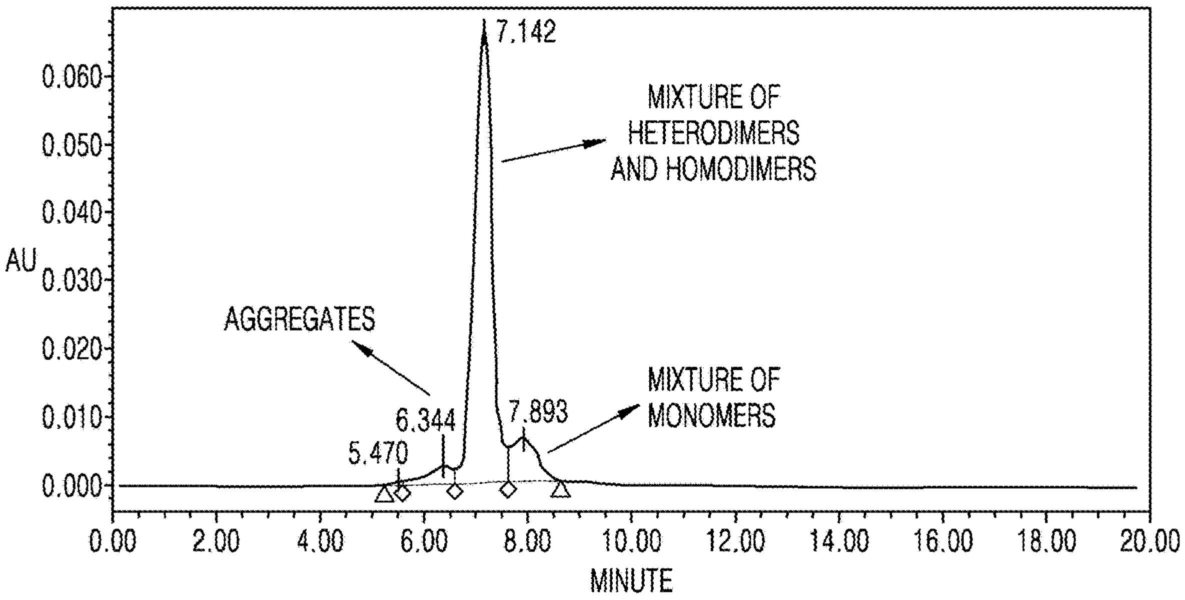

Co-transfection of P001 and P002 vectors was performed in ExpiCHO-S™ (Gibco, A29127), a Chinese hamster ovary-derived cell line, and the heterodimeric IL-1 trap expressed through this transient expression was referred to as IL1T. All reagents used in the procedure for transient expression were prepared according to the manufacturer's (Gibco) manual, and were performed according to the maximum titer production protocol in the manual. The culture at day 12 was filtered by using a Sartoclear Dynamics® Lab V (Sartorius, SDLV-1000-40C-E) filter system, followed by purification by using a HiTrap MabSelect SuRe (GE helathcare, 11003493) purification column, and the sample was concentrated by using an Amicon Ultra-15 Concentration Filter Unit (Merck millipore). Concentration of the final product, in which purification was completed, was quantified based on the sample's intrinsic extinction coefficient and molecular weight. The purified product was analyzed by using sodium dodecyl sulfate polyacrylamide gel electrophoresis (SDS-PAGE) and size exclusion chromatography (SEC) (FIGS. 3A and 3B). SDS-PAGE analysis was performed under non-reducing conditions and reducing conditions, and bands of each size were identified through Coomassie Brilliant Blue staining (FIG. 3A). Under reducing conditions, a mixture of IL-1R-hinge region-CH2-CH3 (S354C, T366W) monomers and IL-1RAcP-hinge region-CH2-CH3 (Y349C, T366S, L368A, Y407V) monomers was confirmed at about 70 kDa. Under non-reducing conditions, a product presumed to be a mixture of heterodimers and homodimers was confirmed at about 150 kDa, and monomers that were not assembled were identified at about 70 kDa (FIG. 3A). Alliance® HPLC—e2695 Separations Module (Waters, 2695) equipped with an Agilent Bio SEC-3 HPLC column (Agilent, 5190-2511) was used for the size exclusion chromatography analysis. As a result of the analysis, 82.88% of a mixture of heterodimers (IL1T) and homodimers was found to be present at a retention time of 7.142 minutes, aggregates were detected at retention times of 5.470 minutes and 6.344 minutes, and a mixture of monomers was detected at a retention time of 7.893 minutes. (FIG. 3B).

Example 1: Preparation of IL-1 Specific κλ Heterodimeric Fc Fusion Protein (PET101)

In order to prepare IL-1 specific heterodimeric Fc fusion protein to which κλ Fc fusion protein technology is applied, an antibody light chain kappa constant region was introduced between the IL-1R extracellular region and the hinge region (SEQ ID NO:6), and an antibody light chain lambda constant region was introduced between the IL-1RAcP extracellular region and the hinge region (SEQ ID NO:7). In this process, in order to prevent unnecessary assembly, the cysteine present at the C-terminus of the constant region of natural kappa and lambda was substituted with serine. Expression vectors encoding the amino acid sequences of IL-1R-$C_L$κ-hinge region-CH2-CH3 (S354C, T366W) and IL-1RAcP-$C_L$λ-hinge region-CH2-CH3 (Y349C, T366S, L368A, Y407V) prepared in this configuration (SEQ ID NO:8 and SEQ ID NO:9) are referred to as P003 and P004, respectively, and the heterodimer generated by performing co-transfection in the ExpiCHO-S™ cell line was named PET101.

Figure 4A:
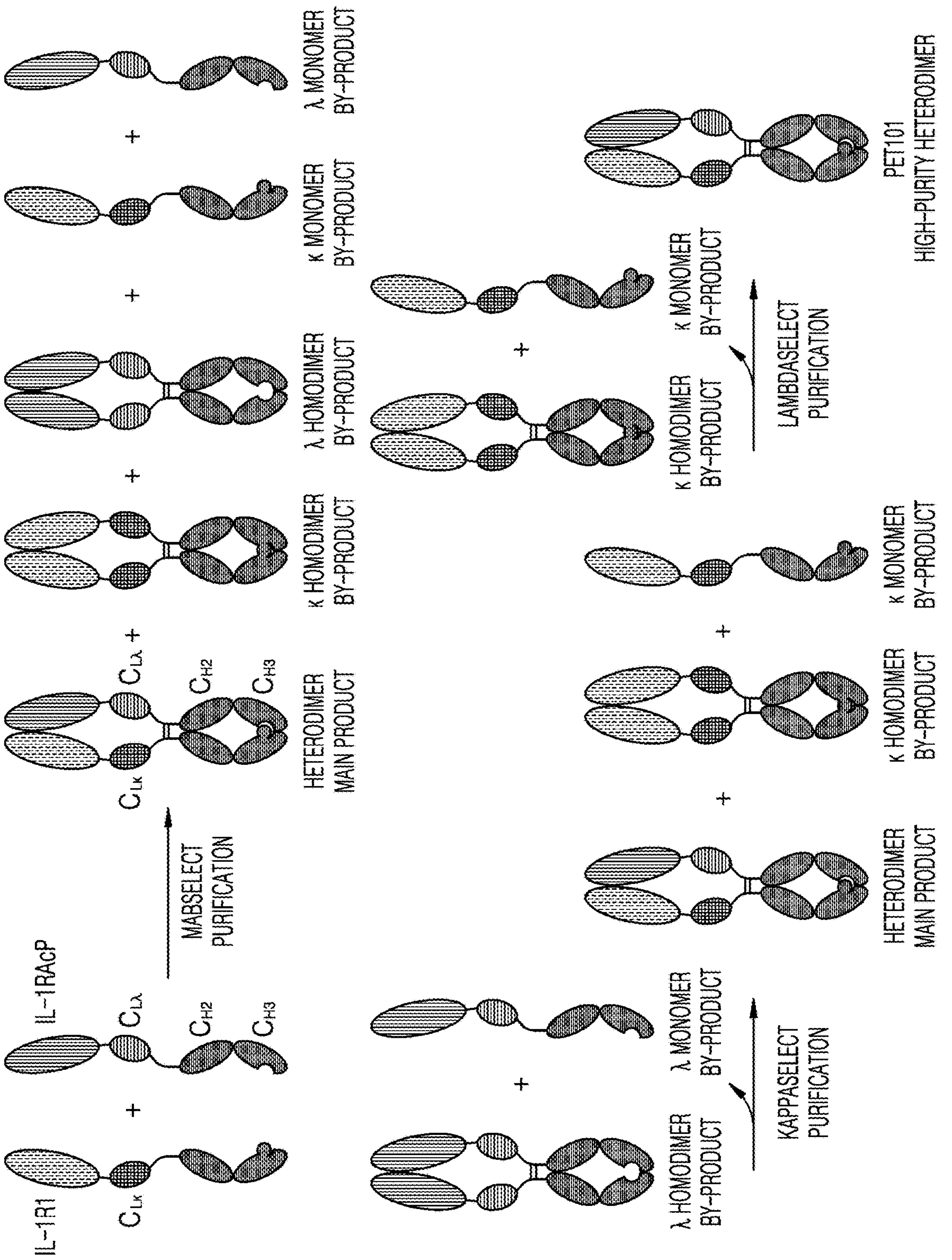
FIG. 4A shows a schematic diagram of main products and by-products of each purification step of PET101, a κλ heterodimer IL-1 trap.
Figure 4B:
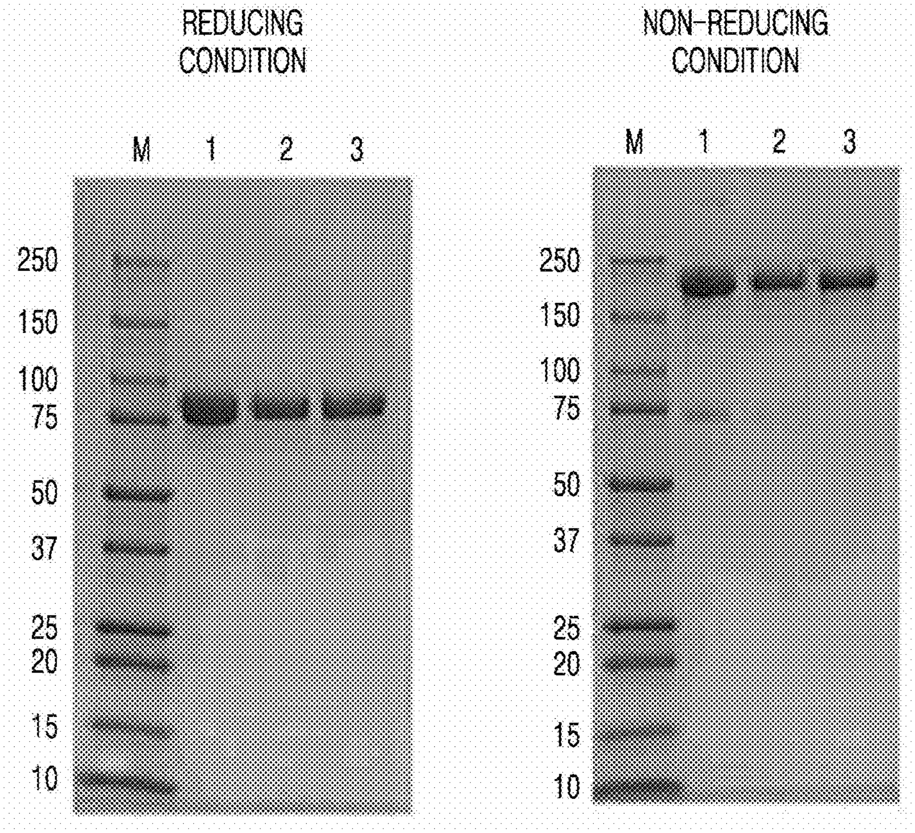
FIG. 4B shows SDS-PAGE analysis results of the eluates of each purification step of PET101.
Figure 4C:
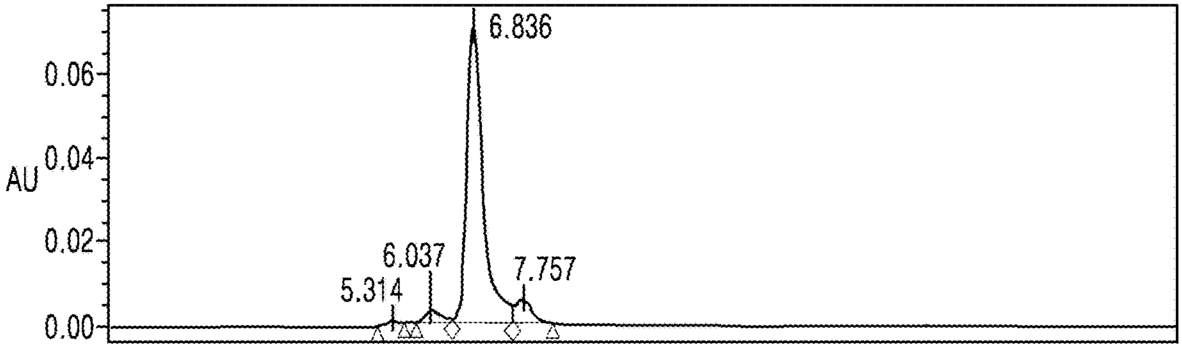
FIGS. 4C and 4D show results of size exclusion chromatography analysis of the primary purification eluate of PET101 and results of size exclusion chromatography analysis of the tertiary purification eluate of PET101, respectively.
Figure 4D:
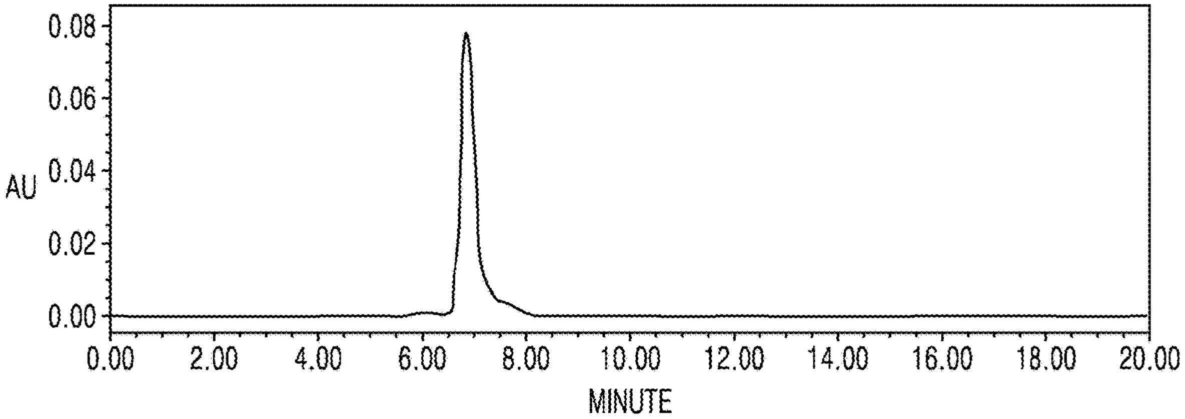

The purification process of PET101 and expected main products and by-products of each purification step are shown in FIG. 4A. In detail, affinity chromatography-based purification was performed in the same manner as in Comparative Example 1. The primary purified product was subjected to affinity chromatography by using KappaSelect resin (GE healthcare, 17545801) followed by affinity chromatography by using LambdaFabSelect resin (GE healthcare, 17548201). Dialysis, concentration, quantification, SDS-PAGE, and size exclusion chromatography analysis of the primary (MabSelect), secondary (KappaSelect), and tertiary (LambdaFabSelect) purified products were performed in the manner described in Comparative Example 1. In the SDS-PAGE analysis of the MabSelect primary purified eluate under a non-reducing condition, unassembled monomers were identified at about 70 kDa, but when all the purification steps were completed to the tertiary purification, the monomers were removed and proteins expected to be PET101 of about 180 kDa were confirmed ('1' in FIG. 4B). In the purity analysis using size exclusion chromatography, heterodimers, homodimers, monomers, etc., were present in the first purified product, and the dimer peak was confirmed at a retention time of 6.836 seconds, and the area of this mixture was confirmed to be 87.57% ('2' of FIG. 4B). Secondary (KappaSelect) and tertiary (LambdaFabSelect) affinity chromatography serial purifications were performed for separation of heterodimers from the primary purified product. In the SDS-PAGE results of the LambdaFabSelect tertiary purified product, which is the final purified product, no monomer was identified, and a peak of products presumed to be heterodimers was confirmed ('3' of FIG. 4B). In the size exclusion chromatography analysis, the peak of the products presumed to be heterodimers was eluted with a retention time of 6.838 minutes, and the purity of the final purified product was confirmed to be 99.31% ('3' of FIG. 4B).

Experimental Example 1: Analysis of Content of PET101 Heterodimer

Figure 5:
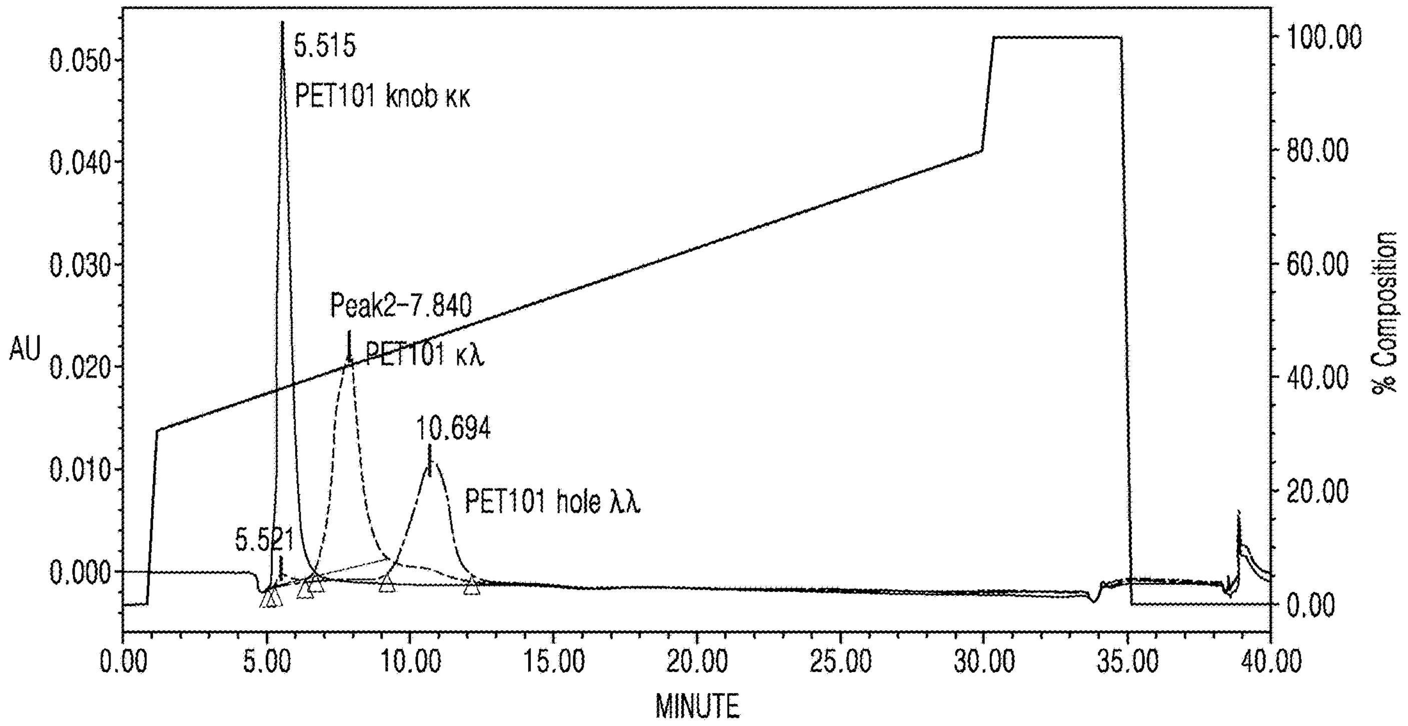
FIG. 5 shows hydrophobic interaction chromatography (HIC) analysis results of PET101.

In order to confirm a content of the heterodimers in the final purified product of PET101 obtained in Example 1, hydrophobic interaction chromatography analysis, which is capable of separating the heterodimers and the homodimers, was performed. As a chromatography column, a MAbPac HIC-10 column (4.6×250 mm, 5 μm; Thermo Fisher Scientific) was used. For homodimer analysis, IL-1R-$C_{L\kappa}$-hinge region-CH2-CH3 homodimer (PET101 knob κκ) and IL-1RAcP-$C_{L\lambda}$-hinge region-CH2-CH3 homodimer (PET101 hole λλ) were expressed and purified in the method described in Example 1 and compared with the final purified product of PET101. In hydrophobic interaction chromatography, it was confirmed that PET101 knob BB homodimers were eluted first, as shown in FIG. 5, and then, the final purified product of PET101, and PET101 hole BB homodimers were eluted in this order. The ratio of heterodimers (PET101 κλ), not homodimers, in the final purified product of PET101 was measured to be 98.02%, and it was demonstrated that high-purity heterodimer separation was possible through the purification process described in Example 1.

Experimental Example 2: Analysis of Binding Ability to IL-1β by Using Enzyme-Linked Immunosorbent Assay (ELISA)

Figure 6:
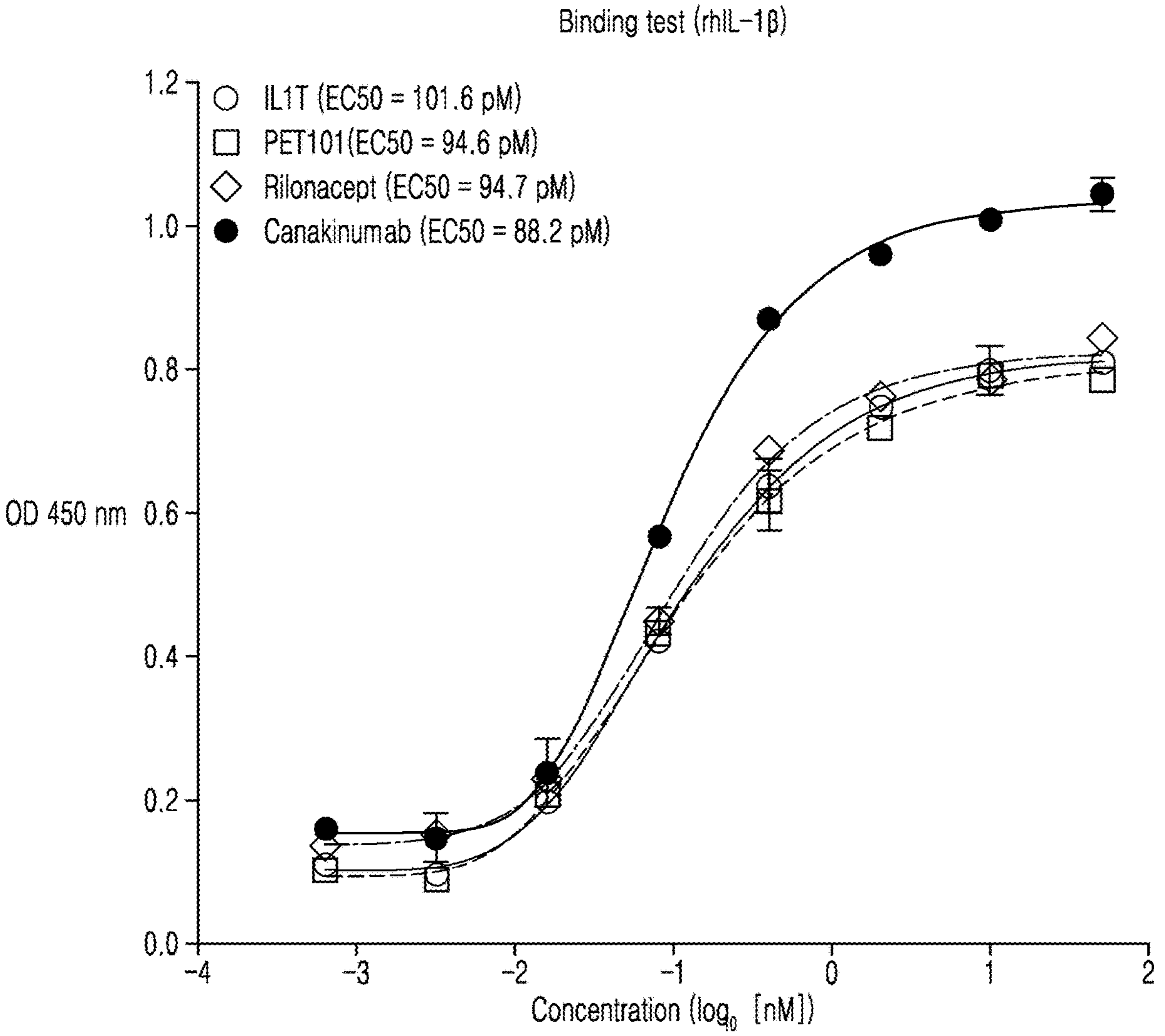
FIG. 6 shows results of analyzing binding capacity of IL1T, PET101, canakinumab, and rilonacept to human IL-1β, by using enzyme-linked immunosorbent assay (ELISA).
Figure 7A:
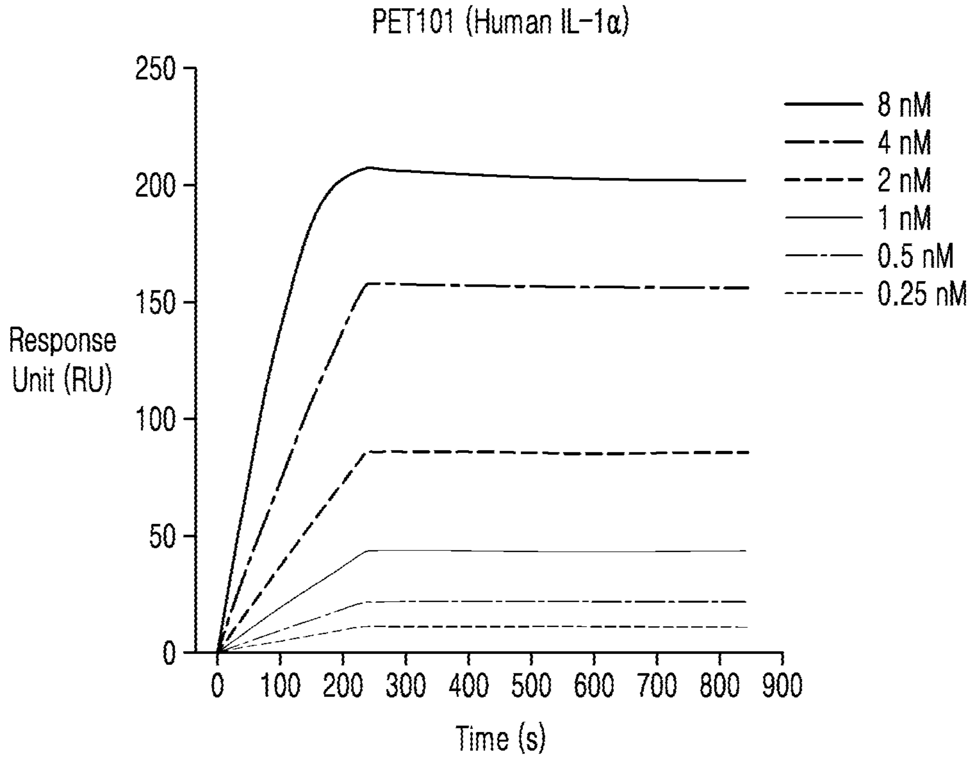
FIGS. 7A, 7B, 7C, 7D, and 7E show results of analyzing binding capacity of PET101 to human IL-1α, human IL-1β, monkey IL-1β, mouse IL-1α, and mouse IL-1β, respectively, by using surface plasmon resonance (SPR).
Figure 7B:
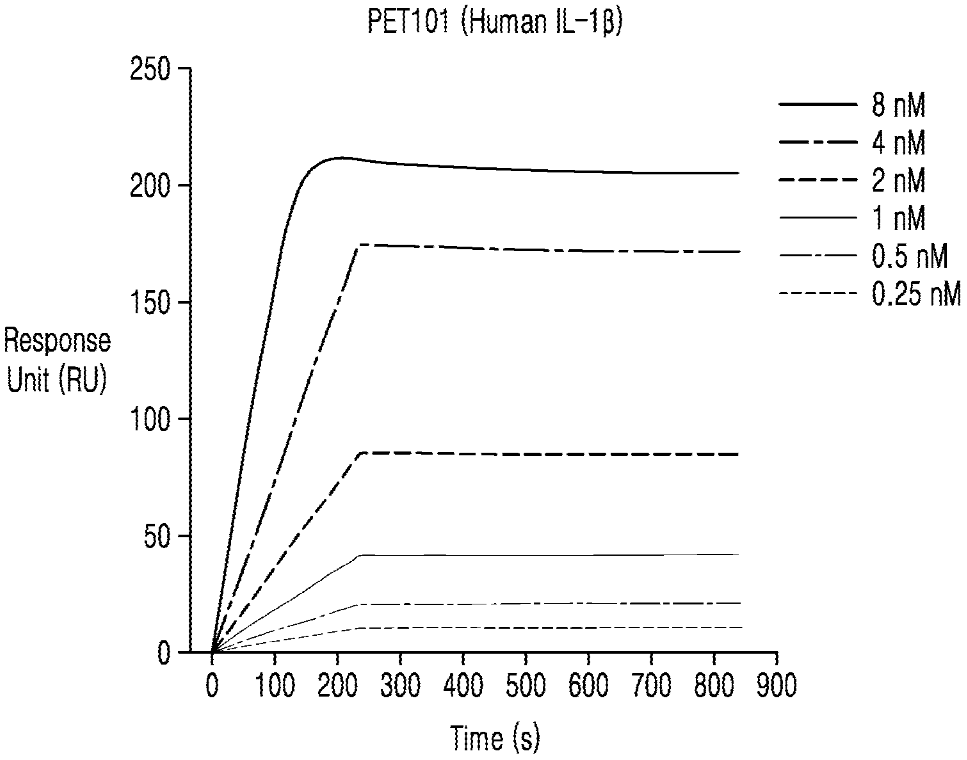
Figure 7C:
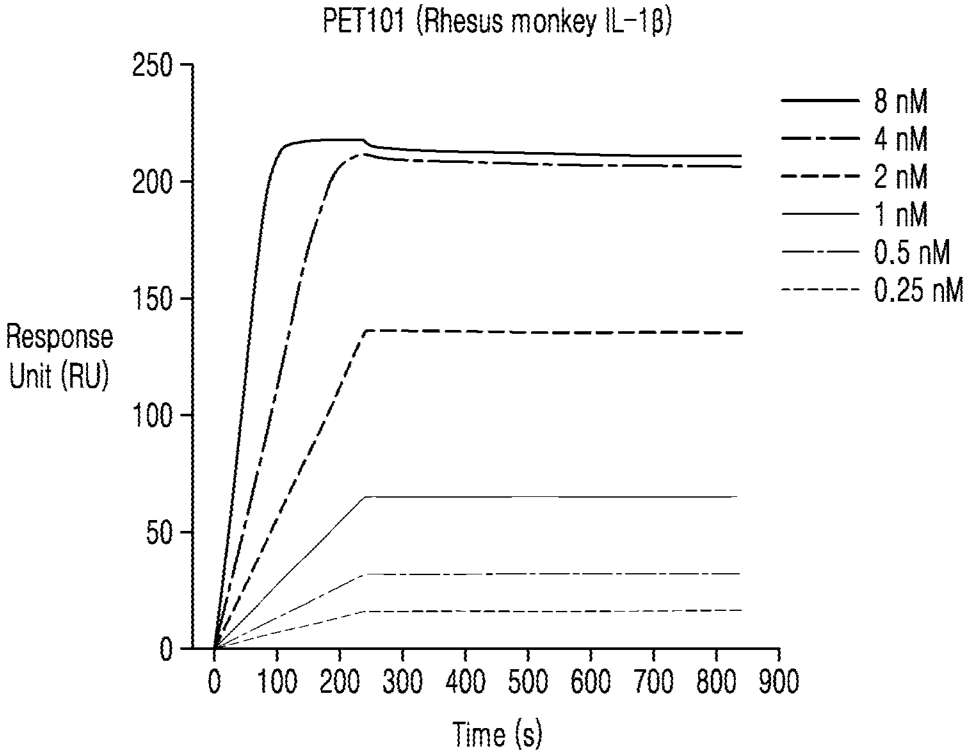
Figure 7D:
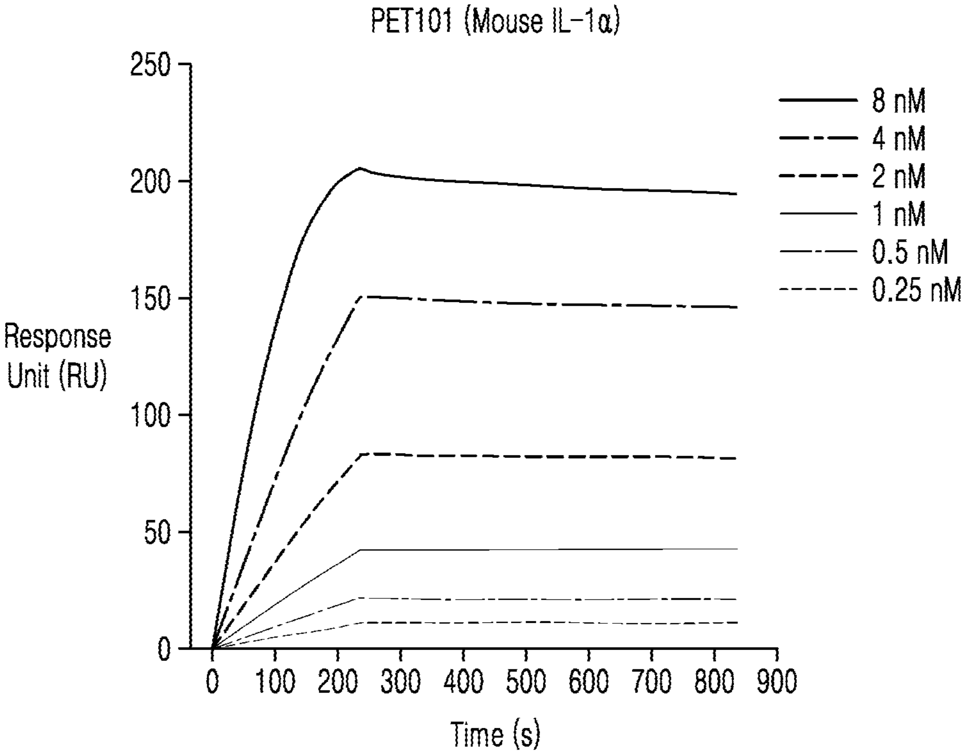
Figure 7E:
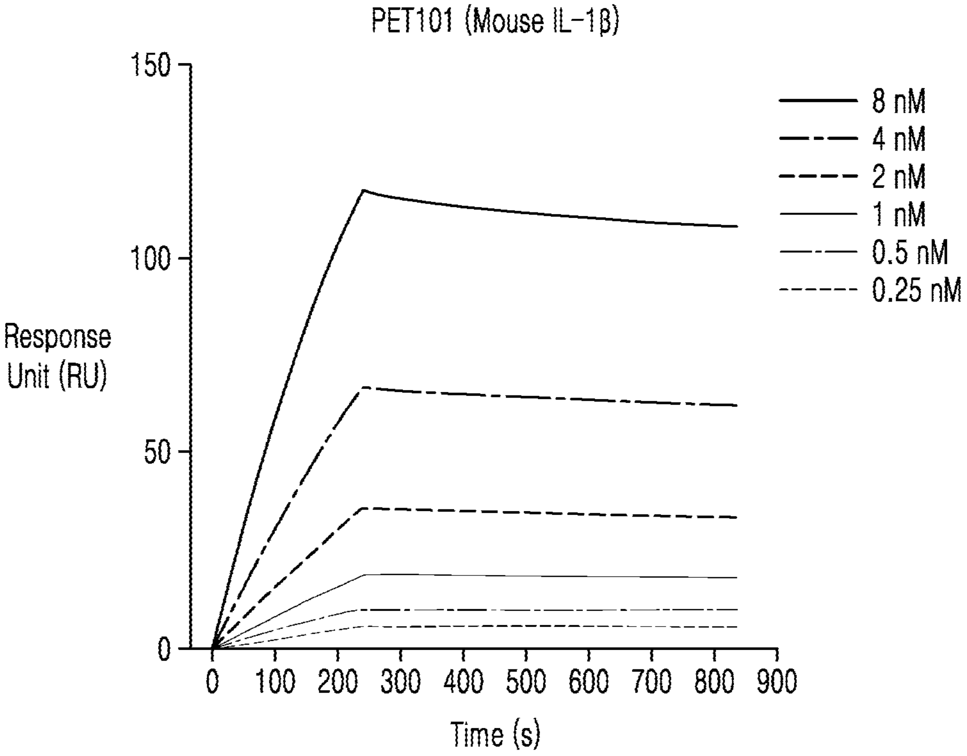
Figure 7F:
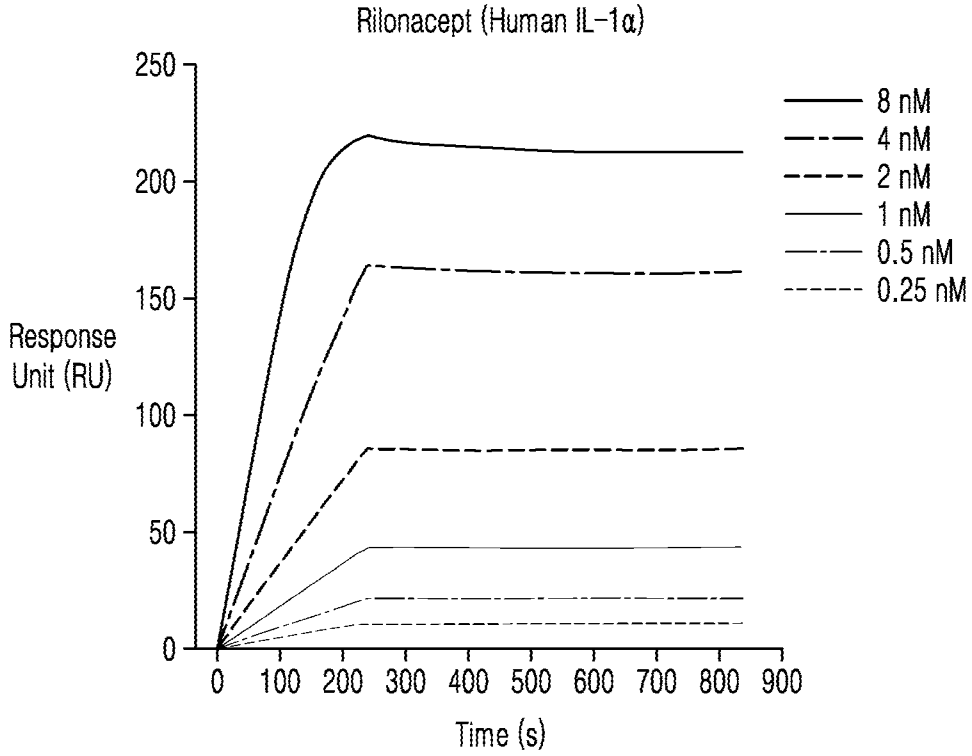
FIGS. 7F, 7G, 7H, 7I, and 7J show results of analyzing binding capacity of rilonacept to human IL-1α, human IL-1β, monkey IL-1β, mouse IL-1α, and mouse IL-1β, respectively by using surface plasmon resonance (SPR).
Figure 7G:
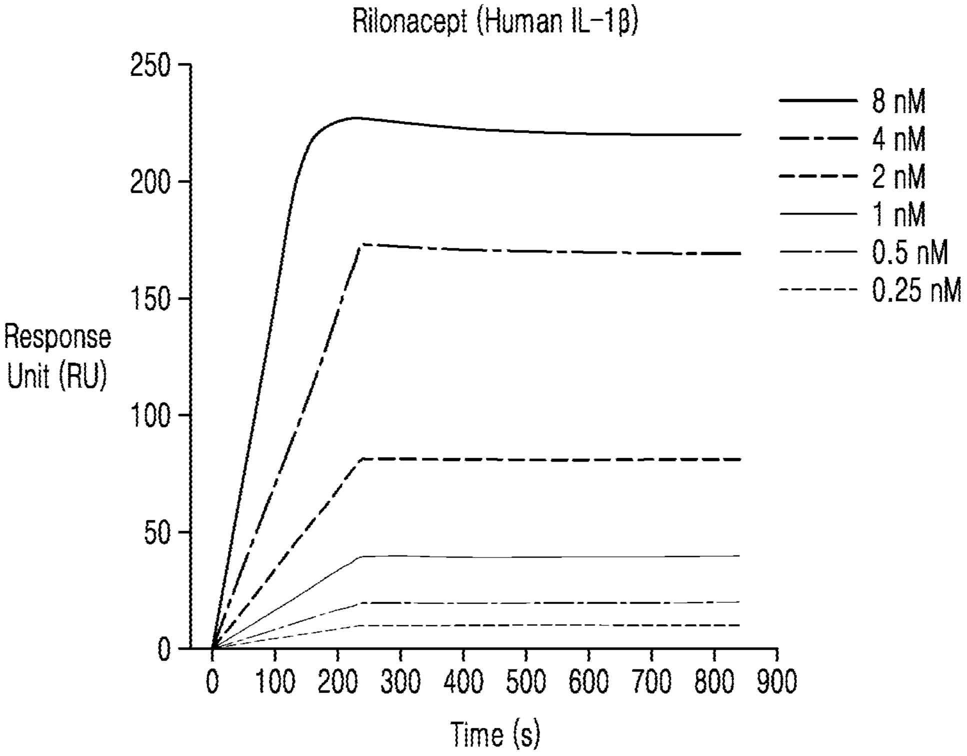
Figure 7H:
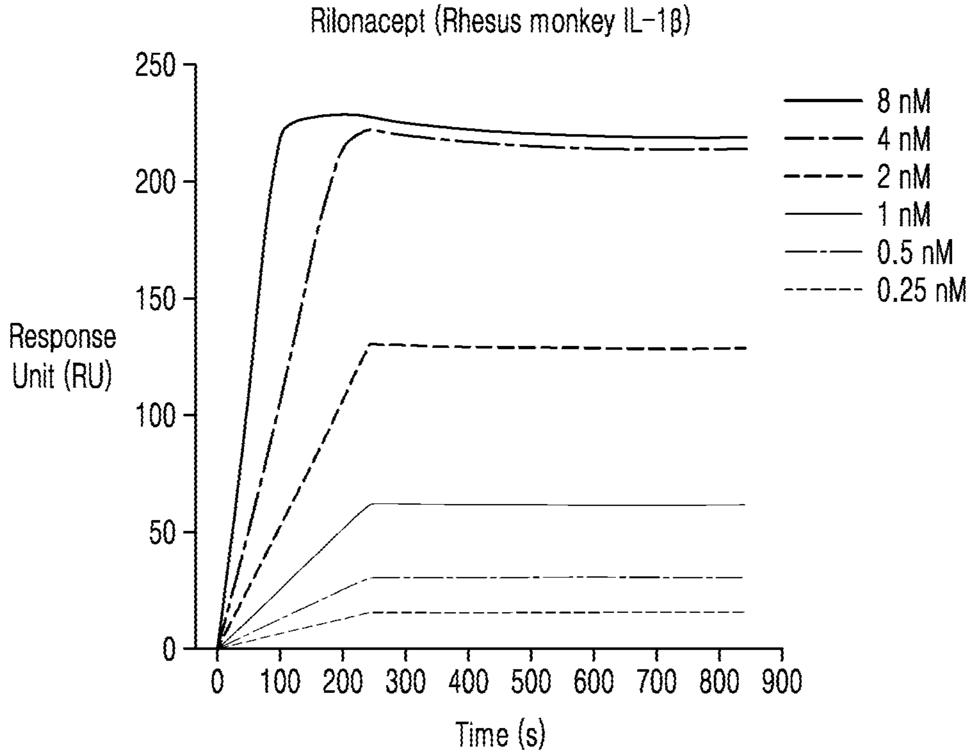
Figure 7I:
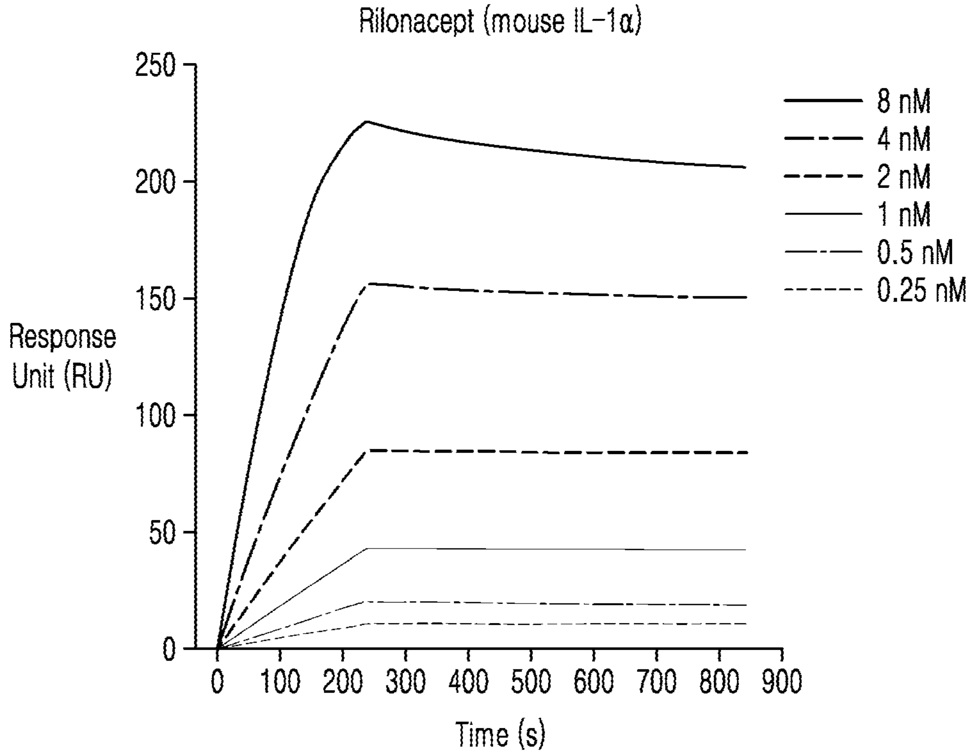
Figure 7J:
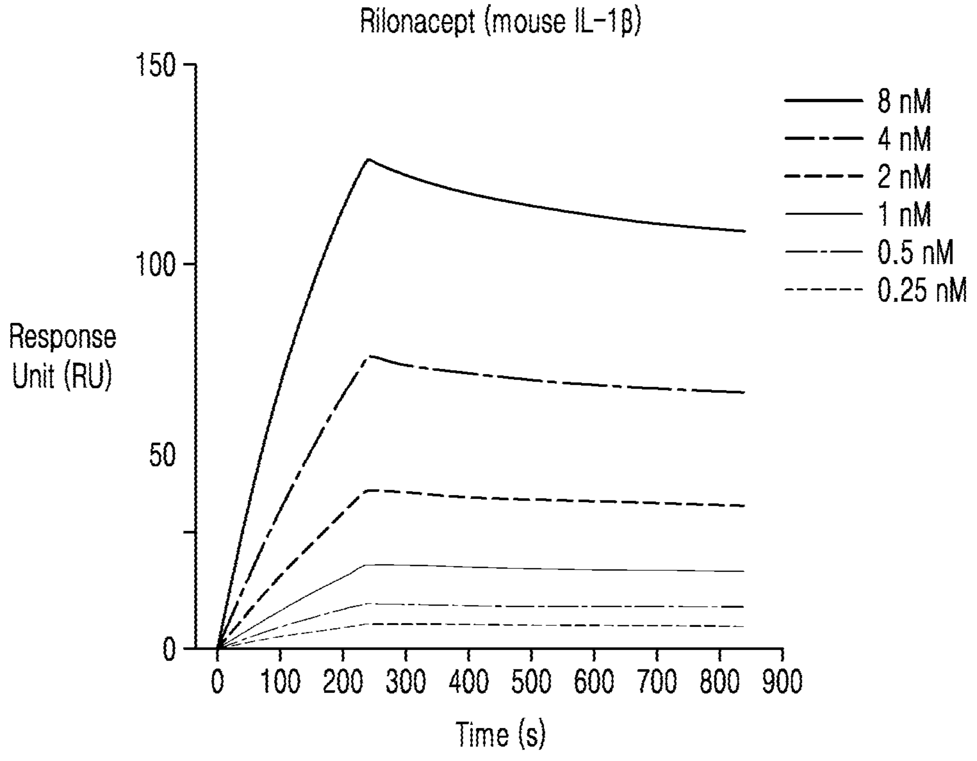
Figure 7K:
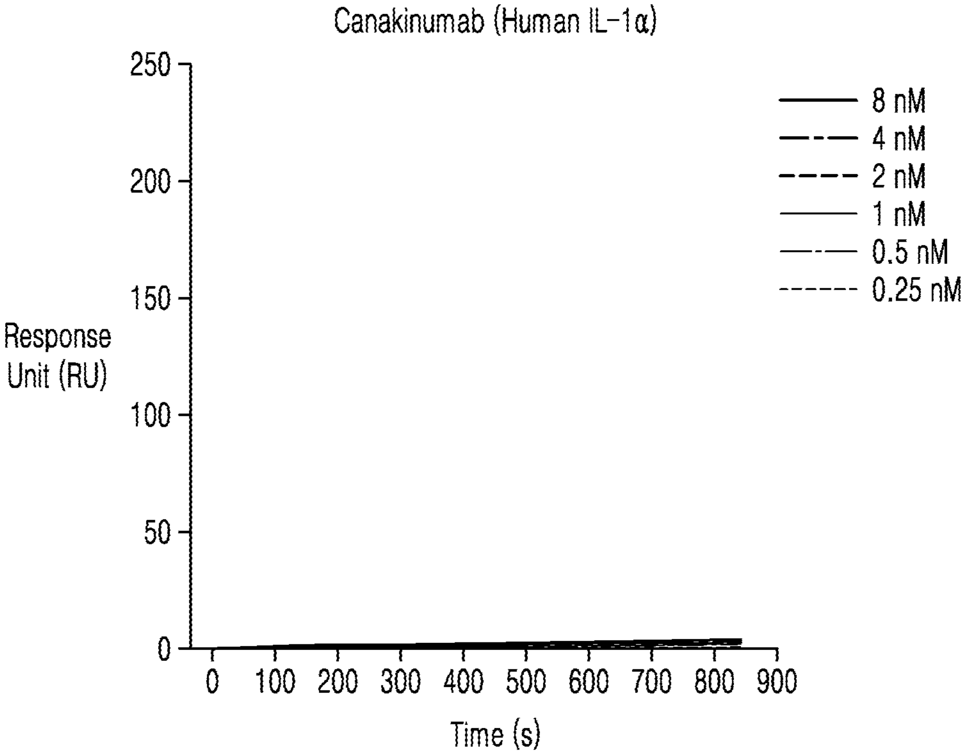
Figure 7L:
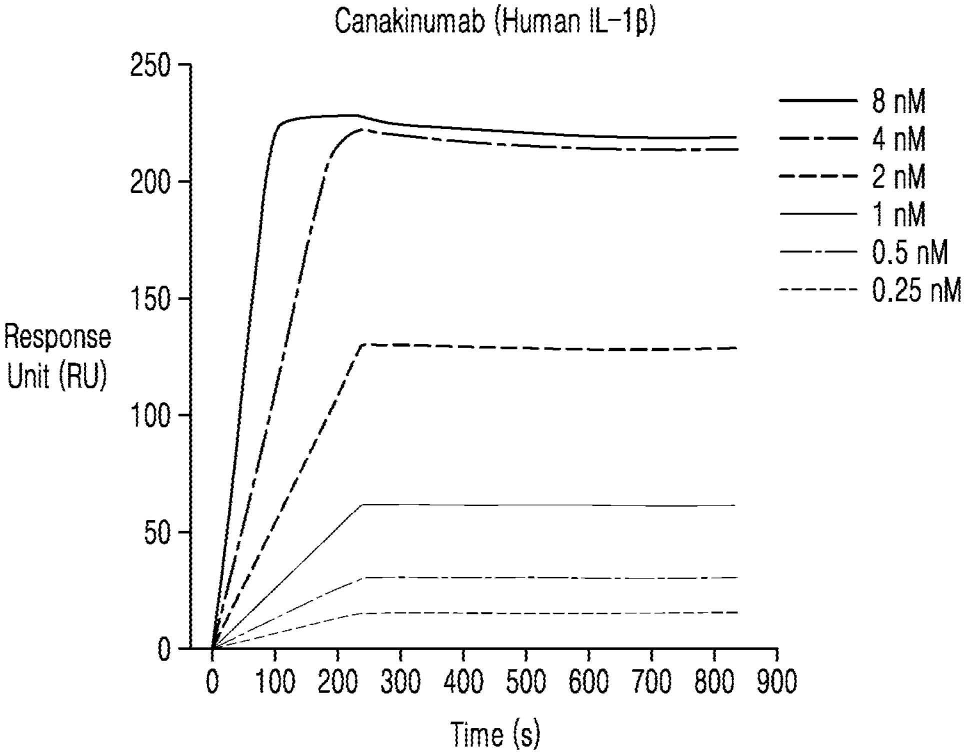
Figure 7M:
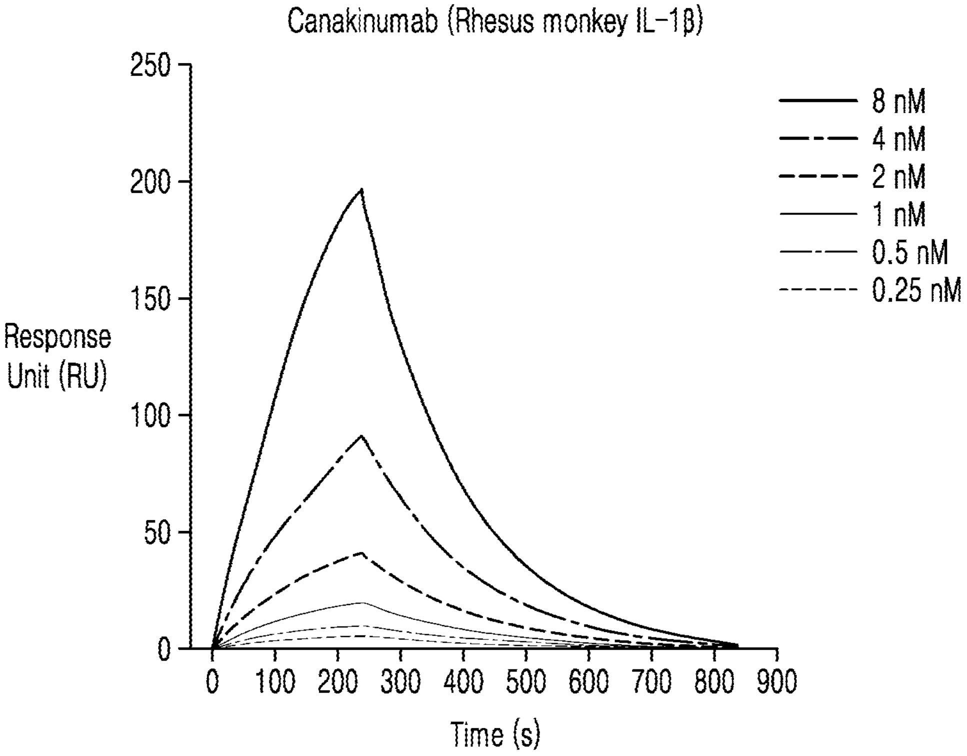
Figure 7N:
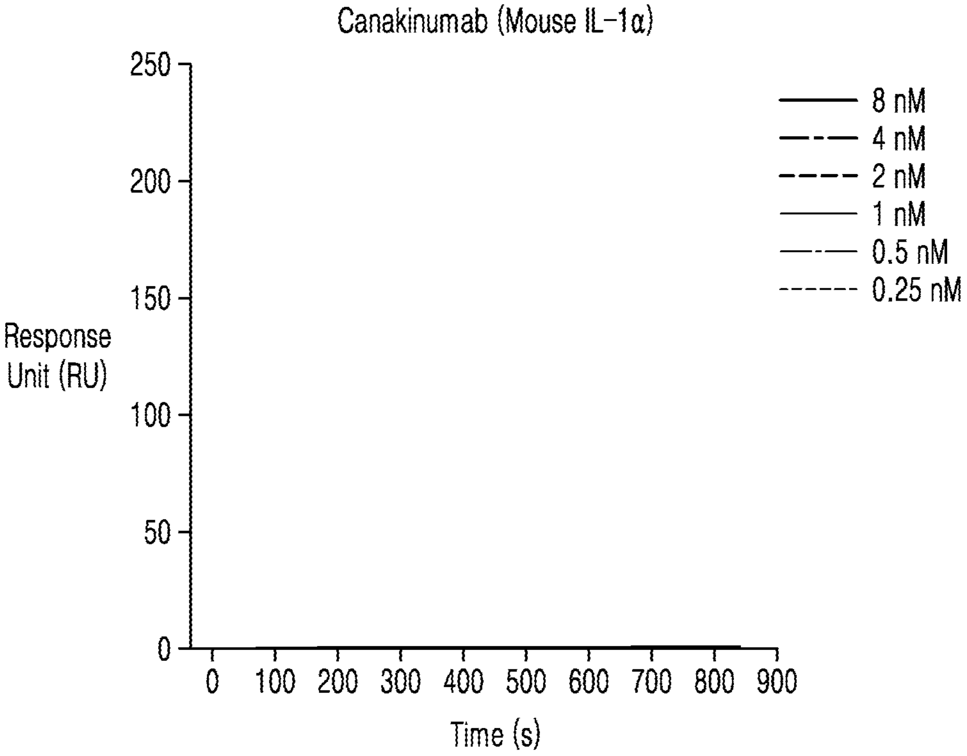
Figure 70:
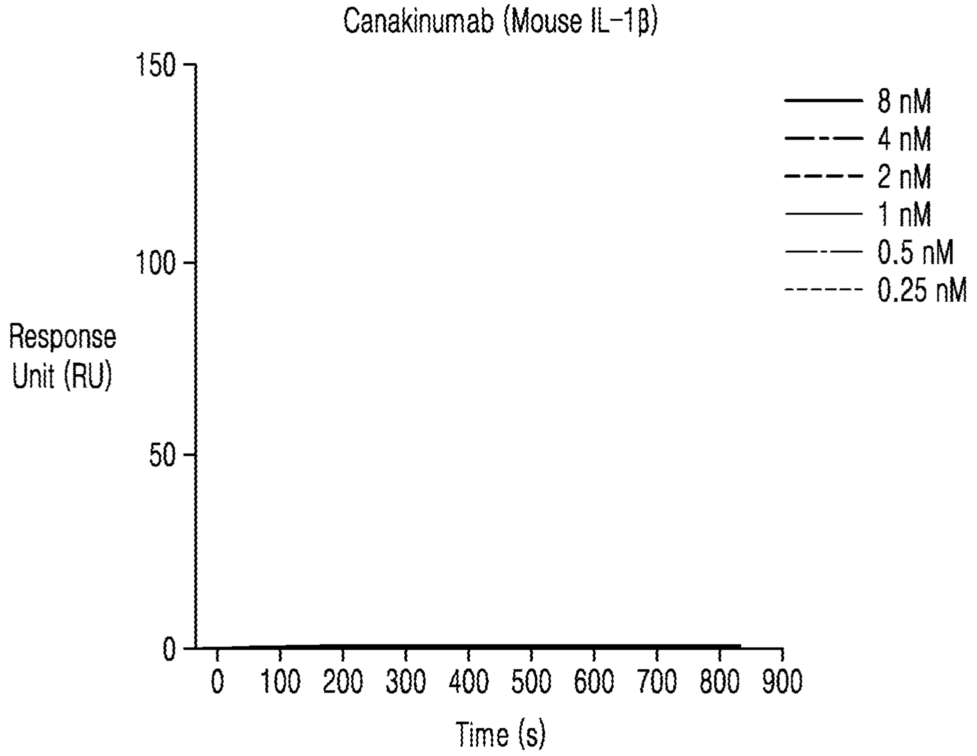

An analysis of binding of three types of IL-1 specific Fc fusion proteins (rilonacept, IL1T, PET101) to human IL-1β was performed by using an ELISA method. For comparison of binding capacity, human IL-1β antibody canakinumab was used as a control. A 96-half-well plate for immunosorbent assay (Corning, 3690) was treated with human IL-1β (Sino Biological, 10139-HNAE) at a concentration of 30 ng/well and coated overnight at 4° C. Next day, the plate was washed with Phosphate Buffered Saline with Tween-20 (PBST; TEKNOVA, P1192). All washing procedures in this analysis were performed by using an AquaMax 2000 plate washer (Molecular Devices, 0310-5363). IL1T, PET101, rilonacept, and canakinumab were diluted in PBST containing 1% (w/v) skim milk to an appropriate concentration and treated in each well, binding was induced at room temperature for 1 hour, and plate was washed 3 times. Thereafter, peroxidase-bound anti-human IgG Fc goat antibodies (Invitrogen 31413) were diluted (1:10,000) in PBST containing 1% (w/v) skim milk to induce binding, and washed 3 times with PBST, and then color reaction was induced by treating 3,3',5,5'-tetramethylbenzidine (TMB) substrate solution (Thermo Fisher Scientific, 34028) in the dark at room temperature. Thereafter, the reaction was terminated by treatment with 1N of sulfuric acid (DUKSAN, 255), and absorbance was measured at 450 nm by using a SpctraMax i3 multimode plate reader (Molecular Devices, 10192-220). PET101 was confirmed to bind to IL1T, rilonacept, and human IL-1β exhibiting similar $EC_{50}$ values (FIG. 6). When treated with the same molar concentration, canakinumab shows a higher $OD_{450}$ value, which is likely due to the avidity effect of canakinumab, a bivalent antibody (FIG. 6). The results of this experiment suggest that the $C_{L\kappa}$ and $C_{L\lambda}$ regions introduced between the human IL-1 receptor and the N-terminus of the Fc hinge region do not affect the binding between the human IL-1 receptor and human IL-1β.

Experimental Example 3: Measurement of Binding Constant Through Surface Plasmon Resonance (SPR)

In order to analyze binding capacity of PET101 to IL-1α and IL-1β more quantitatively, surface plasmon resonance analysis was performed by using Biacore T200 (GE healthcare). A Series S CM5 Sensor Chip (GE healthcare, BR100530) was used to measure the binding constant, and the anti-human Fc antibodies included in the Human Antibody Capture Kit (GE healthcare, BR100839) were immobilized to the sensor chip according to the manufacturer's manual by using an amine coupling kit (GE healthcare, BR100050). Flow cell 1 of the CM5 sensor, to which anti-human Fc antibodies were immobilized, was used as a blank space, and in Flow cells 2, 3, and 4, 100 nM of PET101 (18 μg/ml), 100 nM of rilonacept (25 μg/ml), and 100 nM of canakinumab (15 μg/ml) were respectively loaded for 1 minute at a flow rate of 10 μl/min. After preparation of all the flow cells, 0.25 nM, 0.5 nM, 1 nM, 2 nM, 4 nM, and 8 nM of human IL-1α (R&D systems, 200-LA), human IL-1β (R&D systems, 201-LB), and mouse IL-1α (R&D systems, 400-ML), mouse IL-1β (R&D systems, 401-ML), and rhesus monkey (Rhesus macaque) IL-1β (R&D systems, 1318-RL) antigens were injected at a flow rate of 30 μl/min, to carry out a binding reaction for 4 minutes, subsequently, only 1×HBS-EP+ buffer (GE healthcare, BR100669) was injected at a flow rate of 30 μl/min to perform a dissociation reaction for 10 minutes. Affinity was calculated by performing normalization and subtraction in each acquired sensorgram comparing with the blank cell. The BIAevaluation software (GE healthcare) was used for affinity calculation, and the association rate constant and dissociation rate constant were calculated through the 1:1 Langmuir model analysis. An equilibrium dissociation constant ($K_D$) is a value obtained by dividing the dissociation rate constant ($K_d$) by the association rate constant ($K_a$). It was confirmed that PET101 has $K_D$ values of high levels of 6.97 pM, 3.46 pM, and 1.43 for human IL-1α, human IL-1β, and monkey IL-1β, respectively, and $K_D$ values of 19.42 PM and 304.54 PM for mouse IL-1α and mouse IL-1β, respectively (FIGS. 7A, 7B, 7C, 7D, and 7E, Table 1). Rilonacept showed a similar binding pattern to PET101, and the measured binding constants are shown in Table 1 (FIGS. 7F, 7G, 7H, 7I, and 7J). It was confirmed that the human IL-1β-specific antibody canakinumab had a $K_D$ value of 68.39 PM for human IL-1β, did not bind to human IL-1α, and had no cross-species binding capacity to a mouse antigen (FIGS. 7K, 7L, 7M, 7N, and 7O, Table 1). The measured $K_D$ value of canakinumab for rhesus monkey IL-1β was 2.847 UM, and canakinumab showed a rapidly dissociating pattern, and was analyzed to have a very low binding capacity (FIGS. 7K, 7L, 7M, 7N, and 7O, Table 1).

TABLE 1

Equilibrium dissociation constant ($K_D$), association rate constant ($K_a$), and dissociation rate constant ($K_d$) of PET101, rilonacept, and canakinumab for human IL-1α, human IL-1β, monkey IL-1β, mouse IL-1α, and human IL-1β

| | PET101 | | | Rilonacept | | | Canakinumab | | |
|---|---|---|---|---|---|---|---|---|---|
| | $K_a$(1/Ms)[1)] | $K_d$(1/s)[2)] | $K_D$(pM)[3)] | $K_a$(1/Ms)[1)] | $K_d$(1/s)[2)] | $K_D$(pM)[3)] | $K_a$(1/Ms)[1)] | $K_d$(1/s)[2)] | $K_D$(pM)[3)] |
| Human IL-1α | 6.32E+6 | 4.40E−5 | 6.97 | 9.18E+6 | 4.505E−5 | 4.91 | ND[4)] | ND[4)] | NB[5)] |
| Human IL-1β | 2.13E+7 | 7.38E−5 | 3.46 | 3.39E+7 | 8.669E−5 | 2.56 | 7.62E+5 | 5.21E−5 | 68.39 |
| Monkey IL-1β | 4.02E+7 | 7.75E−5 | 1.43 | 1.36E+7 | 2.430E−5 | 1.78 | 6.35E+3 | 1.81E−2 | 2847244 |
| Mouse IL-1α | 4.36E+6 | 8.47E−5 | 19.42 | 4.66E+6 | 1.784E−4 | 38.28 | ND[4)] | ND[4)] | NB[5)] |
| Mouse IL-1β | 5.36E+5 | 1.62E−4 | 304.54 | 8.90E+5 | 3.28E−4 | 368.54 | ND[4)] | ND[4)] | NB[5)] |

[1)]$K_a$: Association constant
[2)]$K_d$: Dissociation constant
[3)]$K_D$: Equilibrium dissociation constant
[4)]ND: Not determined
[5)]NB: No binding

Figure 8:
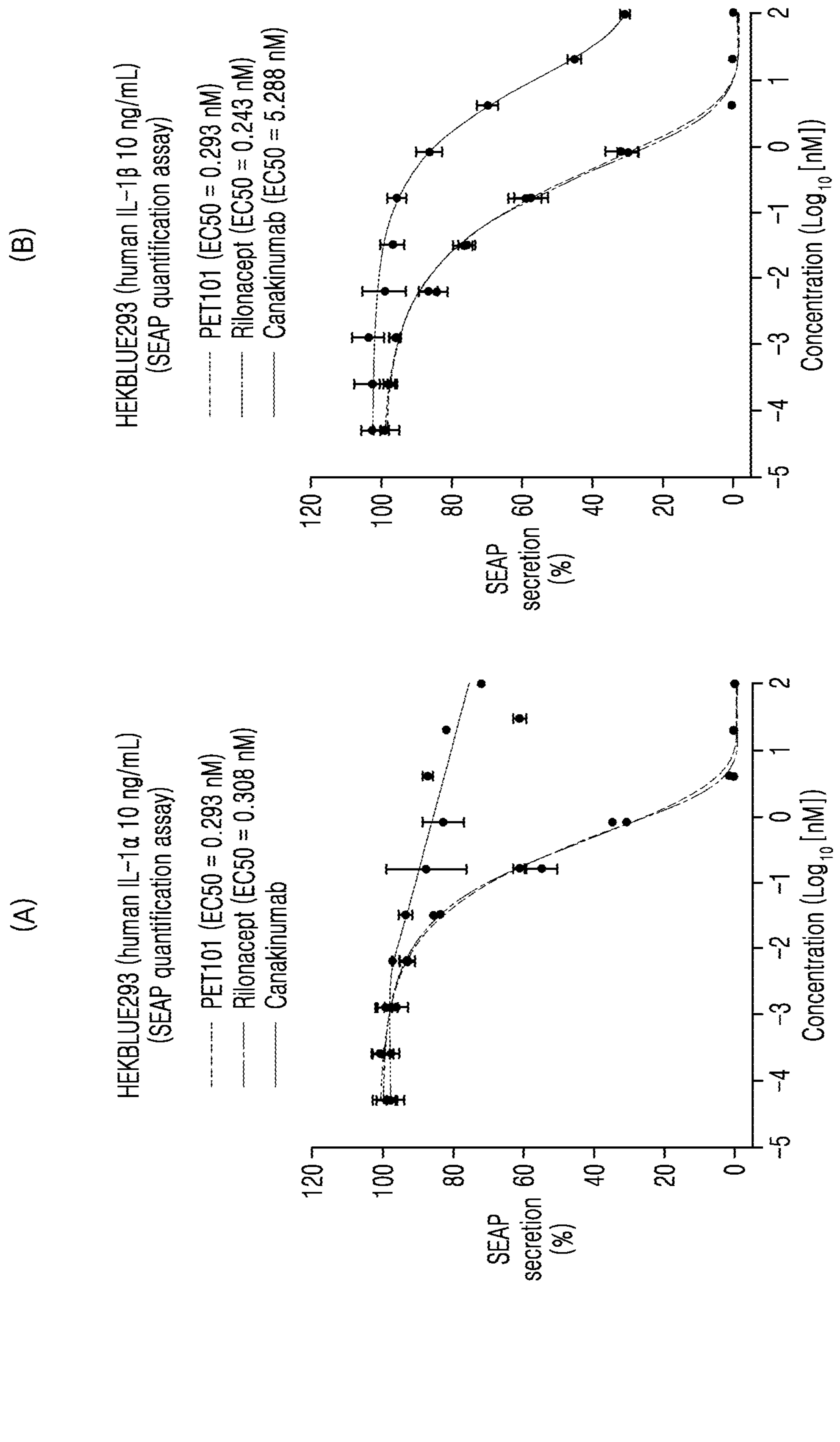
FIG. 8 shows results of analyzing IL-1α signaling pathway inhibitory ability (A) and IL-1β signaling pathway inhibitory ability (B) of PET101, rilonacept, and canakinumab in an IL-1 reporter cell line.

Experimental Example 4: Evaluation of Inhibitory Ability on IL-1 Signaling Pathway by Using a Reporter Cell Line An IL-1β reporter HEK 293 cell line (Invivogen, hkb-il1b) secretes secreted embryonic alkaline phosphatase (SEAP), a secreted reporter protein, in a concentration-dependent manner by human IL-1α and IL-1β. In the cell line, IL-1 and IL-1 inhibitors were simultaneously treated, and inhibitory ability on the signaling pathway was measured by quantifying the SEAP in the culture medium. The IL-1β reporter HEK 293 cell line was cultured in Dulbecco's Modified Eagle Medium (DMEM) (Gibco, 11965-092)+10% fetal bovine serum (FBS) (Gibco, 16140-071) medium. Cells were plated in a 96-well plate (Thermo Fisher Scientific, 167008) in complete culture medium at $1\times10^4$ cells/well, and cultured overnight at 37° C. in a 5% (v/v) $CO_2$ humidified incubator. 20 ng/ml of human IL-1α (Sino Biological, 10128-HNCH), or human IL-1β (Sino Biological, 10139-HNAE) dissolved in serum-free DMEM, and 0.0001024 nM, 0.000512 nM, 0.00256 nM 0.0128 nM, 0.064 nM, 0.32 nM, 1.6 nM, 8 nM, 40 nM, and 200 nM of an IL-1 inhibitor (PET101, rilonacept, or canakinumab) dissolved in serum-free DMEM were pre-mixed at a ratio of 1:1 for 30 minutes. In this case, human IL-1α or human IL-1β of the final concentration of 10 ng/ml, and 0.0000512 nM, 0.000256 nM, 0.00128 nM, 0.0064 nM, 0.032 nM, 0.16 nM, 0.8 nM, 4 nM, 20 nM, and 100 nM of an IL-1 inhibitor (PET101, rilonacept, or canakinumab) were present in a mixed form, and the culture solution of the cell culture plate prepared previously through overnight culture was absorbed, and the pre-mixed medium was treated to the cells to be 100 μl per well, and then the samples were incubated for 5 hours, at 37° C., in a 5% (v/v) $CO_2$ humidified incubator. The supernatant was analyzed by using a SEAP reporter gene analysis kit (Invitrogen, T1017), and the inhibitory ability of IL-1 inhibitors on the IL-1β signaling pathway was determined. All values were calculated by converting the average value of the luminescence values measured by treating only 10 ng/ml of human IL-1α or human IL-1β to 100% SEAP secretion, and converting the average value of the luminescence values measured by treating PBS (Gibco, 10010) of the same volume with the treated substances to 0% SEAP secretion. As a result of the analysis of IL-1α inhibitory ability in the IL-1β reporter HEK 293 cell line, it was confirmed that PET101 had an $EC_{50}$ value of 0.293 nM, and rilonacept had an $EC_{50}$ value of 0.308 nM (A of FIG. 8). In this case, canakinumab did not induce effective inhibition (A of FIG. 8). As a result of the analysis of human IL-1β inhibitory ability in the same cell line, it was confirmed that PET101 had an $EC_{50}$ value of 0.275 nM, and rilonacept had an $EC_{50}$ value of 0.243 nM (B of FIG. 8). When 4 nM of PET101 or rilonacept was treated, about 99.5% of inhibition of SEAP secretion was confirmed in the reporter cell line, but only about 30% of inhibition of SEAP secretion was confirmed when 4 nM of canakinumab was treated (B of FIG. 8).

Figure 9:
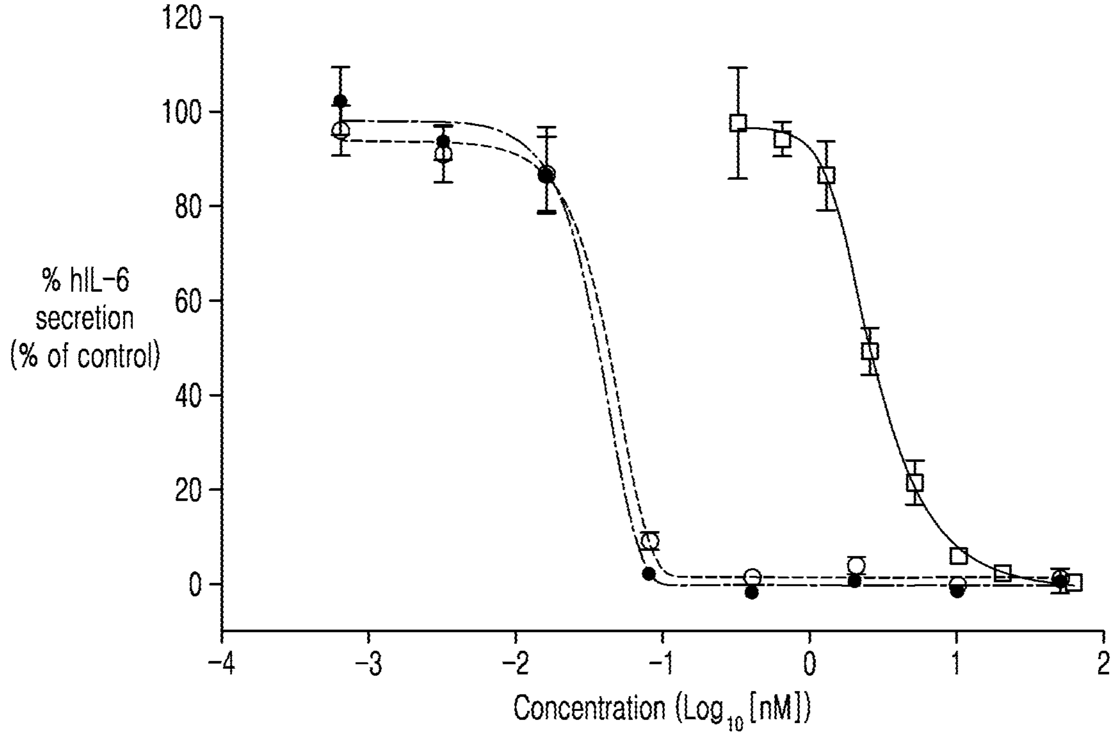
FIG. 9 shows results of analyzing IL-1β-mediated IL-6 secretion inhibitory ability of PET101, rilonacept, and canakinumab in an A549 non-small cell lung cancer cell line.

Experimental Example 5: Evaluation of Inhibitory Ability on IL-1 Signaling Pathway by Using A549 Non-Small Cell Lung Cancer Cell Line An A549 non-small cell lung cancer cell line shows responsiveness to IL-1β, and induces secretion of Interleukin-6 (IL-6) by activating phosphoinositide 3-kinase (PI3K), and interleukin-1 receptor-associated kinase 4 (IRAK4) (Hiroyuki Eda et al. Cell Biol Int. 2011). Using this mechanism, the efficacy of PET101 was evaluated in a human lung cancer cell line rather than an artificially prepared reporter cell line. The A549 non-small cell lung cancer cell line (ATCC, CCL-185) was cultured in RPMI-1640 (Welgene, LM001-03)+10% FBS (Gibco, 16140-071) medium. The cells were plated in a 96-well plate in complete serum medium as above at $2\times10^5$ cells/well, and then cultured for 7 hours at 37° C. in a 5% (v/v) $CO_2$ humidified incubator, to induce cell adhesion. Subsequently, the medium was removed from the wells, 100 μl of serum-free RPMI-1640 medium (Welgene, LM001-03) was added, and the cells were fasted for 18 hours at 37° C. in a 5% (v/v) $CO_2$ humidified incubator. 100 μl of IL-1β (Sino Biological, 10139-HNAE) of the final concentration of 1 ng/ml, and an IL-1 inhibitor (PET101, rilonacept, or canakinumab) of an appropriate concentration, pre-mixed in serum-free RPMI-1640 medium for 30 minutes was treated to each well. Three hours after the treatment, an amount of IL-6 in the supernatant was quantified by using the Mouse IL-6 DuoSet ELISA kit (R&D systems, DY406) according to the manufacturer's manual. As a result of evaluating IL-1β inhibitory ability of the A549 cell line through the IL-6 quantification, PET101 was confirmed to have an $EC_{50}$ value of 44 pM, and rilonacept was confirmed to have a similar $EC_{50}$ value of 37 pM. Canakinumab was confirmed to have an $EC_{50}$ value of 2,678 pM under the same conditions (FIG. 9).

Experimental Example 6: Analysis of Thermal Stability of PET101

Figure 10:
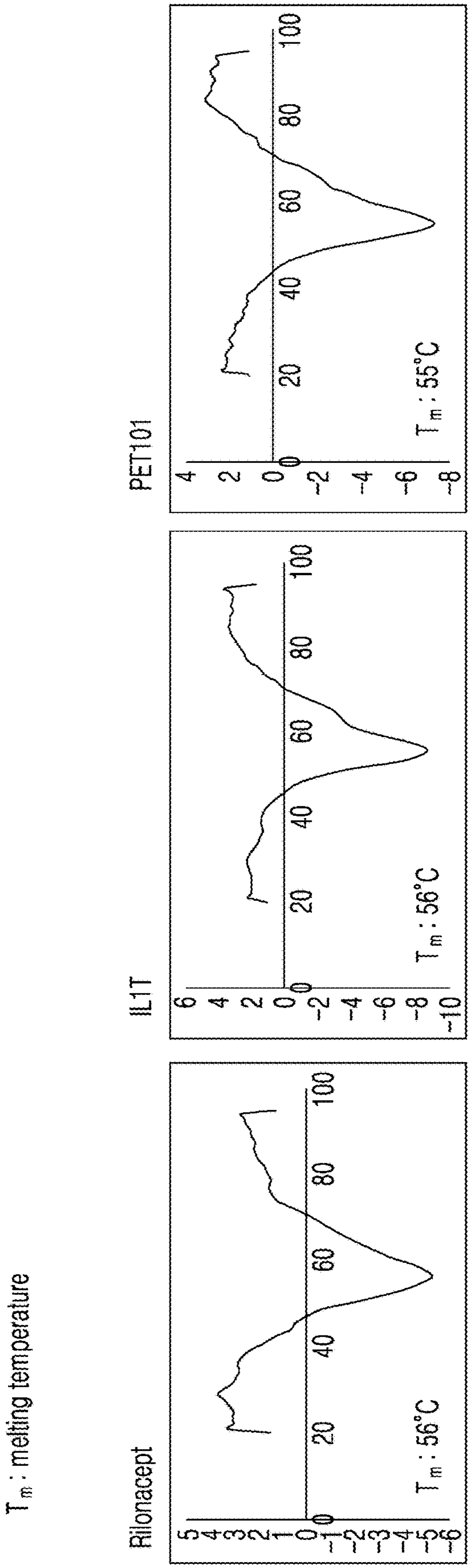
FIG. 10 shows results of analyzing protein thermal stability of rilonacept, IL1T, and PET101.

Analysis of thermal stability of PET101 was performed by using a Protein Thermal Shift™ Dye Kit (Applied biosystems, 4461146) according to the manufacturer's manual. As a result of the measurement, it was confirmed that rilonacept, IL1T, and PET101 had similar $T_m$ values of 56° C., 56° C., and 55° C., respectively (FIG. 10).

Experimental Example 7: Analysis of Stability of PET101 at 37° C.

Figure 11A:
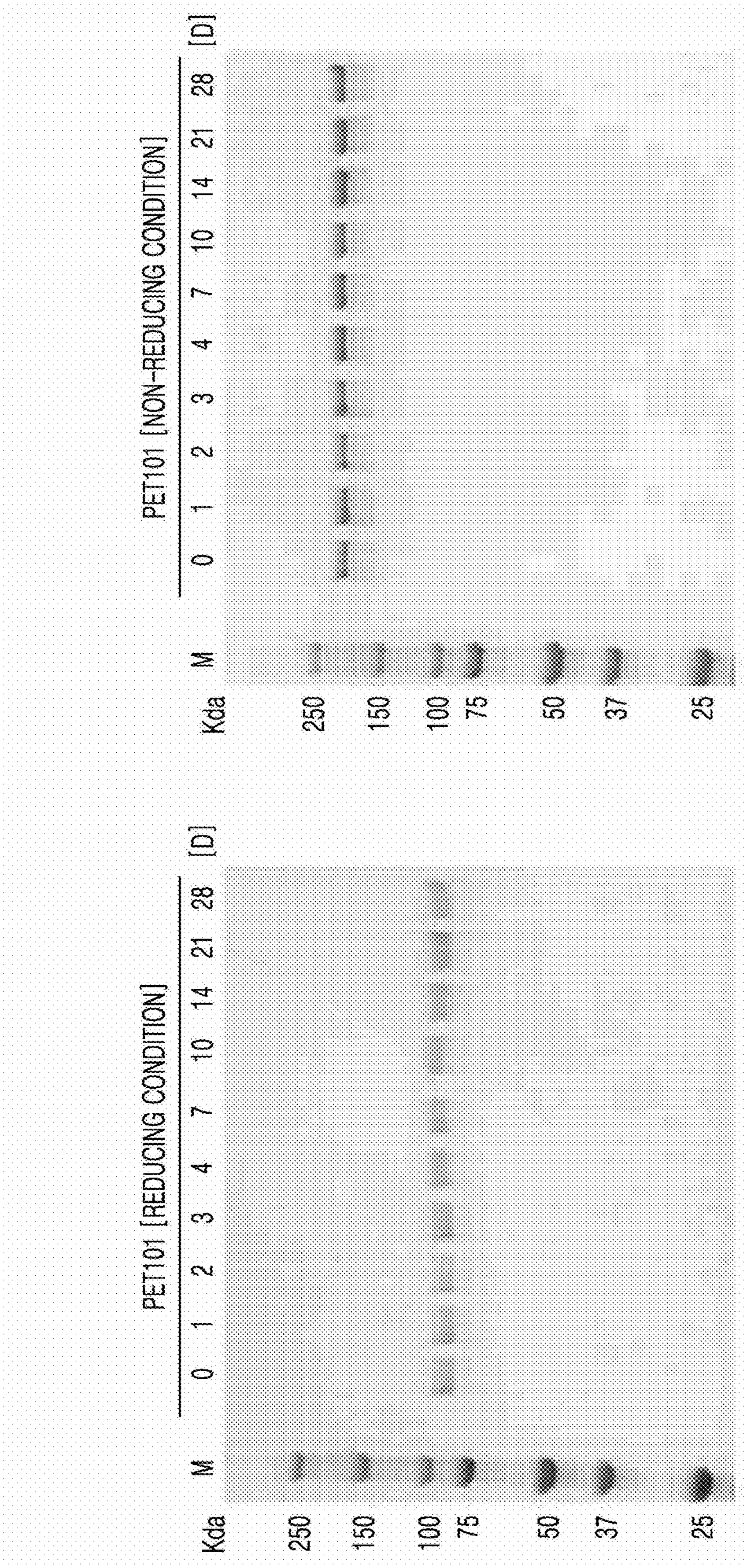
FIGS. 11A and 11B show results of analyzing stability of PET101 in phosphate-buffered saline (PBS) at 37° C. for 4 weeks by using SDS-PAGE (A), and size exclusion chromatography (B), respectively.
Figure 11B:
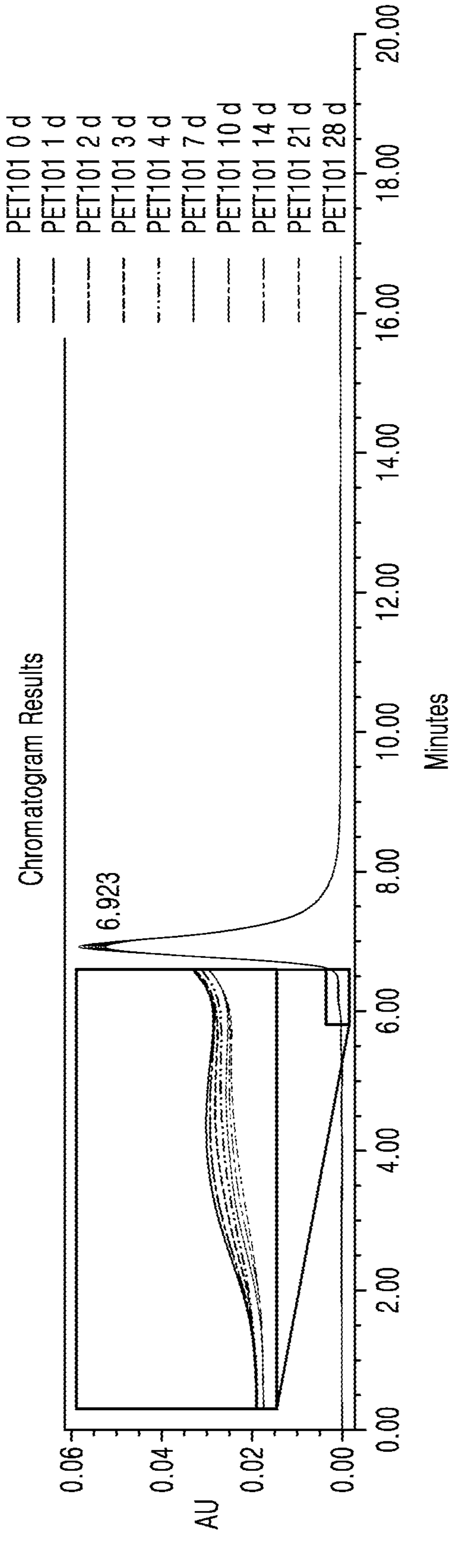
Figure 12A:
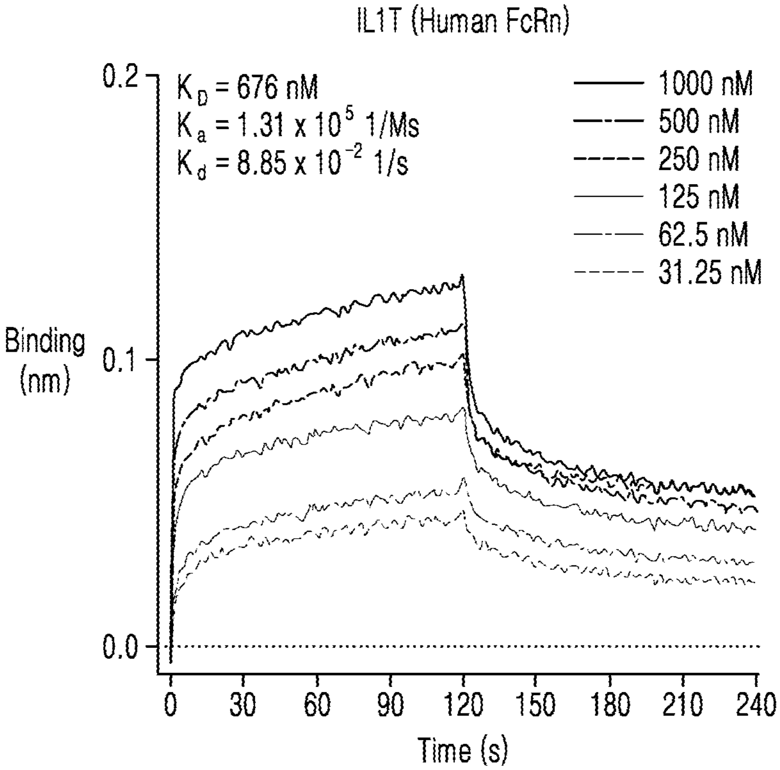
FIGS. 12A, 12B, 12C, and 12D show results of bio-layer interferometry (BLI) sensogram of IL1T, PET101, rilonacept, and canakinumab for human FcRn, respectively.
Figure 12B:
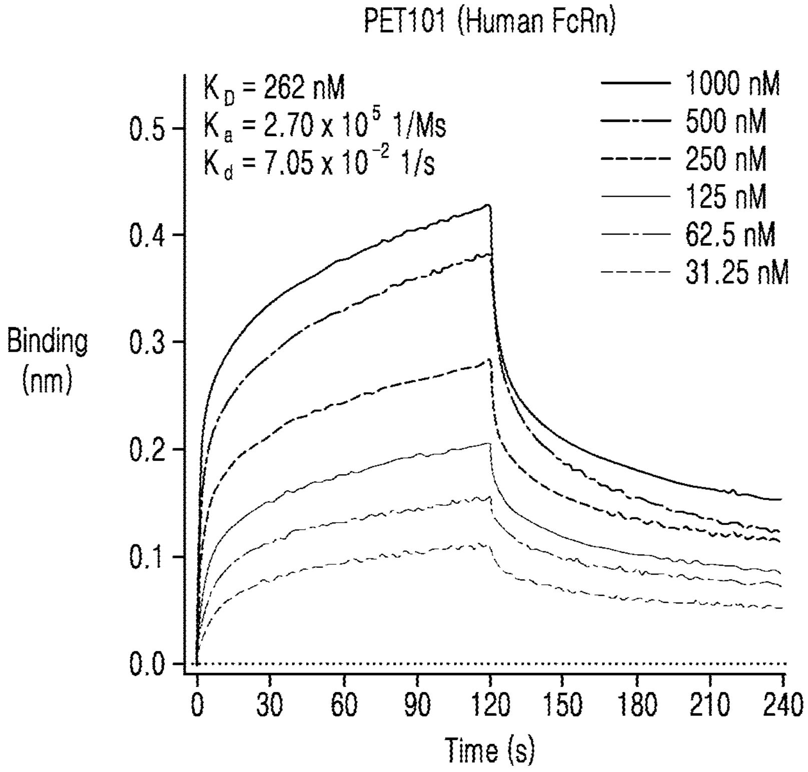
Figure 12C:
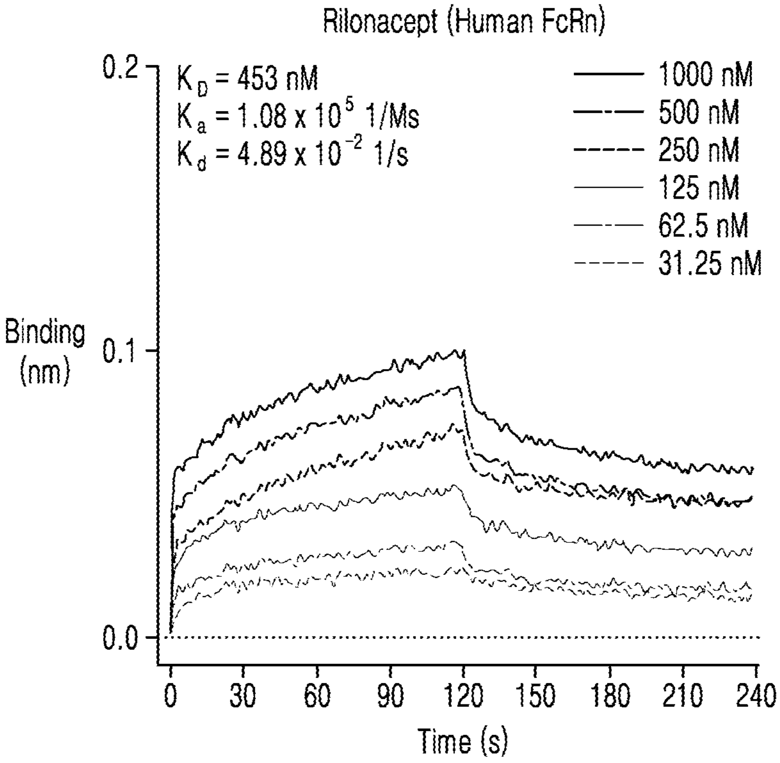
Figure 12D:
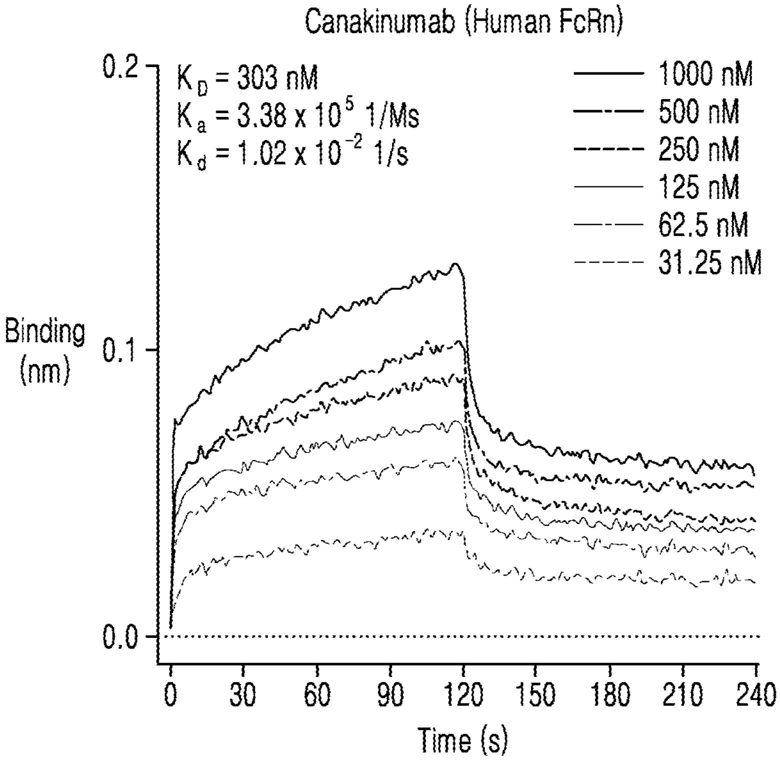

Stability analysis of PET101 dissolved in PBS (pH 7.4; Gibco, 10010) was performed at 37° C. 1 mg/ml of PET101 was incubated at 37° C., and on days 0, 1, 2, 3, 4, 7, 10, 14, 21, and 28, the sample was transferred to −80° C., and SDS-PAGE analysis was performed in the manner described in Example 1 (FIG. 11A). Fragmentation and aggregation were not identified in the results of the analysis under reducing and non-reducing conditions. As a result of analyzing the presence or absence of aggregates using size exclusion chromatography, a peak of aggregates was confirmed at a retention time of about 6.2 minutes, and a very low peak was detected in the sample until the 7th day at 37° C. (FIG. 11B), and the area could not be measured in the area analysis by using the Empower software (Waters) (Table 2). In the sample at day 10 at 37° C., 99.12% of PET101 was present and 0.88% of aggregates were confirmed (Table 2). In the sample at day 28 at 37° C., 98.85% of PET101 was present and 1.15% of aggregates were confirmed (Table 2).

TABLE 2

Analysis of amounts of aggregates according to incubation time at 37° C. in PBS by using size exclusion chromatography

| Time (day) | Sample | Retention time (minutes) | Height (μV) | Area | Area (%) |
|---|---|---|---|---|---|
| 0 | PET101 | 6.923 | 51721 | 1389703 | 100 |
| | Aggregate | Not detected | 0 | 0 | 0 |
| 1 | PET101 | 6.916 | 57457 | 1473261 | 100 |
| | Aggregate | Not detected | 0 | 0 | 0 |
| 2 | PET101 | 6.920 | 57212 | 1466081 | 100 |
| | Aggregate | Not detected | 0 | 0 | 0 |
| 3 | PET101 | 6.918 | 57264 | 1463598 | 100 |
| | Aggregate | Not detected | 0 | 0 | 0 |
| 4 | PET101 | 6.926 | 55570 | 1429275 | 100 |
| | Aggregate | Not detected | 0 | 0 | 0 |
| 7 | PET101 | 6.912 | 57433 | 1473833 | 100 |
| | Aggregate | Not detected | 0 | 0 | 0 |
| 10 | PET101 | 6.910 | 57614 | 1495529 | 99.12 |
| | Aggregate | 6.241 | 570 | 13283 | 0.88 |
| 14 | PET101 | 6.910 | 56284 | 1483131 | 99.03 |
| | Aggregate | 6.259 | 613 | 14520 | 0.97 |
| 21 | PET101 | 6.907 | 56942 | 1484995 | 98.95 |
| | Aggregate | 6.211 | 671 | 15762 | 1.05 |
| 28 | PET101 | 6.908 | 56049 | 1482170 | 98.85 |
| | Aggregate | 6.222 | 709 | 17316 | 1.15 |

Experimental Example 8: Evaluation of the FcRn Binding Capacity of PET101

The evaluation of the binding capacity of PET101 and rilonacept to FcRn was performed by analyzing at 30° C. by using Octet Red96e (Fortebio), a Bio-Layer Interferometry (BLI) analysis equipment. Anti-Penta-HIS (HIS1K) biosensor (Fortebio, 18-5120) was used, for an analysis buffer, 10× Kinetics Buffer (ForteBio, 18-1042) were mixed with pH 7.4 PBS (Gibco, 10010) at 1:9, to prepare a buffer having the final pH of 6.0, and the buffer was used as a running buffer. Rotation speed of the analysis plate was 1,000 rpm under all conditions. Human FcRn (Acrobiosystems, FCM-H82W4) containing His tag was diluted in the running buffer to a concentration of 2 μg/ml, and loaded onto the biosensor. Binding reactions of 31.25 nM to 1,000 nM of IL1T, PET101, rilonacept, or canakinumab were carried out for 120 seconds to measure the association rate constant ($K_a$), and then dissociation reactions were carried out in the running buffer for 120 seconds to determine the dissociation rate constant ($K_d$). The values of $K_a$ (0 sec to 120 sec) and $K_d$ (120 sec to 125 sec) were calculated through a 1:1 binding model in the Octet analysis software (Fortebio), and the equilibrium dissociation constant ($K_D$) value was determined based on these. (FIGS. 12A, 12B, 12C, and 12D).

Figure 13A:
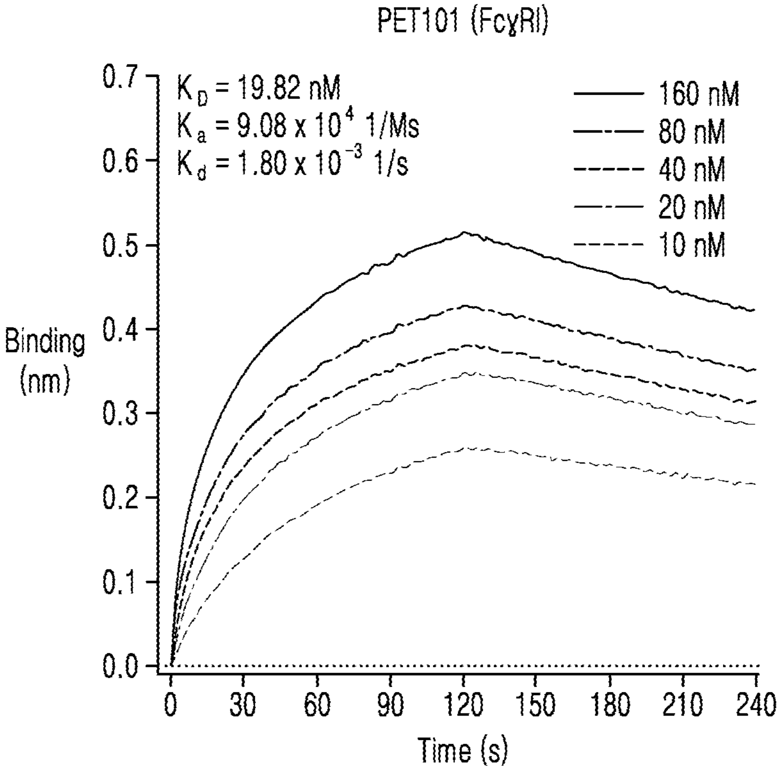
FIGS. 13A and 13B show results of BLI sensorgram of PET101 and rilonacept for human FcγRI, respectively.
Figure 13B:
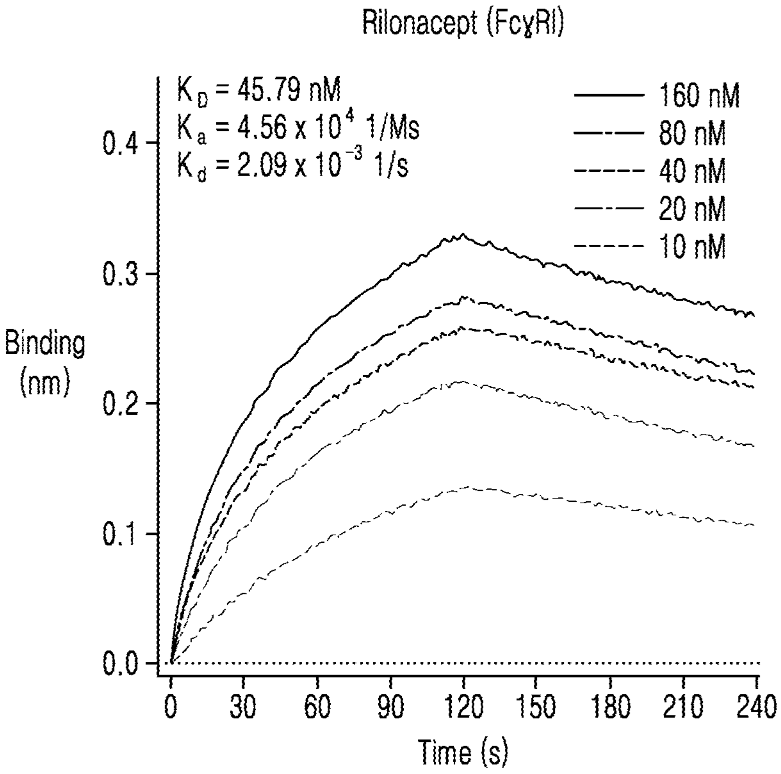
Figure 13C:
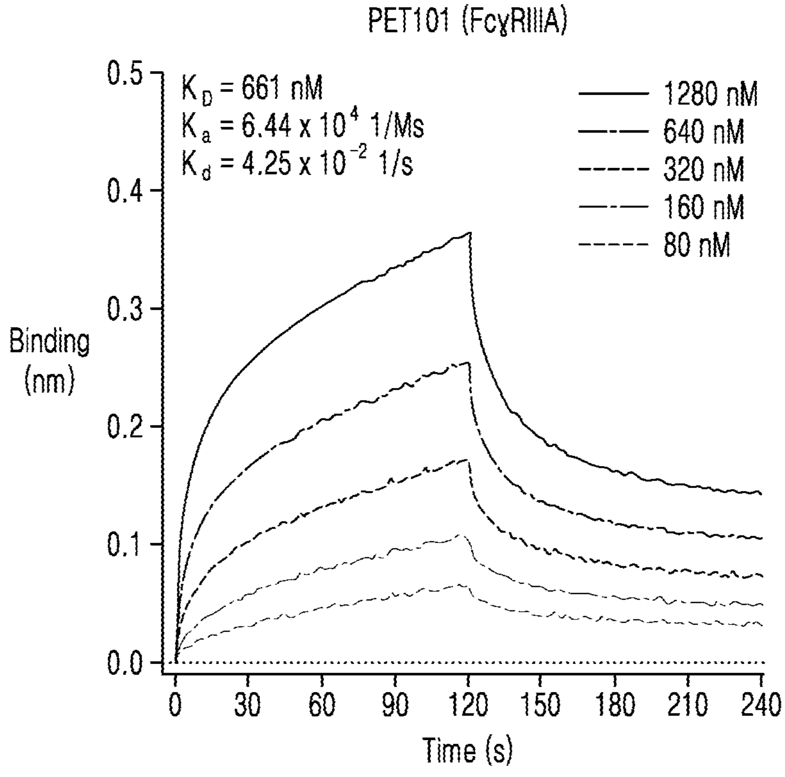
FIGS. 13C and 13D show results of BLI sensorgram of PET101 and rilonacept for human FcγRIIIA, respectively.
Figure 13D:
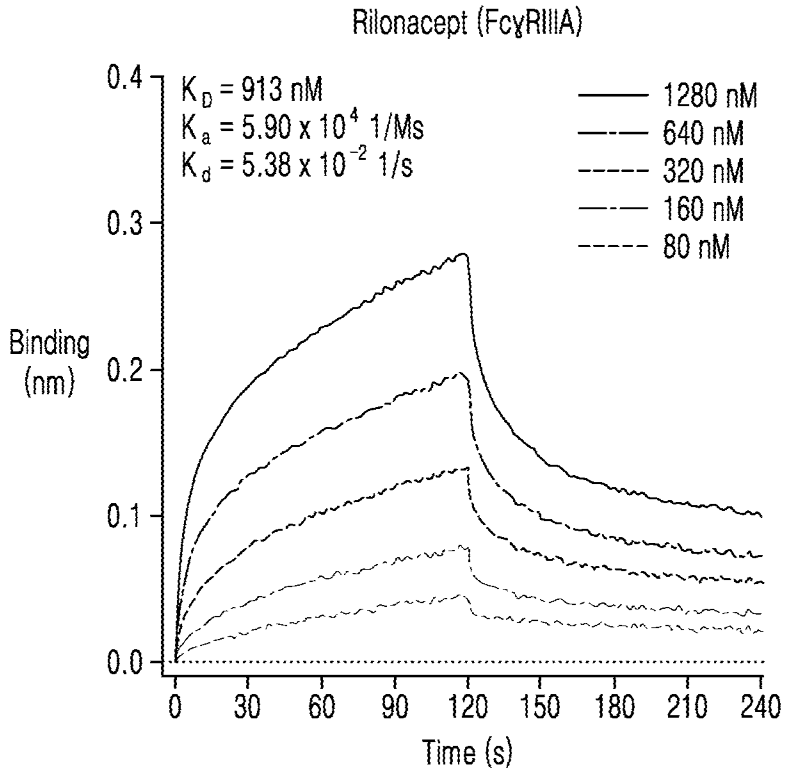

Experimental Example 9: Evaluation of Binding Capacity of PET101 to Fc Gamma Receptors Binding capacity of PET101 to Fc gamma receptors was analyzed at 30° C. by using Octet Red96e (Fortebio), a bio-layer interferometry (BLI) analysis equipment. Anti-Penta-HIS (HIS1K) biosensor (Fortebio, 18-5120) was used, for an analysis buffer, 10× Kinetics Buffer (ForteBio, 18-1042) was prepared as a running buffer by diluting in pH 7.4 PBS (Gibco, 10010) and used, and rotation speed of the analysis plate was 1,000 rpm. Human FcγRI (R&D systems, 1257-FC) or human FcγRIIIA (R&D systems, 4325-FC) containing His tag was diluted in the running buffer to a concentration of 2 μg/ml and loaded into the biosensor. In order to measure the association rate constant ($K_a$), binding reactions of 80 nM to 1,280 nM of PET101 or rilonacept were carried out for 120 seconds, followed by dissociation in the running buffer for 120 seconds to determine the dissociation rate constant ($K_d$). $K_D$ for FcγRI was calculated through a 1:1 binding model in the Octet analysis software (Fortebio), and in this analysis, the sections where curve fitting was performed were $K_a$ (0 sec to 120 sec) and $K_d$ (120 sec to 240 sec). In this case, the $K_D$ values of PET101 and rilonacept for FcγRI were confirmed to be 19.82 nM, and 45.79 nM, respectively (FIGS. 13A and 13B). $K_D$ for FcγRIIIA was calculated through a 1:1 binding model in the Octet analysis software (Fortebio), and in this analysis, the sections where curve fitting was performed were $K_a$ (0 sec to 120 sec) and $K_d$ (120 sec to 125 sec). In this case, the $K_D$ values of PET101 and rilonacept for FcγRI were confirmed to be 661 nM, and 913 nM, respectively (FIGS. 13C and 13D).

Experimental Example 10: Evaluation of In Vivo Neutralizing Ability According to Administered Concentration of PET101

Figure 14:
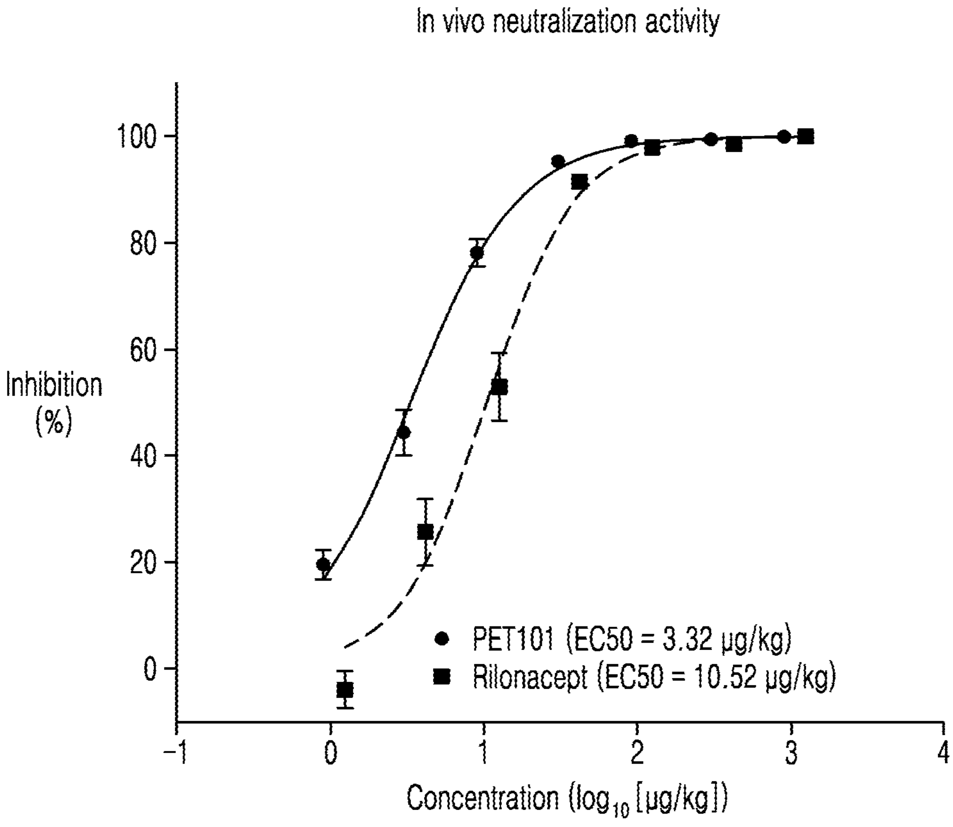
FIG. 14 shows results of analyzing human IL-1β-mediated mouse IL-6 secretion inhibitory ability according to administered concentration of PET101 and rilonacept.

For an experiment evaluating in vivo neutralizing ability of PET101 (n=5/group) according to its concentration, 6-week-old C57BL/6 females about 20 g per each were used. All experimental procedures related to an animal experiment were conducted under the approval of the Medytox Institutional Animal Care and Use Committee (IACUC) prior to initiation. Evaluation of in vivo neutralizing ability of PET101 was performed by using a method established in a previous literature, and used the phenomenon that IL-6 in the mouse blood increases when human or monkey IL-1 or IL-1β is administered to C57BL/6 female mice. (Economides et al., Nat Med. 2003 & Lacy et al. mAbs. 2015). Specifically, after artificially injecting exogenous human IL-1β into mice, an ability of PET101 to inhibit the increase of IL-6 was compared with that of rilonacept. First, 0.001 mg/kg (0.3 times), 0.003 mg/kg (1 times), 0.01 mg/kg (3 times), 0.03 mg/kg (10 times), 0.1 mg/kg (30 times), 0.3 mg/kg (100 times), and 1 mg/kg (300 times) of PET101 or 0.0014 mg/kg (0.3 times), 0.0047 mg/kg (1 times), 0.14 mg/kg (3 times), 0.465 mg/kg (10 times), 0.140 mg/kg (30 times), 0.465 mg/kg (100 times), and 1.40 mg/kg (300 times) of rilonacept was subcutaneously (s.c.) administered to mice (number in parentheses=moles of anti-IL-1 trap/moles of human IL-1β corresponding to 300 ng/kg to be administered later). 24 hours after the subcutaneous administration, human IL-1β (Sino Biological, 10139-HNAE) was administered at 300 ng/kg (5 ml/kg) by intraperitoneal (i.p.) administration. Serum from each mouse was obtained 2 hours after the administration. Quantification of IL-6 in the mouse serum was performed by using the Mouse IL-6 DuoSet ELISA kit (R&D systems, DY406). The quantified IL-6 value of the serum, obtained by subcutaneously administering PBS without administration of an anti-IL-1 trap, and subcutaneously administering the same amount of PBS after 24 hours, was calculated as 0%, and the quantified IL-6 value of the serum, obtained by subcutaneously administering the same amount of PBS without administration of an anti-IL-1 trap, and intraperitoneally administering 300 ng/kg (5 ml/kg) of IL-1β, was calculated as 100%. Based on this, a quantitative value of each group was converted to inhibitory ability (%). As a result of the analysis, the $EC_{50}$ value of PET101 was 3.32 ug/kg, and the $EC_{50}$ value of rilonacept was 10.52 μg/kg, confirming that PET101 had about 3.17 times superior activity compared to rilonacept (FIG. 14). When PET101 or rilonacept was excessively administered in a 3-fold (based on the mole number) compared to the administered IL-1β, PET101 showed an inhibitory activity of about 80%, whereas rilonacept showed an inhibitory activity of about 50% (FIG. 14).

Figure 15:
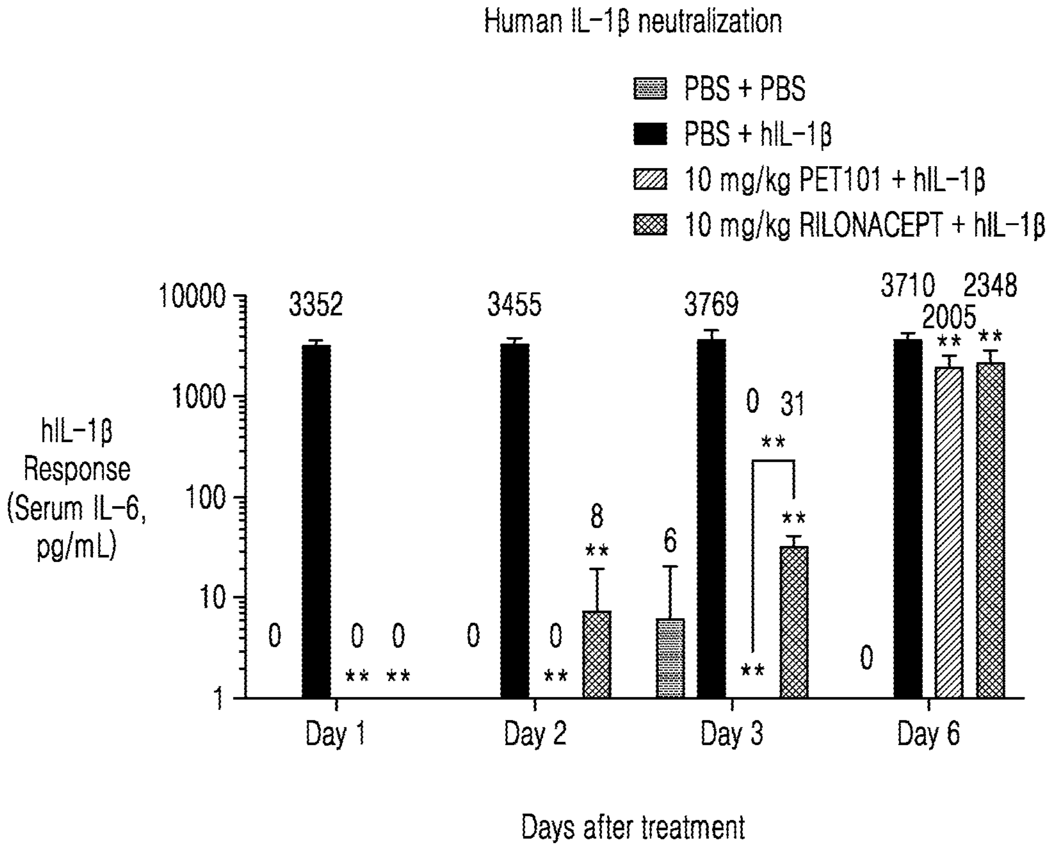
FIG. 15 shows results of analyzing human IL-1β-mediated mouse IL-6 secretion inhibitory ability according to time after administration of PET101 and rilonacept.

Experimental Example 11: Evaluation of In Vivo Neutralizing Ability of PET101 According to Administration Time For an experiment evaluating in vivo neutralizing ability of PET101 (n=5/group: total 16 groups) according to time, 6-week-old C57BL/6 females about 20 g per each were used. All experimental procedures related to an animal experiment were conducted under the approval of the Medytox Institutional Animal Care and Use Committee (IACUC) prior to initiation. The experiment was conducted in a way that after administering PET101 to mice, human IL-1β was artificially injected at various times, and amounts of IL-6 produced were quantified. Specifically, the ability of PET101 remaining on days 1, 2, 3, and 6 after the administration to inhibit IL-6 was compared and analyzed with that of rilonacept. First, PBS, and 10 mg/kg of PET101, or 10 mg/kg of rilonacept were subcutaneously (s.c.) administered to mice. 1, 2, 3, and 6 days after the subcutaneous administration, PBS or human IL-1β (Sino Biological, 10139-HNAE) was administered at 300 ng/kg (5 ml/kg) by intraperitoneal (i.p.) administration. Serum of each mouse was obtained 2 hours after the administration, and quantification of IL-6 in the mouse serum was performed in the manner described in Experimental Example 5 using the Mouse IL-6 DuoSet ELISA kit (R&D systems, DY406). As a result of the quantitative analysis, in the group administered with PBS (s.c.)+PBS (i.p.), 0 pg/ml to 6 pg/ml of mouse IL-6 was quantified regardless of time (FIG. 15). This indicates that IL-6 is absent or present in a trace amount in the blood of normal C57BL/6 female mice (FIG. 15). In the case of PBS (s.c.)+hIL-1β (i.p.) administration, the administered human IL-1β induced expression of mouse IL-6, and 3,352 pg/ml to 3,769 pg/ml of IL-6 was quantified. When PET101 was administered, IL-6 induction was completely inhibited until the 3rd day, and in the condition in which human IL-1β was treated 6 days after the PET101 administration, about 2,005 pg/ml of IL-6 was quantified (FIG. 15). In the case of the rilonacept-administered group, IL-6 induction was completely suppressed only on day 1, and on days 2, 3, and 6, 8 pg/ml, 31 pg/ml, and 2,348 pg/ml of IL-6 was measured in the blood (FIG. 15). Through this analysis, it was confirmed that PET101 is superior to rilonacept in terms of the durability of the efficacy of inhibiting human IL-1β in the mouse body (FIG. 15).

Figure 16:
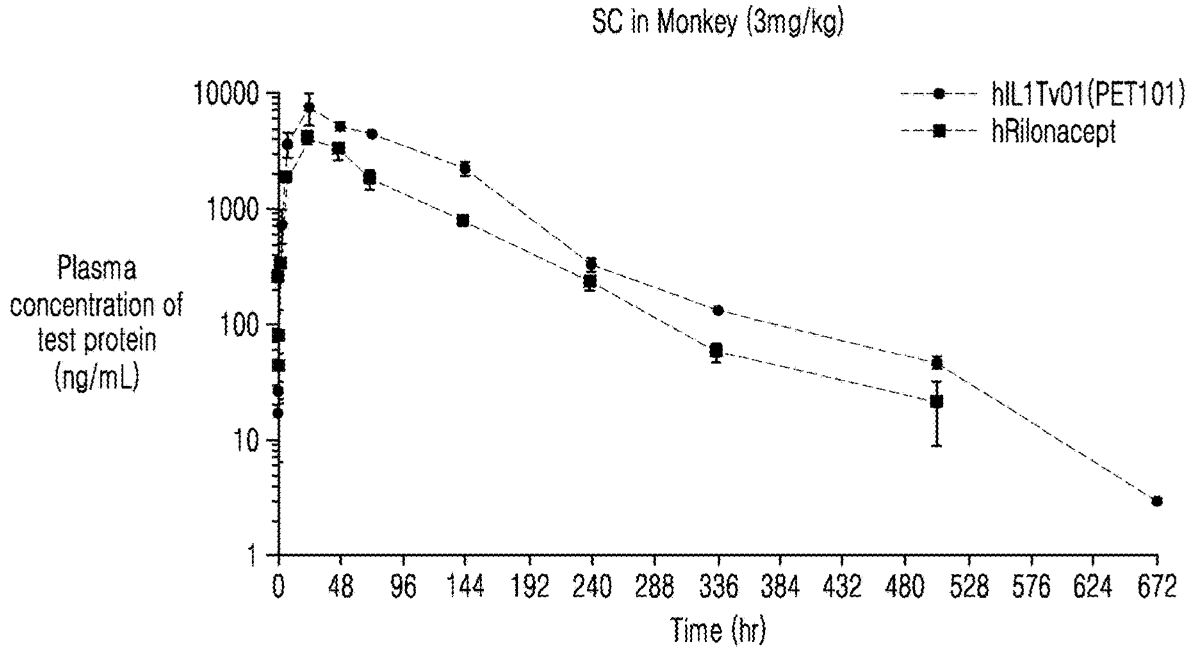
FIG. 16 shows results of analyzing plasma concentrations of test substances according to time in cynomolgus monkeys under the condition of subcutaneous administration of 3 mg/kg of PET101 and rilonacept.

Experimental Example 12: Primate Pharmacokinetics (PK) Analysis of PET101 Using Cynomolgus Monkeys PK analysis of PET101 was performed by using cynomolgus monkeys. Rilonacept was used as a control. 3 mg/kg of PET101 and rilonacept were administered by subcutaneous (s.c.) route of administration (n=3/group). Blood samples were obtained after 0 minute, 30 minutes, 1 hour, 2 hours, 4 hours, 8 hours, 1 day, 2 days, 3 days, 6 days, 10 days, 14 days, 21 days, and 28 days, and plasma separation was performed. Concentrations of PET101 and rilonacept in the plasma were measured by ELISA. Briefly, coating was performed by storing 1 μg/ml of high-affinity chimeric anti-human-IL-1R mouse antibodies in a 96-well plate for ELISA (Corning, 3590) overnight at 4° C., and the plate was washed with PBST the next day, blocking was performed by using a 3% bovine serum albumin (BSA) solution (Sigma) for 1 hour at room temperature, followed by washing with PBST. The plasma obtained at each time was appropriately diluted to induce a binding reaction to the coated anti-human-IL-1R rabbit antibodies. After washing with PBST, high affinity chimeric anti-human-IL-1RAcP rabbit antibodies were treated to induce a binding reaction at room temperature for 1 hour. Washing was performed by using PBST, and peroxidase-conjugated anti-rabbit IgG antibodies (Cell Signaling Technology, 7074S) were treated to induce binding at room temperature for 1 hour. The plate was washed three times by using PBST, treated with a TMB substrate solution (Thermo Fisher Scientific, 34028), and a reaction was induced in the dark at room temperature for 20 minutes. The reaction was terminated by treating 1N of sulfuric acid solution (DUKSAN, 255), and absorbance was measured at 450 nm by using a SpectraMax i3x multimode plate reader (Molecular Devices, i3x). Standard quantitative samples of PET101 and rilonacept were prepared and used for quantification, and concentration of the analyte at each time was quantified by using a standard curve generated from naive cynomolgus serum containing each concentration. When 3 mg/kg of PET101 and rilonacept were subcutaneously administrated, PET101 and rilonacept were confirmed to have half-lives ($T_{1/2}$) of similar levels of about 59.3 hours and about 62.5 hours, respectively (Table 3). However, the area under the curve from time 0 to infinity ($AUC_{inf}$) of PET101 was measured to be 2.17 times that of rilonacept, confirming its superiority in drug exposure in the body for monkeys (FIG. 16, Table 3).

TABLE 3

PK parameters of PET101 and rilonacept in cynomolgus monkeys

| Administered substance (dose, route of administration) | PET101 (3 mg/kg, s.c.) | Rilonacept (3 mg/kg, s.c.) |
|---|---|---|
| $T_{1/2}$(h) | 59.3 ± 0.7 | 62.5 ± 6.7 |
| $T_{max}$(h) | 24.0 ± 0.0 | 24.0 ± 0.0 |
| $C_{max}$(ng/ml) | 7576 ± 2325 | 3964 ± 316 |
| $AUC_{last}$(ng * h/ml) | 776430 ± 59152 | 356766 ± 6022 |
| $AUC_{inf}$(ng * h/ml) | 776681 ± 59146 | 358670 ± 5101 |
| $MRT_{inf}$(h) | 90.9 ± 5.0 | 86.4 ± 4.6 |

Comparative Example 2: Preparation of Heterodimeric Polypeptide (118T3) with Bi-Specificity for IL-1 and IL-18

Figure 17A:
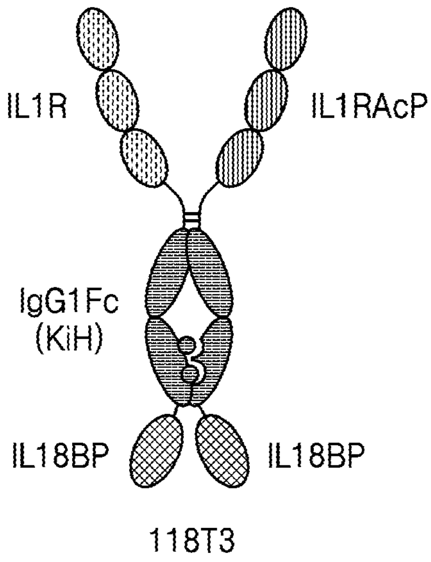
FIGS. 17A, 17B, 17C, and 17D show a schematic diagram of IL-1/IL-18 bi-specific heterodimer trap 118T3 (FIG. 17A), SDS-PAGE results of the purified products of 118T3 under reducing and non-reducing conditions (FIG. 17B), a schematic diagram of IL-1/IL-18 bi-specific κλ heterodimer trap 118T3v01 (FIG. 17C), and SDS-PAGE results of the purified products of 118T3v01 of each step in reducing and non-reducing conditions (FIG. 17D), respectively.
Figure 17B:
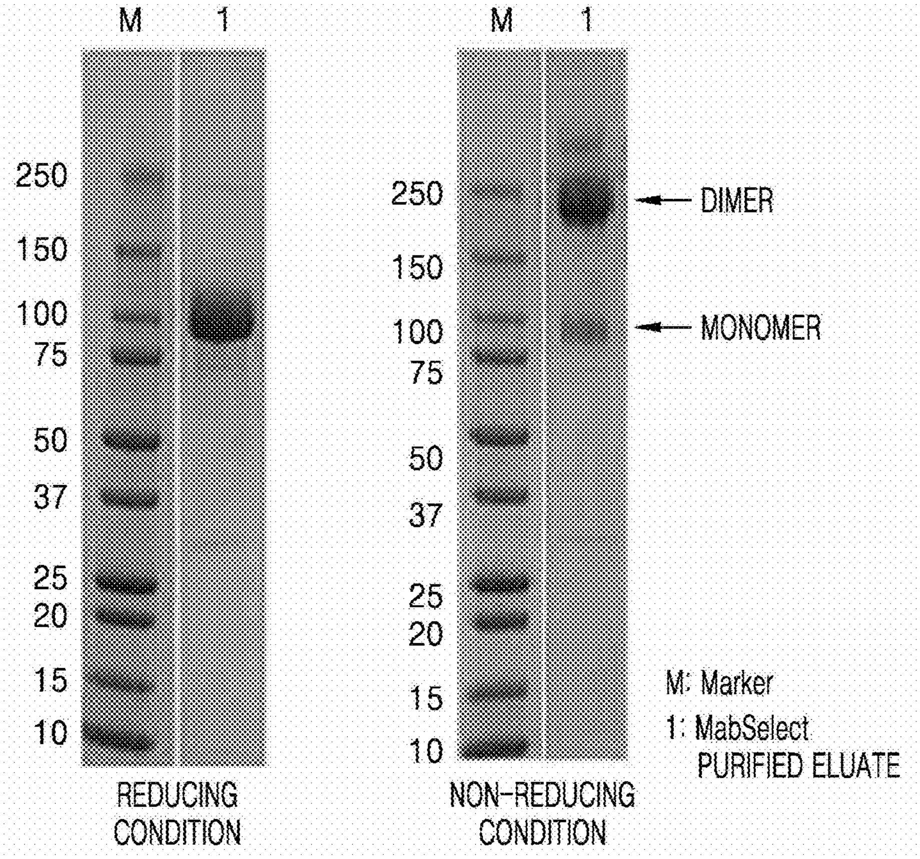

First, a heterodimer in which human IL18BP was fused to the C-terminus region of the Fc region of IL1T was prepared (FIG. 17A). Gene sequences of 31 to 194 amino acid residues constituting human IL18BP (GenBank: BAA76374.1) were chemically synthesized (Integrated DNA Technologies, IA, USA), and cloned into each vectors for expression. Specifically, a heterodimer expressed by co-transfection of a vector capable of expressing a polypeptide corresponding to IL1R-hinge region-CH2-CH3 (S354C, T366W, K447del)-$(G_4S)_2$-IL18BP (SEQ ID NO:10), and IL1RAP-hinge region-CH2-CH3 (Y349C, T366S, L368A, Y407V, K447del)-IL18BP (SEQ ID NO:11) is referred to as 118T3 (FIG. 17A). Transient expression of 118T3 was performed in the same manner as in Comparative Example 1, and the culture medium at day-12 was filtered by using a Sartoclear Dynamics® Lab V (Sartorius, SDLV-1000-40C-E) filter system, and then purified by using a HiTrap Mab-Select SuRe (GE helathcare, 11003493) purification column. The final purified product was analyzed by using sodium dodecyl sulfate polyacrylamide gel electrophoresis (SDS-PAGE) in the same manner as in Comparative Example 1 (FIG. 17B). As a result of the analysis, a monomer mixture was confirmed at about 110 kDa under reducing conditions, and under non-reducing conditions, unassembled monomers were identified at about 110 kDa with products presumed to be a mixture of heterodimers and homodimers at about 220 kDa (FIG. 17B).

Example 2: Preparation of κλ Heterodimeric Polypeptide (118T3v01) with Bi-Specificity for IL-1 and IL-18

Figure 17C:
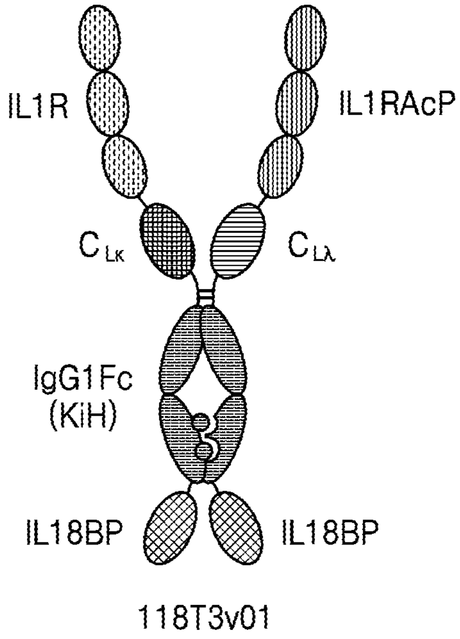
Figure 17D:
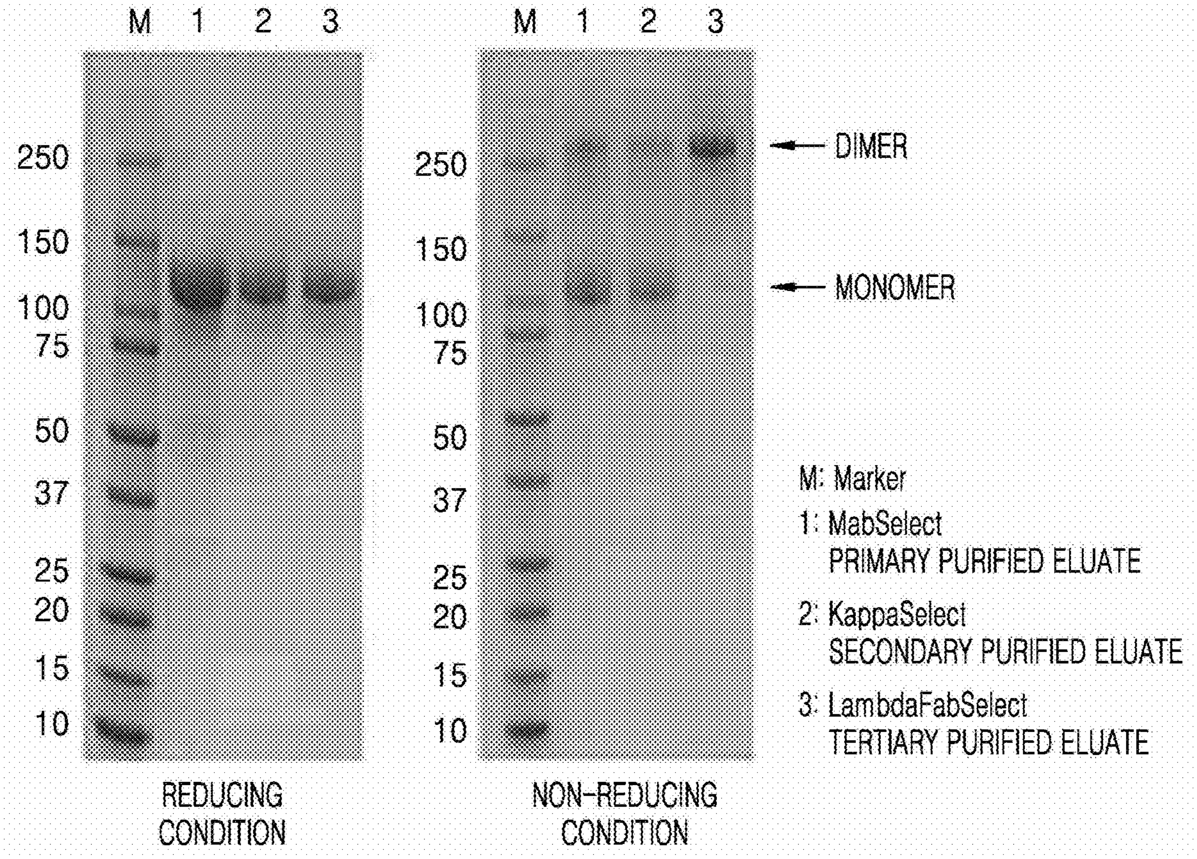

A heterodimer in which human IL18BP was fused to the C-terminus region of the Fc region of PET101 was prepared (FIG. 17C). Specifically, a heterodimer expressed by co-transfection of a vector capable of expressing a polypeptide corresponding to IL1R-kappa constant region-hinge region-CH2-CH3 (S354C, T366W, K447del)-$(G_4S)_2$-IL18BP (SEQ ID NO:12), and IL1RAP-lambda constant region-hinge region-CH2-CH3 (Y349C, T366S, L368A, Y407V, K447del)-IL18BP (SEQ ID NO:13) is referred to as 118T3v01 (FIG. 17C). Specifically, after the expression was carried out in the manner described in Example 1, the culture medium was recovered at day 12, filtered by using a Sartoclear Dynamics® Lab V (Sartorius, SDLV-1000-40C-E) filter system, and affinity chromatography-based purification was performed by using a HiTrap MabSelect SuRe (GE helathcare, 11003493) purification column. The primary purified product was subjected to affinity chromatography by using KappaSelect resin (GE helathcare, 17545801) followed by affinity chromatography by using LambdaFabSelect resin (GE helathcare, 17548201). Dialysis, concentration, quantification, and SDS-PAGE analysis of the primary (MabSelect), secondary (KappaSelect), and tertiary (LambdaFabSelect) purified products were performed in the manner described in Example 1. In the results of SDS-PAGE analysis of the MabSelect primary purified eluate under a non-reducing condition, unassembled monomers were confirmed at about 130 kDa. When the purification steps are completed to the tertiary purification, no monomer was identified, and dimer products presumed to be 118T3v01 were confirmed at about 250 kDa (FIG. 17D).

Experimental Example 13: Analysis of Binding Capacity of IL-1/IL-18 Bi-Specific Heterodimer for Human IL-1β and Human IL-18 by Using Enzyme-Linked Immunosorbent Assay (ELISA)

Figure 18:
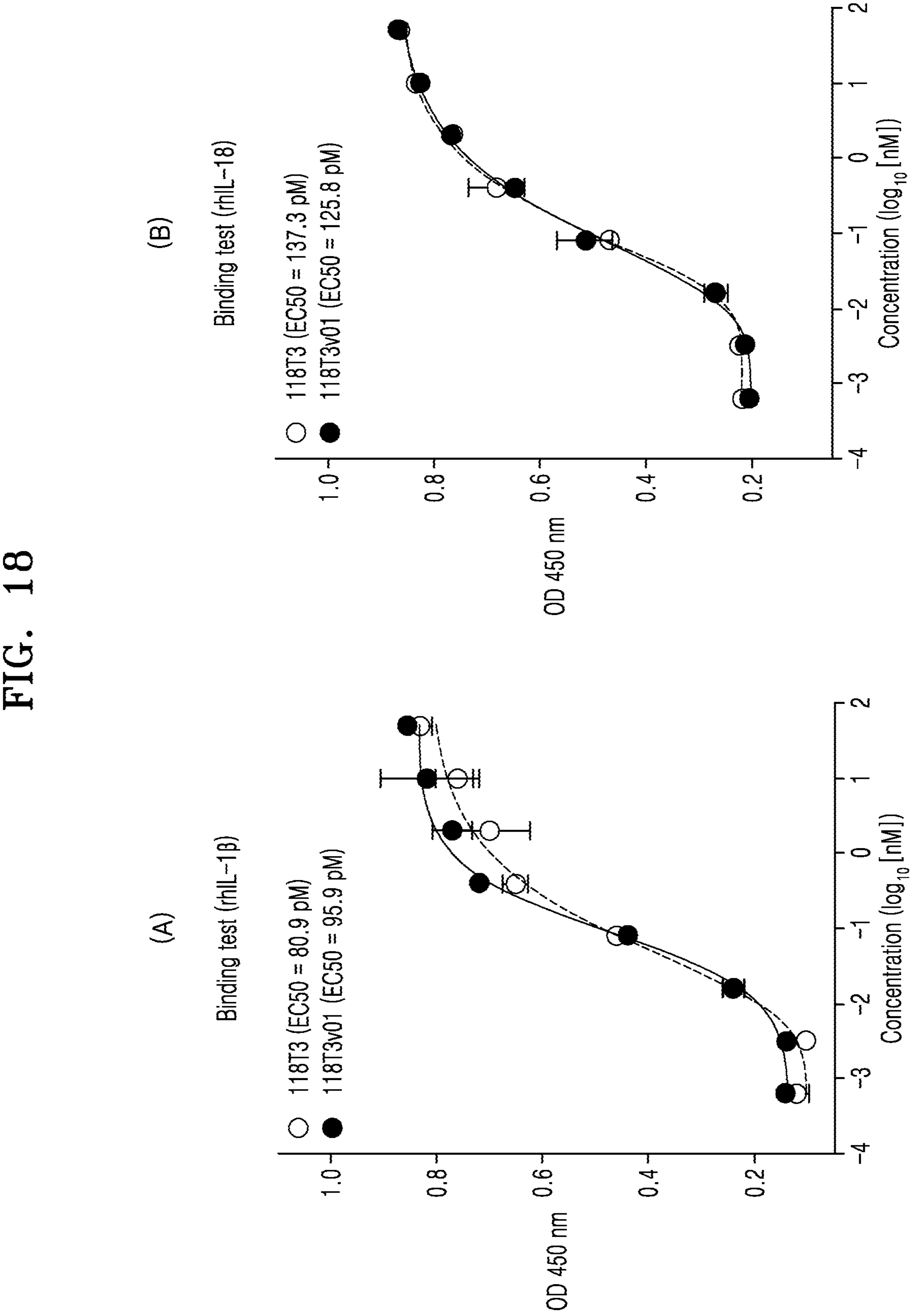
FIG. 18 shows results of analysis of binding of 118T3 and 118T3v01 to human IL-1β (A) and human IL-18 (B), by using ELISA.

Binding of IL-1/IL-18 bi-specific heterodimers 118T3 and 118T3v01 to human IL-1β and human IL-18 was analyzed in the same manner as in Experimental Example 2 by using ELISA. As a result of the analysis, it was confirmed that 118T3 and 118T3v01 had similar binding ability for human IL-1β (A of FIG. 18), and it was confirmed that the binding ability for human IL-18 was also similar (B of FIG. 18).

Experimental Example 14: Analysis of Binding Properties of 118T3v01 Through Surface Plasmon Resonance (SPR)

Figure 19:
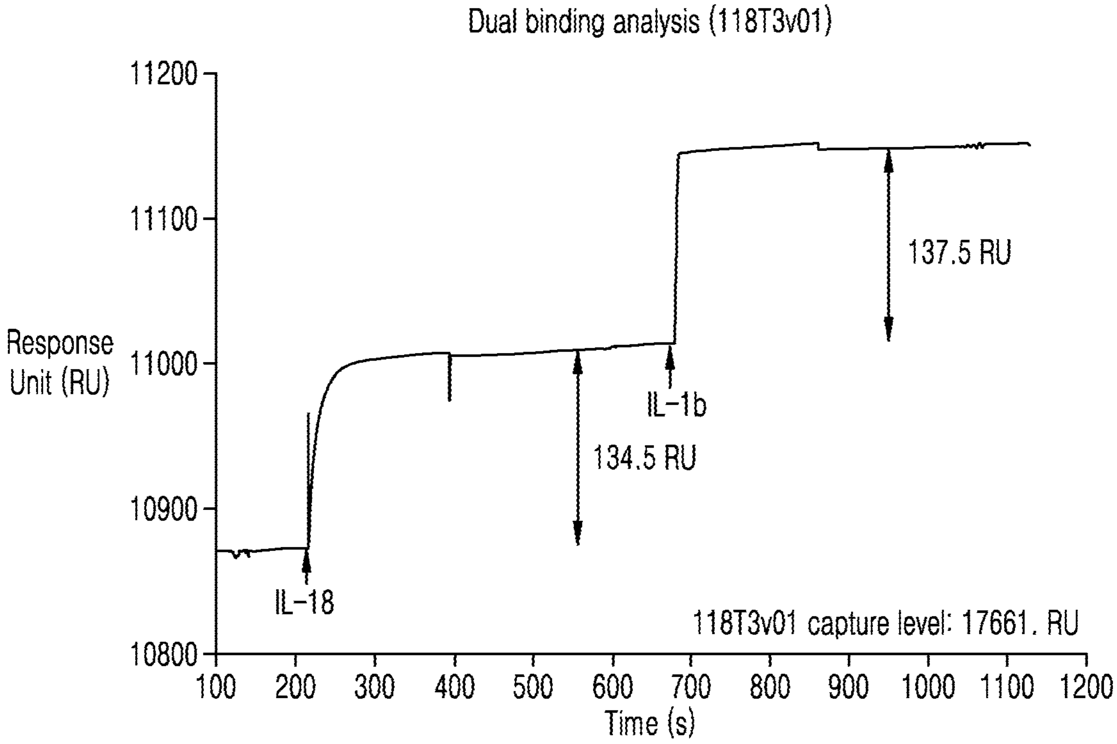
FIG. 19 shows results of analyzing simultaneous binding capacity of 118T3v01 to human IL-1β and human IL-18, by using surface plasmon resonance (SPR).

To confirm whether 118T3v01 binds to human IL-1β and human IL-18 simultaneously, surface plasmon resonance analysis was performed by using Biacore T200 (GE healthcare). 1×HBS-EP+ buffer (GE healthcare, BR100669) was used for dilution and as mobile phase for all samples used in the following analysis. Specifically, anti-human Fc antibodies included in the Human Antibody Capture Kit (GE healthcare, BR100839) were immobilized to the Series S CM5 Sensor Chip (GE healthcare, BR100530) according to the manufacturer's manual by using the Amine coupling kit (GE healthcare, BR100050). 100 nM of 118T3v01 (25 μg/ml) was loaded onto the sensor, on which anti-human Fc was immobilized, at a flow rate of 10 μl/min for 1 minute, equilibrium state was maintained for 2 minutes, and it was confirmed that 1766.1 RU of 118T3v01 was loaded on the surface of the sensor (FIG. 19). After that, subsequently, a binding reaction of 200 nM of human IL-18 (Sino Biological, 10119-HNCE) was induced for 3 minutes, and a dissociation reaction was induced for 5 minutes, and it was confirmed that 134.5 RU of human IL-18 was bound at an equilibrium state. (FIG. 19). Subsequently, a binding reaction and a dissociation reaction of 200 nM of human IL-1β (Sino Biological, 10139-HNAE) were performed for 3 minutes and 5 minutes, respectively, and it was confirmed that 137.5 RU of human IL-1β was bound. In a surface plasmon resonance analysis, an RU value is proportional to the mass of the material loaded on the sensor surface, and 1 RU means that 1 $pg/mm^2$ of material is fixed or bound to the sensor by interaction. Molecular weight of 118T3v01 is about 250 kDa, and human IL-1β and IL-18 have a molecular weight of about 18.4 kDa (FIG. 19). Based on this, it was confirmed that one 118T3v01 protein binds to 1.03 units of human IL-18 and 1.06 units of human IL-1β simultaneously (FIG. 19). In 118T3v01, two human IL18BP proteins capable of binding to human IL-18 are bound to the C-terminus of the Fc region, but only one of them was confirmed to bind to IL-18 (FIG. 19). This suggests that steric hindrance occurs between the two bound IL18BP proteins.

Example 3: Optimization of κλ Heterodimer with Bi-Specificity for IL-1 and IL-18 (118T3B)

Figure 20:
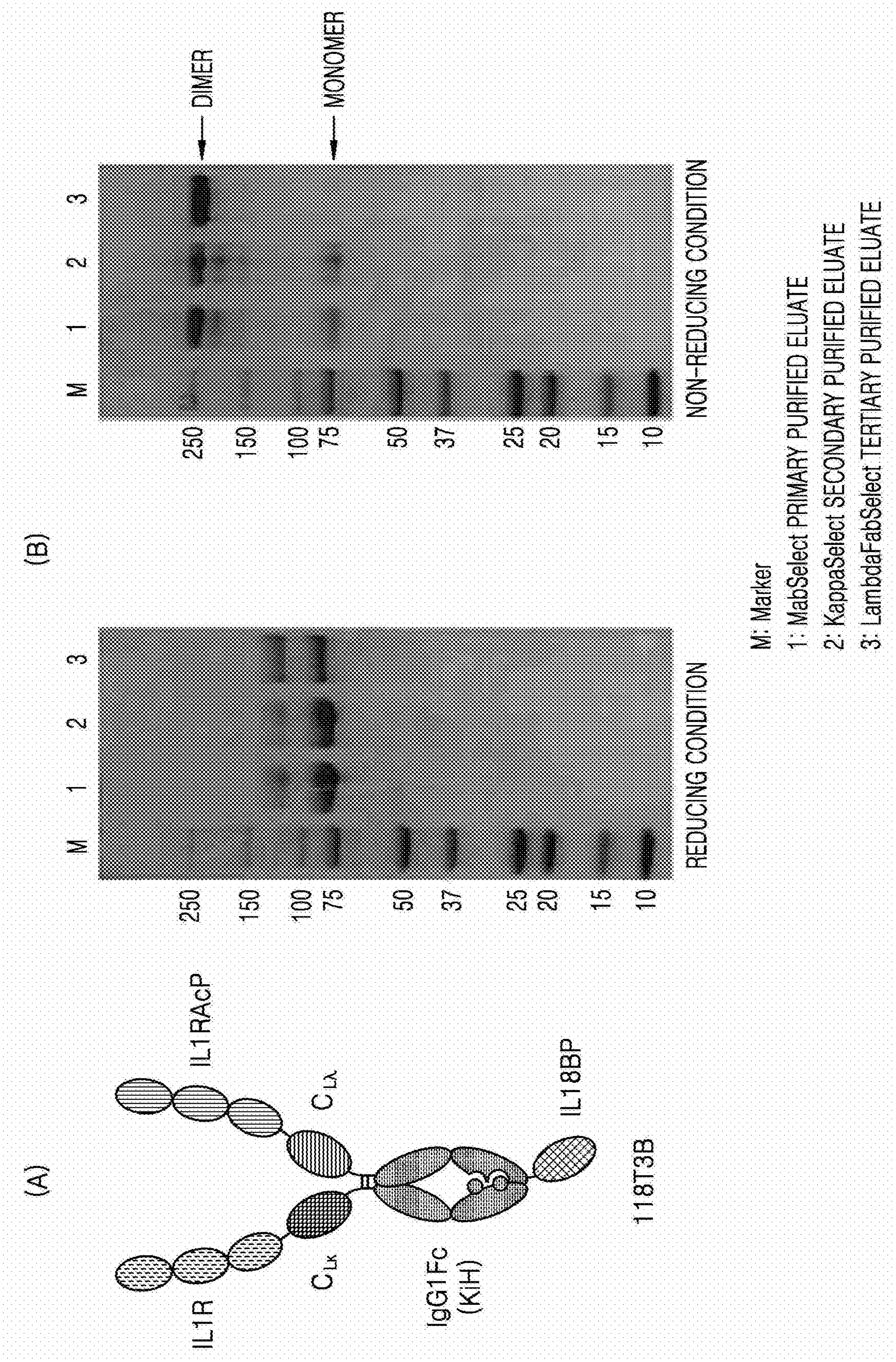
FIG. 20 shows a schematic diagram of 118T3B (A), in which one IL18BP is removed from 118T3v01, and SDS-PAGE results of purified products of 118T3B of each step under reducing and non-reducing conditions (B).

In Experimental Example 14, it was confirmed that one of two human IL18BP proteins present in 118T3v01 does not participate in target binding. In order to remove one unnecessarily bound IL18BP and reduce molecular weight, 118T3B, in which IL18BP of the knob region is removed, was prepared (A of FIG. 20). In order to express 118T3B, expression was carried out in the manner described in Comparative Example 1 with an expression vector encoding IL1R-kappa constant region-hinge region-CH2-CH3 (S354C, T366W) (SEQ ID NO:8), and IL1RAP-lambda constant region-hinge region-CH2-CH3 (Y349C, T366S, L368A, Y407V, K447del)-IL18BP (SEQ ID NO:13), and purification was carried out in the manner described in Example 1 (B of FIG. 20). As a result of an SDS-PAGE analysis, monomers of about 90 kDa and about 130 kDa were confirmed under reducing conditions, and it was confirmed that after the tertiary purification under non-reducing conditions, the monomers were removed, and high-purity substances presumed to be 118T3B heterodimers were obtained at about 220 kDa (B of FIG. 20).

Experimental Example 15: Evaluation of Binding Capacity of 118T3B for IL-1 and IL-18

Figure 21A:
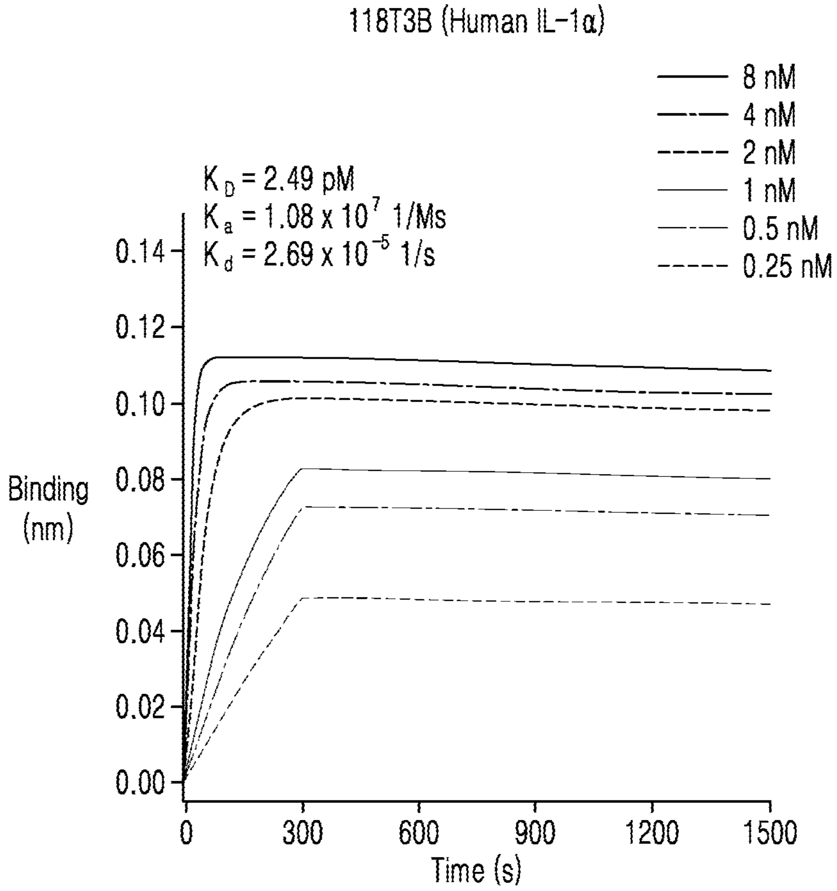
FIGS. 21A, 21B, 21C, and 21D show BLI sensorgram results of 118T3B for human IL-1α, human IL-1β, rhesus monkey IL-1β, and mouse IL-1β, respectively.
Figure 21B:
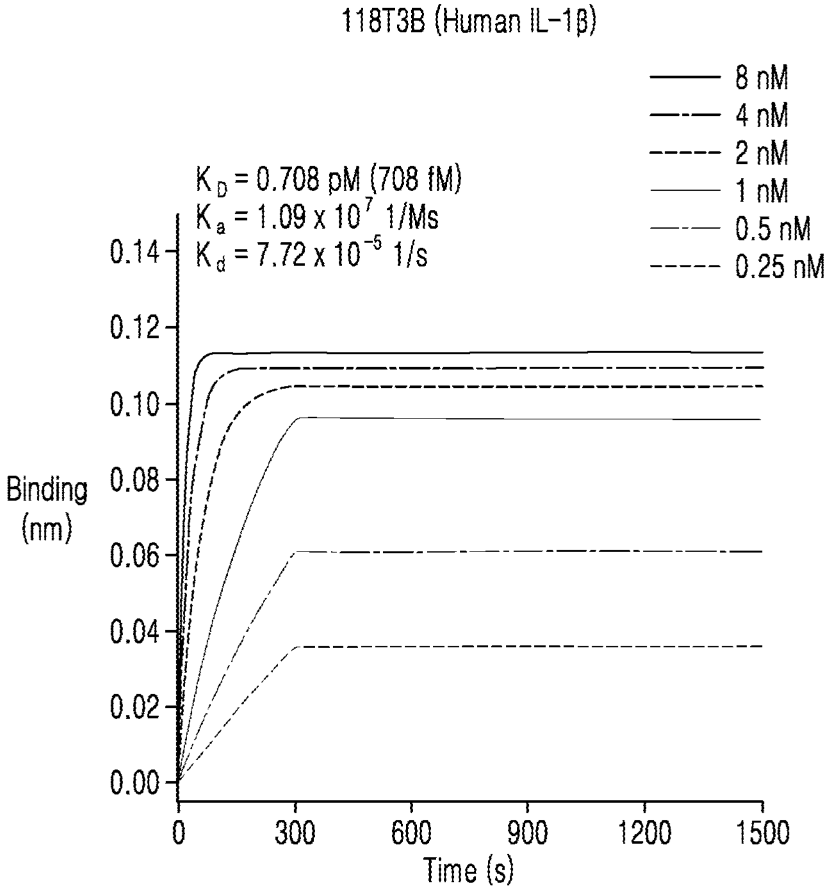
Figure 21C:
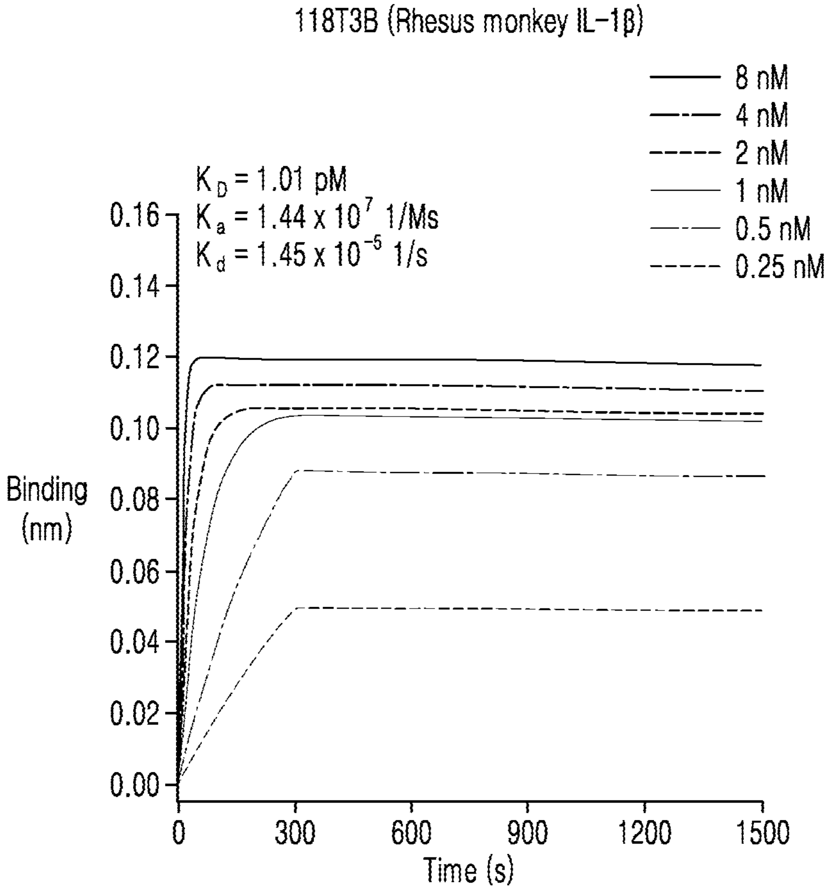
Figure 21D:
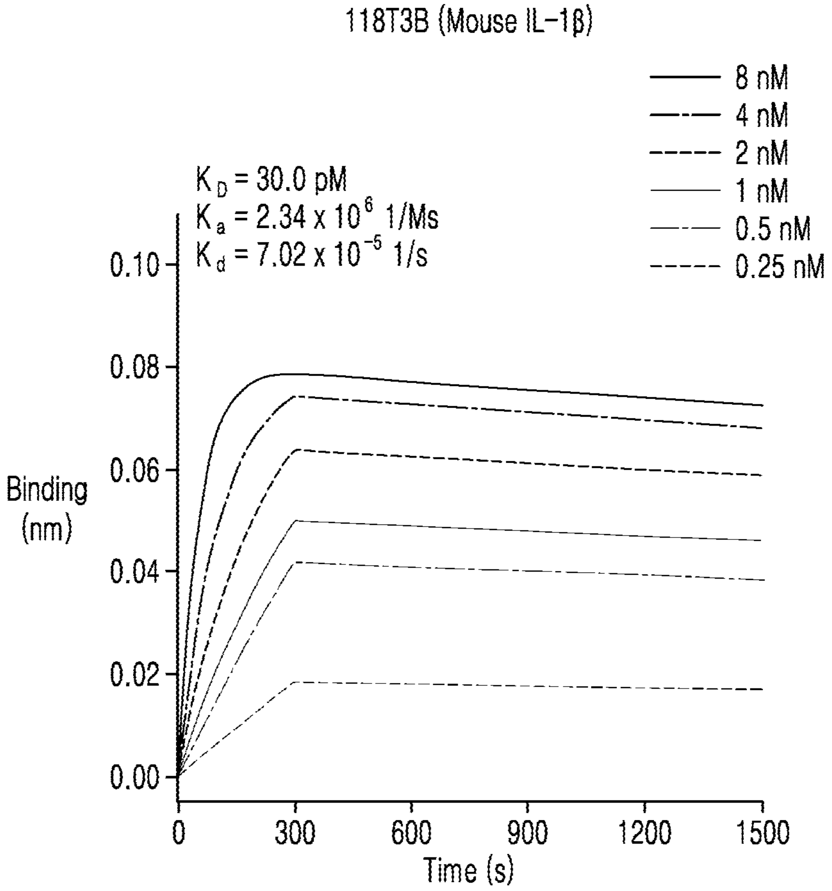
Figure 21E:
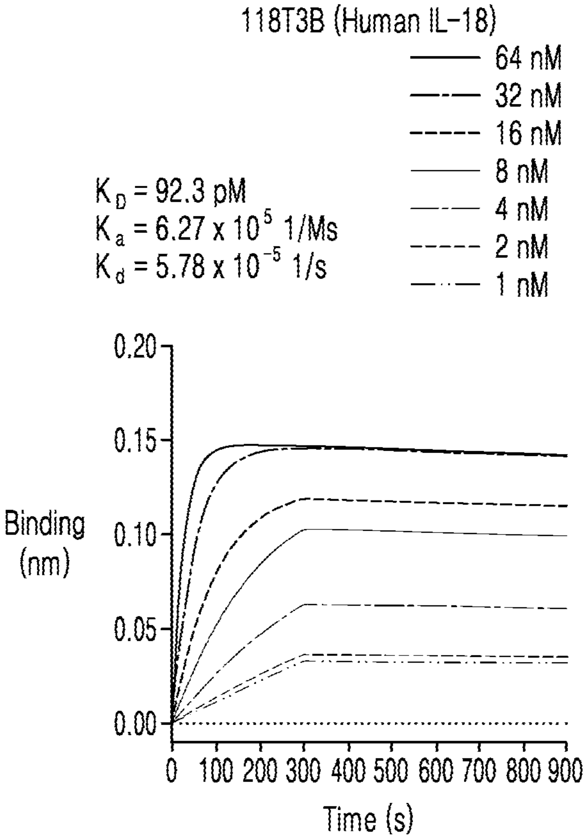
FIGS. 21E, 21F, and 21G show BLI sensorgram results of 118T3B for human IL-18, rhesus monkey IL-18, and mouse IL-18, respectively.
Figure 21F:
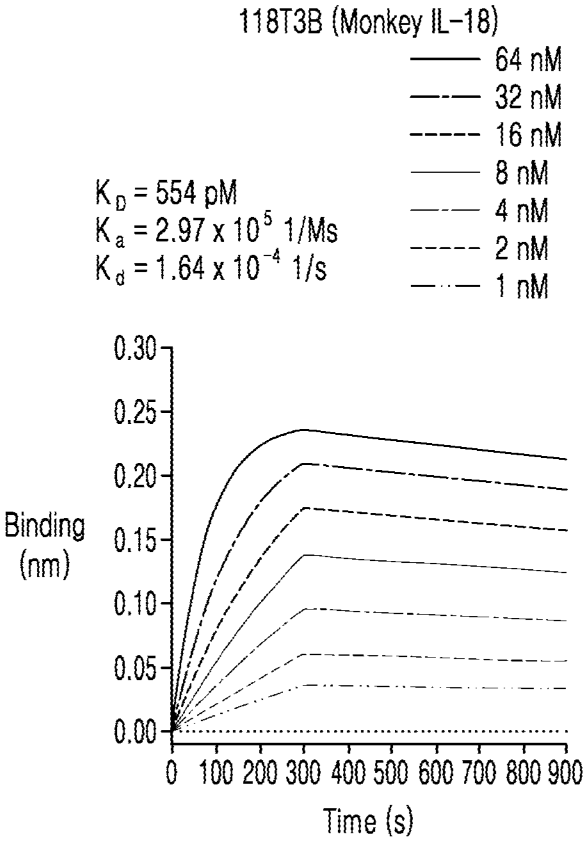
Figure 21G:
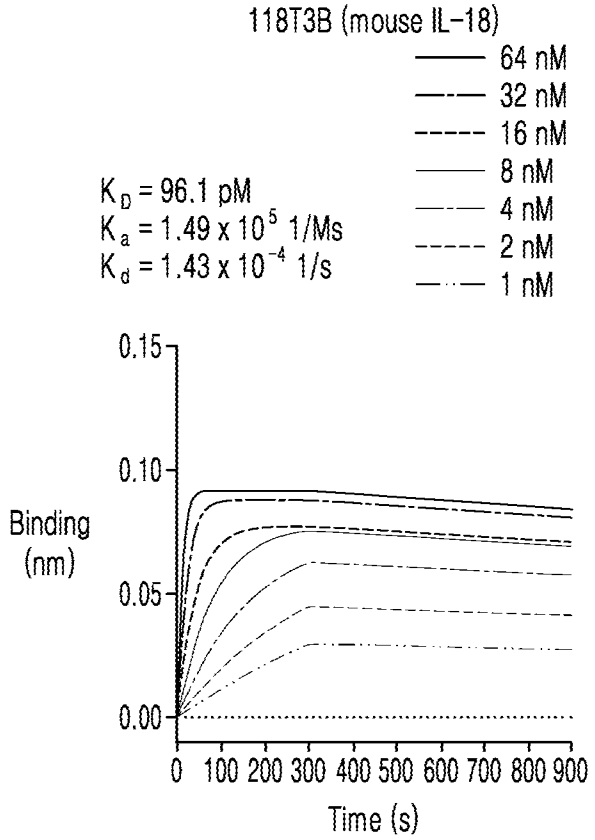

Evaluation of binding capacity of 118T3B for human IL-1α (R&D systems, 200-LA), human IL-1β (R&D systems, 201-LB), rhesus monkey IL-1β (R&D systems, 1318-RL), mouse IL-1β (R&D systems, 401-ML), human IL-18 (Sino Biological, 10139-HNAE), rhesus monkey IL-18 (R&D systems, 2548-RM), and mouse IL-18 (Sino Biological, 50073-MNCE) was performed at 30° C. by using Octet Red96e (Fortebio), a bio-layer interferometry (BLI) analysis equipment. Anti-Human IgG Fc Capture (AHC) biosensor (Fortebio, 18-5063) was used, for an analysis buffer, 10× Kinetics Buffer (ForteBio, 18-1042) was prepared as a running buffer by being diluted in pH 7.4 PBS (Gibco, 10010) and used, and rotation speed of the analysis plate was 1,000 rpm. 118T3B was diluted in the running buffer to a concentration of 20 μg/ml and loaded onto the biosensor for 5 minutes. In order to measure association rate constant ($K_a$) of 0.25 nM to 8 nM of human IL-1α, human IL-1β, rhesus monkey IL-1β, and mouse IL-1β, binding reactions were carried out for 300 seconds, and then, dissociation reactions were carried out for 1,200 seconds in the running buffer to determine the dissociation rate constant ($K_d$) (FIGS. 21A, 21B, 21C and 21D). In order to measure association rate constant ($K_a$) of 1 nM to 64 nM of human IL-18, rhesus monkey IL-18, and mouse IL-18, binding reactions were carried out for 300 seconds, and then, dissociation reactions were carried out for 600 seconds in the running buffer to determine the dissociation rate constant ($K_d$) (FIGS. 21E, 21F, and 21G). $K_a$ and $K_d$ values were measured by using a 1:1 binding model in the Octet analysis software (Fortebio), and equilibrium dissociation constant ($K_D$) values were determined based on the $K_a$ and $K_d$ values (FIGS. 21A, 21B, 21C, 21D, 21E, 21F, and 21G).

Figure 22:
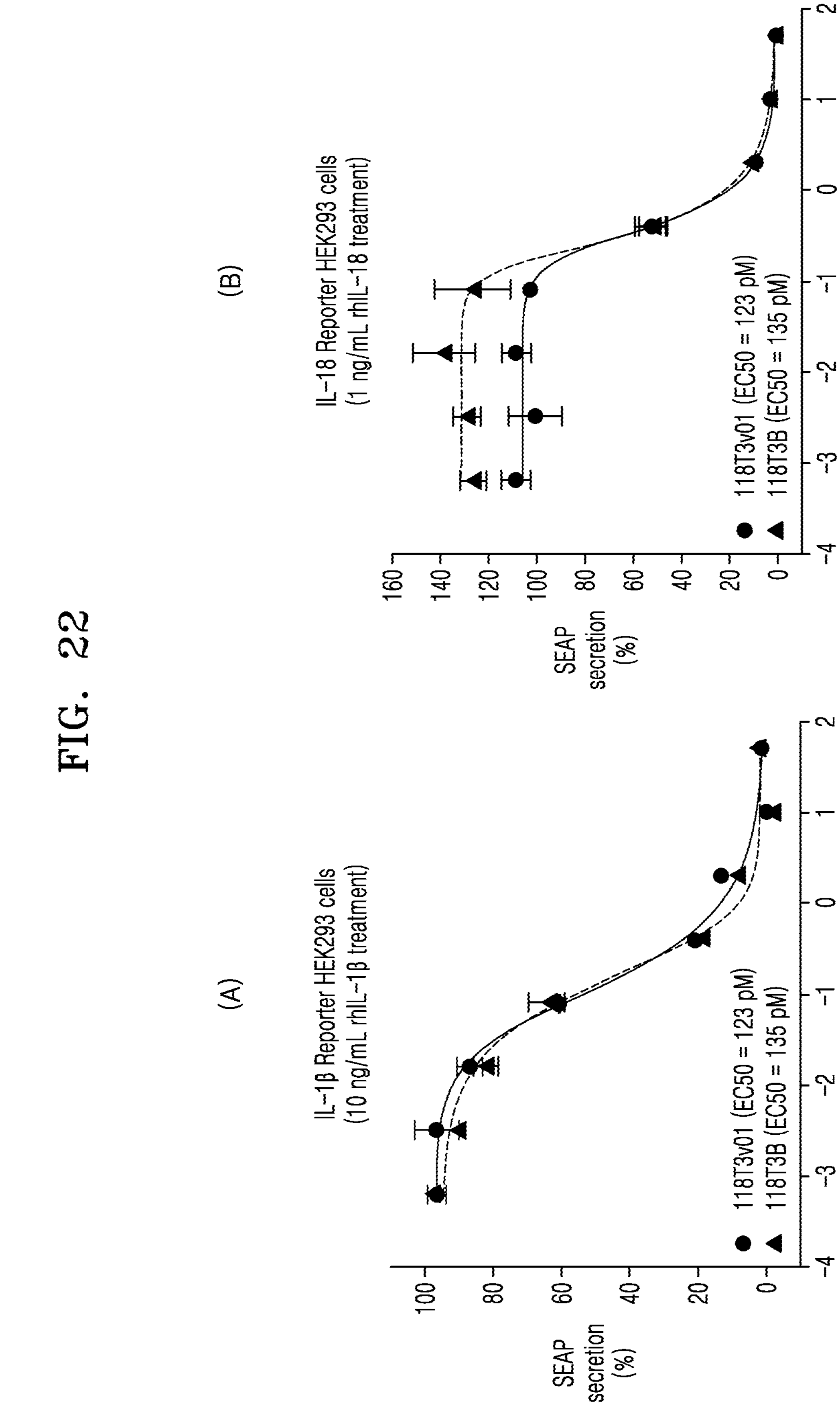
FIG. 22 shows results of analyzing inhibitory ability of 118T3v01 and 118T3B on signaling pathways of human IL-1β (A) and human IL-18 (B), in an IL-1 reporter cell line.

Experimental Example 16: Evaluation of Inhibitory Ability of IL-1/IL-18 Bi-Specific Heterodimer on IL-1 and IL-18 Signaling Pathways by Using Reporter Cell Line In order to evaluate inhibitory ability of the IL-1/IL-18 bi-specific heterodimers 118T3v01 and 118T3B on the signaling pathway of human IL-1β, the human IL-1β reporter cell line (Invivogen, hkb-il1b) and the experimental method described in Experimental Example 4 were used. As a result of the analysis, it was confirmed that 118T3v01 and 118T3B had similar $EC_{50}$ values of 123 pM and 135 pM, respectively (A of FIG. 22). To analyze the inhibitory ability of 118T3v01 and 118T3B on human IL-18, the IL-18 Reporter HEK293 cell line (Invivogen, hkb-hmil18) was used, and the analysis was carried out in the same manner as in Experimental Example 4 by using 1 ng/ml of human IL-18 (Sino Biological, 10139-HNAE). As a result of the analysis, it was confirmed that 118T3v01 and 118T3B had similar $EC_{50}$ values of 392 pM and 305 pM, respectively (B of FIG. 22).

Example 4: Preparation of IL-1 and TGF-β Bi-Specific κλ Heterodimeric Polypeptide (PET301)

Gene sequences encoding 24 to 184 amino acid residues constituting the extracellular region of human TGFβRII (GenBank: ACZ58377.1) were chemically synthesized (Integrated DNA Technologies, IA, USA). The synthesized genes were cloned into each vectors for each expression, through XhoI and XbaI restriction sites, and the obtained positive clones were verified through DNA sequencing. Specifically, a heterodimer expressed in the production cell line by co-transfection of a vector capable of expressing a polypeptide corresponding to IL1R-kappa constant region-hinge region-CH2-CH3 (S354C, T366W, K447A)-$(G_4S)_4$G-TGFβRII (SEQ ID NO:14), and IL1RAP-lambda constant region-hinge region-CH2-CH3 (Y349C, T366S, L368A, Y407V, K447A)-$(G_4S)_4$G-TGFβRII (SEQ ID NO:15) is referred to as PET301 (A of FIG. 23). The IL-1/TGF-β bi-specific heterodimer was transiently expressed in the manner described in Comparative Example 1, and purified in the manner described in Example 1. Products of each purification step were analyzed by using sodium dodecyl sulfate polyacrylamide gel electrophoresis (SDS-PAGE) (B of FIG. 23). As a result of the analysis, monomers were confirmed at about 110 kDa under a reducing condition, and the monomers were removed after the tertiary purification under a non-reducing condition, and products estimated as PET301 heterodimers were confirmed at about 220 kDa (B of FIG. 23).

Experimental Example 17: Analysis of Binding Ability of PET301 to Human IL-1β and Human TGF-β by Using Enzyme-Linked Immunosorbent Assay (ELISA)

Figure 24A:
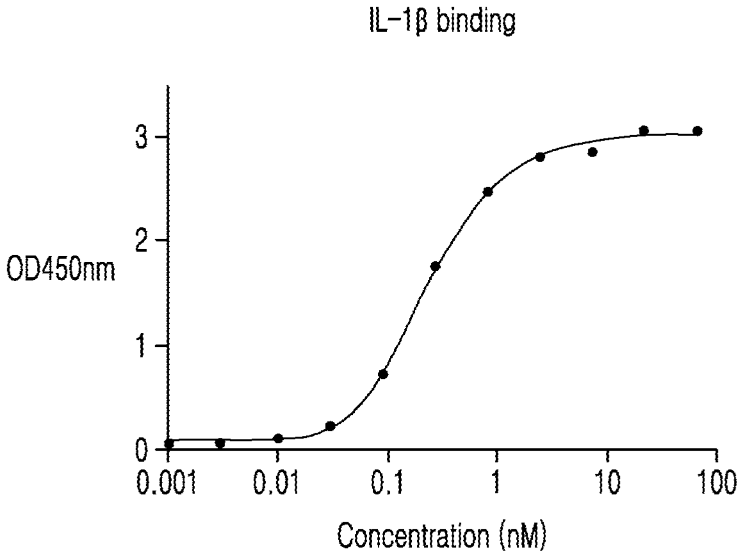
FIGS. 24A, 24B, 24C, and 24D show results of analyzing binding of PET301 to human IL-1β, human TGF-β1, human TGF-β3 and human TGF-β2, respectively by using ELISA.
Figure 24B:
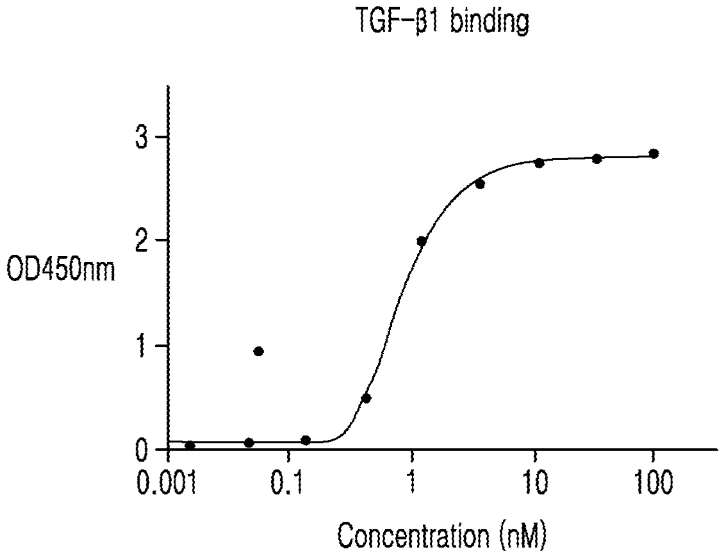
Figure 24C:
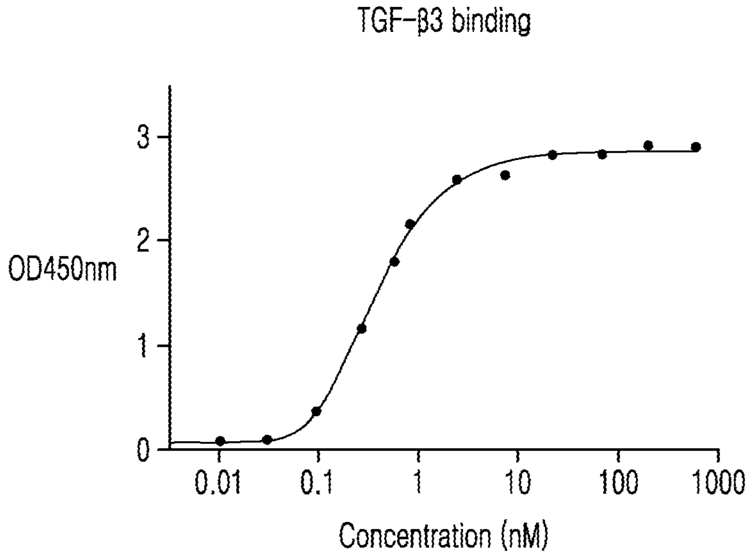

Analysis of binding of PET301 to human IL-1β and human TGF-β was performed by using ELISA. Human IL-1β (Sino Biological, 10139-HNAE), or human TGF-β1 (R&D systems, 7754-BH), or human TGF-β3 (R&D systems, 8420-B3) were coated on a 96-well immunosorbent assay plate (Corning, 3590) at a concentration of 60 ng/well. Next day, the plate was washed with Phosphate Buffered Saline with Tween-20 (PBST; TEKNOVA, P1192). Blocking was performed by incubating the plate for 1 hour at room temperature using PBST to which 1% (w/v) bovine serum albumin (BSA) was added, and then the plate was washed 3 times. PET301 was diluted in PBST containing 1% (w/v) BSA to an appropriate concentration and treated in each well, binding was induced at room temperature for 1 hour, and the plate was washed three times. Peroxidase-bound anti-human IgG Fc goat antibodies (Invitrogen 31413) were diluted (1:10,000) in PBST containing 1% (w/v) BSA to induce binding, and washed 3 times with PBST, and then TMB substrate solution (Thermo Fisher Scientific, 34028) was reacted, and absorbance was measured at 450 nm. Based on the measured absorbance, $EC_{50}$ values were calculated by using the Prism 7 software (GraphPad Software) (FIG. 24A, 24B, 24C, and Table 4).

Figure 24D:
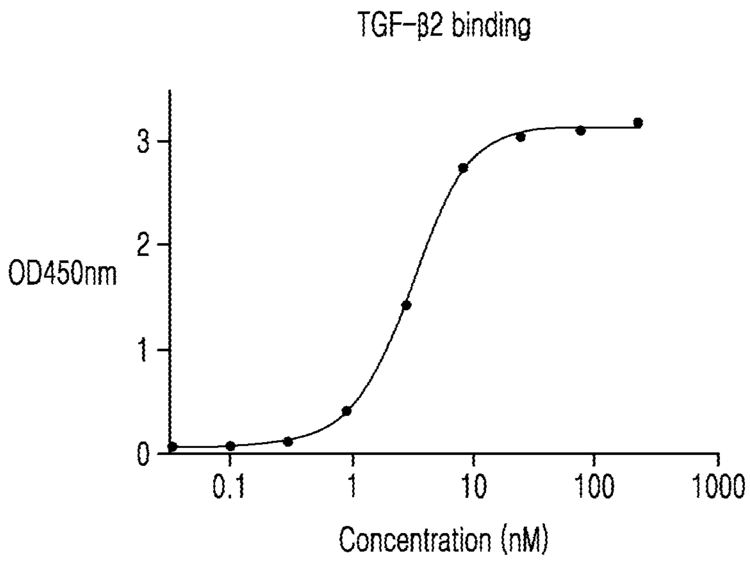

Analysis of the binding capacity of PET301 and human TGF-β2 was performed by coating PET301 on a 96-well plate for immunosorbent assay (Corning, 3590) at a concentration of 60 ng/well. Blocking was carried out at room temperature for 1 hour in PBST containing 1% (w/v) BSA, and human TGF-β2 (Peprotech, 100-35B) at an appropriate concentration was diluted in PBST containing 1% (w/v) BSA to induce a binding reaction for 1 hour at room temperature, and then, anti-TGF-β2 biotinylated antibodies (R&D systems, BAF302) were treated to induce a binding reaction at room temperature for 1 hour. Streptavidin-HRP (R&D systems) was treated to induce a binding reaction at room temperature for 30 minutes, and the subsequent processes were performed in the same manner as described above (FIG. 24D, Table 4).

As a result of the analysis, PET301 was confirmed to have $EC_{50}$ values of 0.226 nM, 0.799 nM, and 0.357 nM for human IL-1β, human TGF-β1, and human TGF-β3, respectively, and have high affinity to these antigens (Table 4). PET301 was confirmed to have an $EC_{50}$ value of 3.081 nM and have a relatively low affinity for human TGF-β2 (Table 4).

TABLE 4

Analysis of binding capacity of PET301 to human IL-1β, human TGF-β1, human TGF-β2, and human TGF-β3

| | Human IL-1β | Human TGF-β1 | Human TGF-β2 | Human TGF-β3 |
|---|---|---|---|---|
| $EC_{50}$ (nM) | 0.226 | 0.799 | 3.081 | 0.357 |

Figure 25A:
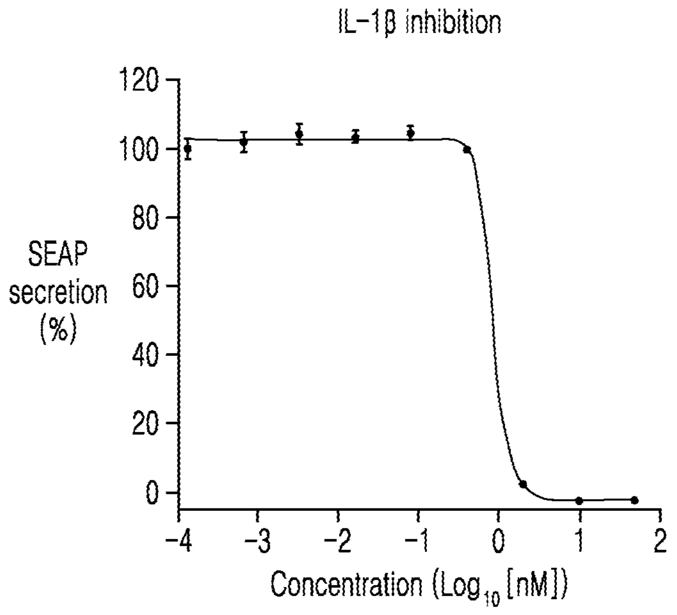
FIGS. 25A, 25B, 25C, and 25D show results of analyzing inhibitory ability of PET301 on human IL-1β by using a IL-1 reporter cell line, and inhibitory ability of PET301 on human TGF-β1, human TGF-β3, and human TGF-β2, respectively by using a TGF-β reporter cell line.
Figure 25B:
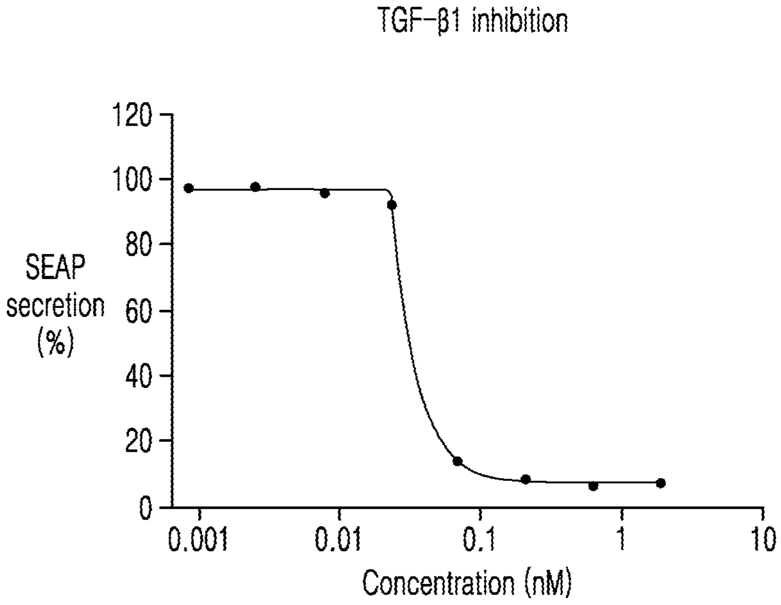
Figure 25C:
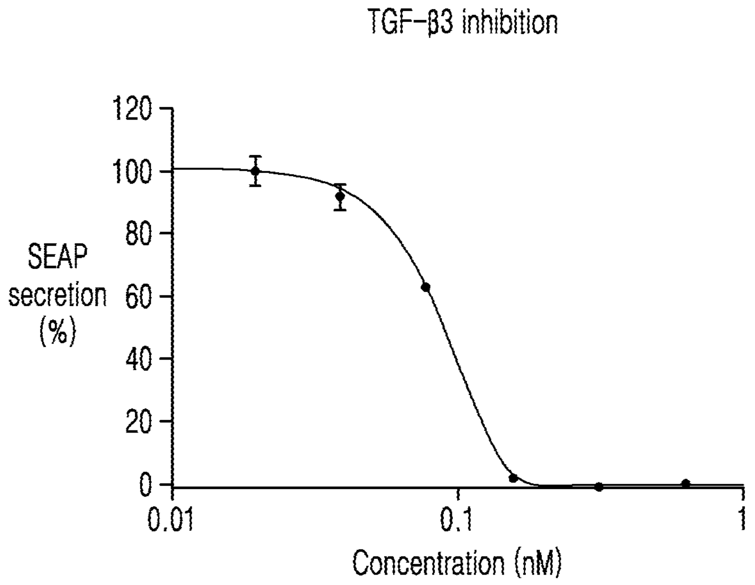
Figure 25D:
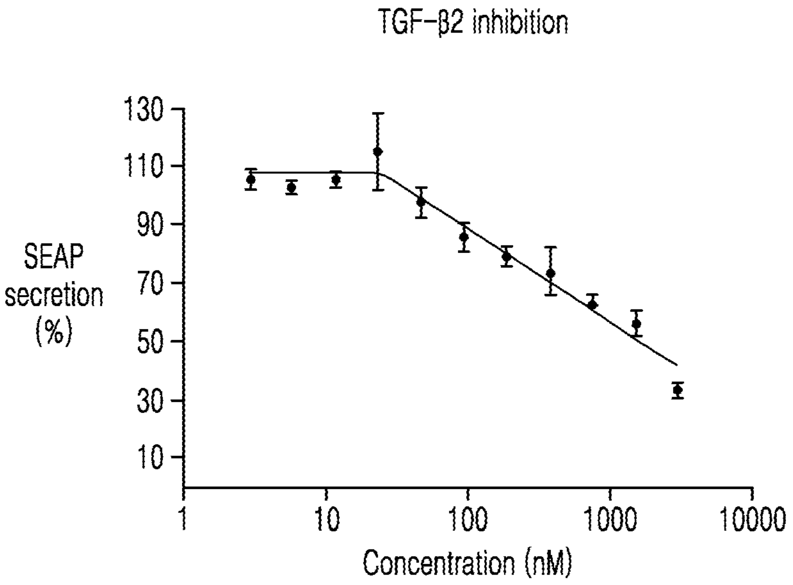

Experimental Example 18: Evaluation of Inhibitory Ability of PET301 on IL-1 and TGF-β Signaling Pathways Using Reporter Cell Line Evaluation of inhibitory ability of PET301 on the human IL-1β signaling pathway was performed in the same manner as described in Experimental Example 4 by using the IL-1β Reporter HEK 293 cell line (Invivogen, hkb-il1b). As a result of the analysis, it was confirmed that PET301 in the IL-1β Reporter HEK 293 cell line had an $EC_{50}$ value of 1.056 nM (FIG. 25A). In order to analyze the inhibitory ability of PET301 on human TGF-β1, human TGF-β2, and human TGF-β3, the TGF-β Reporter HEK 293 cell line (Invivogen, hkb-tgfb) was used, and 1 ng/ml of human TGF-β1 (R&D systems, 7754-BH), or 10 ng/ml of human TGF-β2 (Peprotech, 100-35B), or 1 ng/ml or human TGF-β3 (R&D systems, 8420-B3) were used for activation of the cell line. The expression of SEAP was quantified by using Quanti-Blue solution (Invivogen, rep-qbs) for the analysis of the TGF-β inhibitory ability of PET301. As a result of the analysis, it was confirmed that PET301 had $EC_{50}$ values of 30 pM and 89 pM for human TGF-β1 and human TGF-β3, respectively, and did not efficiently inhibit human TGF-β2 (FIGS. 25B, 25C and 25D).

What is claimed is:

1. A heterodimeric Fc fusion protein, comprising: i) a first polypeptide including a first target protein, a first linker, and a first Fc region of an immunoglobulin in the N-terminus to C-terminus direction; and ii) a second polypeptide including a second target protein, a second linker, and a second Fc region of an immunoglobulin in the N-terminus to C-terminus direction, wherein the first Fc region or the second Fc region comprises a hinge region or a part thereof, and CH2 and CH3 regions of an antibody molecule, the first target protein and the second target protein are different proteins from each other, and the first linker and the second linker are a κ light chain constant region ($C_{L\kappa}$) or a variant of the κ light chain constant region and a λ light chain constant region ($C_{L\lambda}$) or a variant of λ light chain constant region, respectively, wherein the variant of the κ light chain constant region comprises a κ light chain constant region in which cysteine forming a disulfide bond with CH1 of a heavy chain constant region is mutated in order to prevent unnecessary assembly, wherein the variant of the λ light chain constant region is a λ light chain constant region in which cysteine forming a disulfide bond with CH1 of a heavy chain constant region is mutated in order to prevent unnecessary assembly, or serine at the C-terminus is deleted, and wherein the cysteine forming a disulfide bond with the CH1 of a heavy chain constant region is at position 214, based on Kabat numbering.

2. The heterodimeric Fc fusion protein of claim 1, wherein cysteine forming a disulfide bond with CH1 of a heavy chain constant region is substituted with serine, alanine, or valine in the variant of the κ light chain constant region ($C_{L\kappa}$), the variant of the λ light chain constant region ($C_{L\lambda}$), or both.

3. The heterodimeric Fc fusion protein of claim 1, further comprising a third target protein at one or more of the C-terminus of the first polypeptide, or the C-terminus of the second polypeptide.

4. The heterodimeric Fc fusion protein of claim 1, wherein the heterodimeric Fc fusion protein has mono-specificity or multi-specificity.

5. The heterodimeric Fc fusion protein of claim 1, wherein the first target protein or the second target protein is a ligand, a receptor, a cytokine, an enzyme, or a peptide.

6. The heterodimeric Fc fusion protein of claim 5, wherein the receptor is a cytokine receptor.

7. The heterodimeric Fc fusion protein of claim 6, wherein the cytokine is at least one selected from the group consisting of Interleukin-1 (IL1), Interleukin-2 (IL2), Interleukin-3 (IL3), Interleukin-4 (IL4), Interleukin-5 (IL5), Interleukin-6 (IL6), Interleukin-11 (IL11), Interleukin-13 (IL13), interleukin-15 (IL15), interleukin-18 (IL18), interleukin-23 (IL23), interleukin-31 (IL31), interleukin-33 (IL33), interleukin-35 (IL35), interleukin-36 (IL36), leukemia inhibitory factor (LIF), oncostatin M (OSM), granulocyte macrophage colony stimulating factor (GM-CSF), gamma-interferon (IFN-γ), thymic stromal lymphopoietin (TSLP), transforming growth factor-beta (TGF-β), vascular endothelial growth factor (VEGF), and tumor necrosis factor-alpha (TNF-α).

8. The heterodimeric Fc fusion protein of claim 1, wherein one of the first target protein and the second target protein is interleukin-1 receptor type 1 (IL1R1), and the other is interleukin-1 receptor accessory protein (IL1RAcP).

9. The heterodimeric Fc fusion protein of claim 8, wherein the first target protein is interleukin-1 receptor type 1 (IL1R1), the first linker is a κ light chain constant region ($C_{L\kappa}$) or a variant of the κ light chain constant region, the second target protein is interleukin-1 receptor accessory protein (IL1RAcP), and the second linker is a λ light chain constant region ($C_{L\lambda}$) or a variant of the λ light chain constant region, wherein the variant of the κ light chain constant region is a κ light chain constant region in which cysteine forming a disulfide bond with CH1 of the heavy chain constant region is substituted with serine, alanine, or valine, wherein the variant of the λ light chain constant region is a λ light chain constant region in which cysteine forming a disulfide bond with CH1 of the heavy chain constant region is substituted with serine, alanine, or valine, or serine at the C-terminus is deleted, and wherein the cysteine forming a disulfide bond with the heavy chain constant region CH1 is at position 214, based on Kabat numbering.

10. The heterodimeric Fc fusion protein of claim 8, wherein the interleukin-1 receptor type 1 (IL1R1), and interleukin-1 receptor accessory protein (IL1RAcP) are each an ectodomain thereof.

11. The heterodimeric Fc fusion protein of claim 1, further comprising a third target protein comprising interleukin-18 binding protein (IL18BP), or a type II transforming growth factor-beta receptor (TGFβR II).

12. The heterodimeric Fc fusion protein of claim 11, wherein the interleukin-18 binding protein (IL18BP) is comprised at any one of the C-terminus of the first polypeptide and the C-terminus of the second polypeptide.

13. The heterodimeric Fc fusion protein of claim 12, wherein the interleukin-18 binding protein (IL18BP) is comprised at the C-terminus of the second polypeptide.

14. The heterodimeric Fc fusion protein of claim 11, wherein the type II transforming growth factor-beta receptor (TGFβRII) is comprised at both the C-terminus of the first polypeptide, and the C-terminus of the second polypeptide.

15. The heterodimeric Fc fusion protein of claim 1, wherein the CH3 region of the first Fc region and the second Fc region is mutated to promote heterodimer formation in the first Fc region and the second Fc region.

16. The heterodimeric Fc fusion protein of claim 15, wherein the CH3 region of the first Fc region and the second Fc region comprises a knob-into-hole mutation.

17. The heterodimeric Fc fusion protein of claim 1, wherein the first linker or the second linker is bound to the N-terminus of the Fc region hinge.

18. The heterodimeric Fc fusion protein of claim 1, further comprising a third linker between the C-terminus of the first polypeptide and the first target protein, between the C-terminus of the second polypeptide and the second target protein, or between the first polypeptide and the first target protein and between the second polypeptide and the second target protein.

19. The heterodimeric Fc fusion protein of claim 18, wherein the third linker is a Gly-Ser (GS) linker.

* * * * *

SEQUENCE LISTING

<160> NUMBER OF SEQ ID NOS: 23

<210> SEQ ID NO 1
<211> LENGTH: 217
<212> TYPE: PRT
<213> ORGANISM: Homo sapiens

<400> SEQUENCE: 1

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Thr Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys
210 215

<210> SEQ ID NO 2
<211> LENGTH: 217
<212> TYPE: PRT
<213> ORGANISM: Artificial sequence
<220> FEATURE:
<223> OTHER INFORMATION: Human IgG1 Fc(Hole; Y349C, T366S, L368A, Y407V)
<220> FEATURE:
<221> NAME/KEY: misc_feature
<222> LOCATION: (1)..(217)
<223> OTHER INFORMATION: Human IgG1 Fc(Knob; S354C, T366W)

<400> SEQUENCE: 2

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Cys Arg Glu Glu Met
115 120 125

Thr Lys Asn Gln Val Ser Leu Trp Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys
210 215

<210> SEQ ID NO 3
<211> LENGTH: 217
<212> TYPE: PRT

<213> ORGANISM: Artificial Sequence
<220> FEATURE:
<223> OTHER INFORMATION: Human IgG1 Fc(Knob; S354C, T366W)
<220> FEATURE:
<221> NAME/KEY: misc_feature
<222> LOCATION: (1)..(217)
<223> OTHER INFORMATION: Human IgG1 Fc(Hole; Y349C, T366S, L368A, Y407V)

<400> SEQUENCE: 3

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Cys Thr Leu Pro Pro Ser Arg Glu Glu Met
115 120 125

Thr Lys Asn Gln Val Ser Leu Ser Cys Ala Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Val Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys
210 215

<210> SEQ ID NO 4
<211> LENGTH: 562
<212> TYPE: PRT
<213> ORGANISM: Artificial Sequence
<220> FEATURE:
<223> OTHER INFORMATION: IL-1R-hinge region-CH2-CH3(S354C, T366W)
<220> FEATURE:
<221> NAME/KEY: misc_feature
<222> LOCATION: (1)..(562)
<223> OTHER INFORMATION: IL-1R-hinge region-CH2-CH3(S354C, T366W)

<400> SEQUENCE: 4

Met Lys Val Leu Leu Arg Leu Ile Cys Phe Ile Ala Leu Leu Ile Ser
1 5 10 15

Ser Leu Glu Ala Asp Lys Cys Lys Glu Arg Glu Glu Lys Ile Ile Leu
20 25 30

Val Ser Ser Ala Asn Glu Ile Asp Val Arg Pro Cys Pro Leu Asn Pro
35 40 45

Asn Glu His Lys Gly Thr Ile Thr Trp Tyr Lys Asp Asp Ser Lys Thr
50 55 60

Pro Val Ser Thr Glu Gln Ala Ser Arg Ile His Gln His Lys Glu Lys

```
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Ser Gly Asp
                325                 330                 335

Lys Thr His Thr Cys Pro Pro Cys Pro Ala Pro Glu Leu Leu Gly Gly
            340                 345                 350

Pro Ser Val Phe Leu Phe Pro Pro Lys Pro Lys Asp Thr Leu Met Ile
        355                 360                 365

Ser Arg Thr Pro Glu Val Thr Cys Val Val Val Asp Val Ser His Glu
    370                 375                 380

Asp Pro Glu Val Lys Phe Asn Trp Tyr Val Asp Gly Val Glu Val His
385                 390                 395                 400

Asn Ala Lys Thr Lys Pro Arg Glu Glu Gln Tyr Asn Ser Thr Tyr Arg
                405                 410                 415

Val Val Ser Val Leu Thr Val Leu His Gln Asp Trp Leu Asn Gly Lys
            420                 425                 430

Glu Tyr Lys Cys Lys Val Ser Asn Lys Ala Leu Pro Ala Pro Ile Glu
        435                 440                 445

Lys Thr Ile Ser Lys Ala Lys Gly Gln Pro Arg Glu Pro Gln Val Tyr
    450                 455                 460

Thr Leu Pro Pro Cys Arg Glu Glu Met Thr Lys Asn Gln Val Ser Leu
465                 470                 475                 480

Trp Cys Leu Val Lys Gly Phe Tyr Pro Ser Asp Ile Ala Val Glu Trp
                485                 490                 495
```

```
Glu Ser Asn Gly Gln Pro Glu Asn Asn Tyr Lys Thr Thr Pro Pro Val
            500                 505                 510

Leu Asp Ser Asp Gly Ser Phe Phe Leu Tyr Ser Lys Leu Thr Val Asp
        515                 520                 525

Lys Ser Arg Trp Gln Gln Gly Asn Val Phe Ser Cys Ser Val Met His
    530                 535                 540

Glu Ala Leu His Asn His Tyr Thr Gln Lys Ser Leu Ser Leu Ser Pro
545                 550                 555                 560

Gly Lys


<210> SEQ ID NO 5
<211> LENGTH: 697
<212> TYPE: PRT
<213> ORGANISM: Artificial Sequence
<220> FEATURE:
<223> OTHER INFORMATION: IL-1RAcP-hinge region-CH2-CH3(Y349C, T366S,
      L368A, Y407V)
<220> FEATURE:
<221> NAME/KEY: misc_feature
<222> LOCATION: (1)..(697)
<223> OTHER INFORMATION: IL-1RAcP-hinge region-CH2-CH3(Y349C, T366S,
      L368A, Y407V)

<400> SEQUENCE: 5

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255
```

-continued

Glu Pro Gly Glu Glu Leu Leu Ile Pro Cys Thr Val Tyr Phe Ser Phe
260 265 270

Leu Met Asp Ser Arg Asn Glu Val Trp Trp Thr Ile Asp Gly Lys Lys
275 280 285

Pro Asp Asp Ile Thr Ile Asp Val Thr Ile Asn Glu Ser Ile Ser His
290 295 300

Ser Arg Thr Glu Asp Glu Thr Arg Thr Gln Ile Leu Ser Ile Lys Lys
305 310 315 320

Val Thr Ser Glu Asp Leu Lys Arg Ser Tyr Val Cys His Ala Arg Ser
325 330 335

Ala Lys Gly Glu Val Ala Lys Ala Ala Lys Val Lys Gln Lys Val Pro
340 345 350

Ala Pro Arg Tyr Thr Val Glu Gln Pro Lys Ala Ala Pro Gly Gln Pro
355 360 365

Lys Ala Ala Pro Ser Val Thr Leu Phe Pro Pro Ser Ser Glu Glu Leu
370 375 380

Gln Ala Asn Lys Ala Thr Leu Val Cys Leu Ile Ser Asp Phe Tyr Pro
385 390 395 400

Gly Ala Val Thr Val Ala Trp Lys Ala Asp Ser Ser Pro Val Lys Ala
405 410 415

Gly Val Glu Thr Thr Thr Pro Ser Lys Gln Ser Asn Asn Lys Tyr Ala
420 425 430

Ala Ser Ser Tyr Leu Ser Leu Thr Pro Glu Gln Trp Lys Ser His Arg
435 440 445

Ser Tyr Ser Cys Gln Val Thr His Glu Gly Ser Thr Val Glu Lys Thr
450 455 460

Val Ala Pro Thr Glu Ser Asp Lys Thr His Thr Cys Pro Pro Cys Pro
465 470 475 480

Ala Pro Glu Leu Leu Gly Gly Pro Ser Val Phe Leu Phe Pro Pro Lys
485 490 495

Pro Lys Asp Thr Leu Met Ile Ser Arg Thr Pro Glu Val Thr Cys Val
500 505 510

Val Val Asp Val Ser His Glu Asp Pro Glu Val Lys Phe Asn Trp Tyr
515 520 525

Val Asp Gly Val Glu Val His Asn Ala Lys Thr Lys Pro Arg Glu Glu
530 535 540

Gln Tyr Asn Ser Thr Tyr Arg Val Val Ser Val Leu Thr Val Leu His
545 550 555 560

Gln Asp Trp Leu Asn Gly Lys Glu Tyr Lys Cys Lys Val Ser Asn Lys
565 570 575

Ala Leu Pro Ala Pro Ile Glu Lys Thr Ile Ser Lys Ala Lys Gly Gln
580 585 590

Pro Arg Glu Pro Gln Val Cys Thr Leu Pro Pro Ser Arg Glu Glu Met
595 600 605

Thr Lys Asn Gln Val Ser Leu Ser Cys Ala Val Lys Gly Phe Tyr Pro
610 615 620

Ser Asp Ile Ala Val Glu Trp Glu Ser Asn Gly Gln Pro Glu Asn Asn
625 630 635 640

Tyr Lys Thr Thr Pro Pro Val Leu Asp Ser Asp Gly Ser Phe Phe Leu
645 650 655

Val Ser Lys Leu Thr Val Asp Lys Ser Arg Trp Gln Gln Gly Asn Val
660 665 670

Phe Ser Cys Ser Val Met His Glu Ala Leu His Asn His Tyr Thr Gln

```
        675                 680                 685

Lys Ser Leu Ser Leu Ser Pro Gly Lys
    690                 695


<210> SEQ ID NO 6
<211> LENGTH: 107
<212> TYPE: PRT
<213> ORGANISM: Homo sapiens

<400> SEQUENCE: 6

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Ser
            100                 105


<210> SEQ ID NO 7
<211> LENGTH: 104
<212> TYPE: PRT
<213> ORGANISM: Homo sapiens

<400> SEQUENCE: 7

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Ser
            100


<210> SEQ ID NO 8
<211> LENGTH: 674
<212> TYPE: PRT
<213> ORGANISM: Artificial Sequence
<220> FEATURE:
<223> OTHER INFORMATION: IL-1R-kappa constant region-hinge region-CH2-
      CH3 (S354C, T366W)
<220> FEATURE:
<221> NAME/KEY: misc_feature
<222> LOCATION: (1)..(674)
<223> OTHER INFORMATION: IL-1R-kappa constant region-hinge region-CH2-
      CH3 (S354C, T366W)

<400> SEQUENCE: 8
```

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Ser Gly Thr
                325                 330                 335

Val Ala Ala Pro Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
        355                 360                 365

Leu Asn Asn Phe Tyr Pro Arg Glu Ala Lys Val Gln Trp Lys Val Asp
    370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln

```
            420                 425                 430

Gly Leu Ser Ser Pro Val Thr Lys Ser Phe Asn Arg Gly Glu Ser Asp
        435                 440                 445

Lys Thr His Thr Cys Pro Pro Cys Pro Ala Pro Glu Leu Leu Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
    530                 535                 540

Glu Tyr Lys Cys Lys Val Ser Asn Lys Ala Leu Pro Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Glu Glu Met Thr Lys Asn Gln Val Ser Leu
            580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly Lys


<210> SEQ ID NO 9
<211> LENGTH: 697
<212> TYPE: PRT
<213> ORGANISM: Artificial Sequence
<220> FEATURE:
<223> OTHER INFORMATION: IL-1RAcP-lambda constant region-hinge
      region-CH2-CH3 (Y349C, T366S, L368A, Y407V)
<220> FEATURE:
<221> NAME/KEY: misc_feature
<222> LOCATION: (1)..(697)
<223> OTHER INFORMATION: IL-1RAcP-lambda constant region-hinge
      region-CH2-CH3 (Y349C, T366S, L368A, Y407V)

<400> SEQUENCE: 9

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80
```

-continued

```
Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Gln Pro Lys Ala Ala Pro Gly Gln Pro
        355                 360                 365

Lys Ala Ala Pro Ser Val Thr Leu Phe Pro Pro Ser Ser Glu Glu Leu
    370                 375                 380

Gln Ala Asn Lys Ala Thr Leu Val Cys Leu Ile Ser Asp Phe Tyr Pro
385                 390                 395                 400

Gly Ala Val Thr Val Ala Trp Lys Ala Asp Ser Ser Pro Val Lys Ala
                405                 410                 415

Gly Val Glu Thr Thr Thr Pro Ser Lys Gln Ser Asn Asn Lys Tyr Ala
            420                 425                 430

Ala Ser Ser Tyr Leu Ser Leu Thr Pro Glu Gln Trp Lys Ser His Arg
        435                 440                 445

Ser Tyr Ser Cys Gln Val Thr His Glu Gly Ser Thr Val Glu Lys Thr
    450                 455                 460

Val Ala Pro Thr Glu Ser Asp Lys Thr His Thr Cys Pro Pro Cys Pro
465                 470                 475                 480

Ala Pro Glu Leu Leu Gly Gly Pro Ser Val Phe Leu Phe Pro Pro Lys
                485                 490                 495
```

```
Pro Lys Asp Thr Leu Met Ile Ser Arg Thr Pro Glu Val Thr Cys Val
            500                 505                 510

Val Val Asp Val Ser His Glu Asp Pro Glu Val Lys Phe Asn Trp Tyr
        515                 520                 525

Val Asp Gly Val Glu Val His Asn Ala Lys Thr Lys Pro Arg Glu Glu
    530                 535                 540

Gln Tyr Asn Ser Thr Tyr Arg Val Val Ser Val Leu Thr Val Leu His
545                 550                 555                 560

Gln Asp Trp Leu Asn Gly Lys Glu Tyr Lys Cys Lys Val Ser Asn Lys
                565                 570                 575

Ala Leu Pro Ala Pro Ile Glu Lys Thr Ile Ser Lys Ala Lys Gly Gln
            580                 585                 590

Pro Arg Glu Pro Gln Val Cys Thr Leu Pro Pro Ser Arg Glu Glu Met
        595                 600                 605

Thr Lys Asn Gln Val Ser Leu Ser Cys Ala Val Lys Gly Phe Tyr Pro
    610                 615                 620

Ser Asp Ile Ala Val Glu Trp Glu Ser Asn Gly Gln Pro Glu Asn Asn
625                 630                 635                 640

Tyr Lys Thr Thr Pro Pro Val Leu Asp Ser Asp Gly Ser Phe Phe Leu
                645                 650                 655

Val Ser Lys Leu Thr Val Asp Lys Ser Arg Trp Gln Gln Gly Asn Val
            660                 665                 670

Phe Ser Cys Ser Val Met His Glu Ala Leu His Asn His Tyr Thr Gln
        675                 680                 685

Lys Ser Leu Ser Leu Ser Pro Gly Lys
    690                 695


<210> SEQ ID NO 10
<211> LENGTH: 735
<212> TYPE: PRT
<213> ORGANISM: Artificial Sequence
<220> FEATURE:
<223> OTHER INFORMATION: IL1R-hinge region-CH2-CH3(S354C, T366W,
      K447del)-(G4S)2-IL18BP
<220> FEATURE:
<221> NAME/KEY: misc_feature
<222> LOCATION: (1)..(735)
<223> OTHER INFORMATION: IL1R-hinge region-CH2-CH3(S354C, T366W,
      K447del)-(G4S)2-IL18BP

<400> SEQUENCE: 10

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125
```

-continued

```
Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Ser Gly Asp
                325                 330                 335

Lys Thr His Thr Cys Pro Pro Cys Pro Ala Pro Glu Leu Leu Gly Gly
            340                 345                 350

Pro Ser Val Phe Leu Phe Pro Pro Lys Pro Lys Asp Thr Leu Met Ile
        355                 360                 365

Ser Arg Thr Pro Glu Val Thr Cys Val Val Val Asp Val Ser His Glu
    370                 375                 380

Asp Pro Glu Val Lys Phe Asn Trp Tyr Val Asp Gly Val Glu Val His
385                 390                 395                 400

Asn Ala Lys Thr Lys Pro Arg Glu Glu Gln Tyr Asn Ser Thr Tyr Arg
                405                 410                 415

Val Val Ser Val Leu Thr Val Leu His Gln Asp Trp Leu Asn Gly Lys
            420                 425                 430

Glu Tyr Lys Cys Lys Val Ser Asn Lys Ala Leu Pro Ala Pro Ile Glu
        435                 440                 445

Lys Thr Ile Ser Lys Ala Lys Gly Gln Pro Arg Glu Pro Gln Val Tyr
    450                 455                 460

Thr Leu Pro Pro Cys Arg Glu Glu Met Thr Lys Asn Gln Val Ser Leu
465                 470                 475                 480

Trp Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Leu Tyr Ser Lys Leu Thr Val Asp
        515                 520                 525

Lys Ser Arg Trp Gln Gln Gly Asn Val Phe Ser Cys Ser Val Met His
    530                 535                 540

Glu Ala Leu His Asn His Tyr Thr Gln Lys Ser Leu Ser Leu Ser Pro
```

```
545                 550                 555                 560

Gly Gly Gly Gly Gly Ser Gly Gly Gly Gly Ser Thr Pro Val Ser Gln
                565                 570                 575

Thr Thr Thr Ala Ala Thr Ala Ser Val Arg Ser Thr Lys Asp Pro Cys
            580                 585                 590

Pro Ser Gln Pro Pro Val Phe Pro Ala Ala Lys Gln Cys Pro Ala Leu
        595                 600                 605

Glu Val Thr Trp Pro Glu Val Glu Val Pro Leu Asn Gly Thr Leu Ser
    610                 615                 620

Leu Ser Cys Val Ala Cys Ser Arg Phe Pro Asn Phe Ser Ile Leu Tyr
625                 630                 635                 640

Trp Leu Gly Asn Gly Ser Phe Ile Glu His Leu Pro Gly Arg Leu Trp
                645                 650                 655

Glu Gly Ser Thr Ser Arg Glu Arg Gly Ser Thr Gly Thr Gln Leu Cys
            660                 665                 670

Lys Ala Leu Val Leu Glu Gln Leu Thr Pro Ala Leu His Ser Thr Asn
        675                 680                 685

Phe Ser Cys Val Leu Val Asp Pro Glu Gln Val Val Gln Arg His Val
    690                 695                 700

Val Leu Ala Gln Leu Trp Ala Gly Leu Arg Ala Thr Leu Pro Pro Thr
705                 710                 715                 720

Gln Glu Ala Leu Pro Ser Ser His Ser Ser Pro Gln Gln Gln Gly
                725                 730                 735


<210> SEQ ID NO 11
<211> LENGTH: 759
<212> TYPE: PRT
<213> ORGANISM: Artificial Sequence
<220> FEATURE:
<223> OTHER INFORMATION: IL1RAcP-hinge region-CH2-CH3(Y349C, T366S,
      L368A, Y407V, K447del)-(G4S)2-IL18BP
<220> FEATURE:
<221> NAME/KEY: misc_feature
<222> LOCATION: (1)..(759)
<223> OTHER INFORMATION: IL1RAcP-hinge region-CH2-CH3(Y349C, T366S,
      L368A, Y407V, K447del)-(G4S)2-IL18BP

<400> SEQUENCE: 11

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
```

-continued

```
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Asp Lys Thr His Thr Cys Pro Pro Cys
        355                 360                 365

Pro Ala Pro Glu Leu Leu Gly Gly Pro Ser Val Phe Leu Phe Pro Pro
    370                 375                 380

Lys Pro Lys Asp Thr Leu Met Ile Ser Arg Thr Pro Glu Val Thr Cys
385                 390                 395                 400

Val Val Val Asp Val Ser His Glu Asp Pro Glu Val Lys Phe Asn Trp
                405                 410                 415

Tyr Val Asp Gly Val Glu Val His Asn Ala Lys Thr Lys Pro Arg Glu
            420                 425                 430

Glu Gln Tyr Asn Ser Thr Tyr Arg Val Val Ser Val Leu Thr Val Leu
        435                 440                 445

His Gln Asp Trp Leu Asn Gly Lys Glu Tyr Lys Cys Lys Val Ser Asn
    450                 455                 460

Lys Ala Leu Pro Ala Pro Ile Glu Lys Thr Ile Ser Lys Ala Lys Gly
465                 470                 475                 480

Gln Pro Arg Glu Pro Gln Val Cys Thr Leu Pro Pro Ser Arg Glu Glu
                485                 490                 495

Met Thr Lys Asn Gln Val Ser Leu Ser Cys Ala Val Lys Gly Phe Tyr
            500                 505                 510

Pro Ser Asp Ile Ala Val Glu Trp Glu Ser Asn Gly Gln Pro Glu Asn
        515                 520                 525

Asn Tyr Lys Thr Thr Pro Pro Val Leu Asp Ser Asp Gly Ser Phe Phe
    530                 535                 540

Leu Val Ser Lys Leu Thr Val Asp Lys Ser Arg Trp Gln Gln Gly Asn
545                 550                 555                 560

Val Phe Ser Cys Ser Val Met His Glu Ala Leu His Asn His Tyr Thr
                565                 570                 575
```

Gln Lys Ser Leu Ser Leu Ser Pro Gly Gly Gly Gly Gly Ser Gly Gly
580 585 590

Gly Gly Ser Thr Pro Val Ser Gln Thr Thr Thr Ala Ala Thr Ala Ser
595 600 605

Val Arg Ser Thr Lys Asp Pro Cys Pro Ser Gln Pro Pro Val Phe Pro
610 615 620

Ala Ala Lys Gln Cys Pro Ala Leu Glu Val Thr Trp Pro Glu Val Glu
625 630 635 640

Val Pro Leu Asn Gly Thr Leu Ser Leu Ser Cys Val Ala Cys Ser Arg
645 650 655

Phe Pro Asn Phe Ser Ile Leu Tyr Trp Leu Gly Asn Gly Ser Phe Ile
660 665 670

Glu His Leu Pro Gly Arg Leu Trp Glu Gly Ser Thr Ser Arg Glu Arg
675 680 685

Gly Ser Thr Gly Thr Gln Leu Cys Lys Ala Leu Val Leu Glu Gln Leu
690 695 700

Thr Pro Ala Leu His Ser Thr Asn Phe Ser Cys Val Leu Val Asp Pro
705 710 715 720

Glu Gln Val Val Gln Arg His Val Val Leu Ala Gln Leu Trp Ala Gly
725 730 735

Leu Arg Ala Thr Leu Pro Pro Thr Gln Glu Ala Leu Pro Ser Ser His
740 745 750

Ser Ser Pro Gln Gln Gln Gly
755

<210> SEQ ID NO 12
<211> LENGTH: 847
<212> TYPE: PRT
<213> ORGANISM: Artificial Sequence
<220> FEATURE:
<223> OTHER INFORMATION: IL1R-kappa constant region-hinge region-CH2-
CH3(S354C, T366W, K447del)-(G4S)2-IL18BP
<220> FEATURE:
<221> NAME/KEY: misc_feature
<222> LOCATION: (1)..(847)
<223> OTHER INFORMATION: IL1R-kappa constant region-hinge region-CH2-
CH3(S354C, T366W, K447del)-(G4S)2-IL18BP

<400> SEQUENCE: 12

Met Lys Val Leu Leu Arg Leu Ile Cys Phe Ile Ala Leu Leu Ile Ser
1 5 10 15

Ser Leu Glu Ala Asp Lys Cys Lys Glu Arg Glu Glu Lys Ile Ile Leu
20 25 30

Val Ser Ser Ala Asn Glu Ile Asp Val Arg Pro Cys Pro Leu Asn Pro
35 40 45

Asn Glu His Lys Gly Thr Ile Thr Trp Tyr Lys Asp Asp Ser Lys Thr
50 55 60

Pro Val Ser Thr Glu Gln Ala Ser Arg Ile His Gln His Lys Glu Lys
65 70 75 80

Leu Trp Phe Val Pro Ala Lys Val Glu Asp Ser Gly His Tyr Tyr Cys
85 90 95

Val Val Arg Asn Ser Ser Tyr Cys Leu Arg Ile Lys Ile Ser Ala Lys
100 105 110

Phe Val Glu Asn Glu Pro Asn Leu Cys Tyr Asn Ala Gln Ala Ile Phe
115 120 125

Lys Gln Lys Leu Pro Val Ala Gly Asp Gly Gly Leu Val Cys Pro Tyr
130 135 140

```
Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Ser Gly Thr
                325                 330                 335

Val Ala Ala Pro Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
        355                 360                 365

Leu Asn Asn Phe Tyr Pro Arg Glu Ala Lys Val Gln Trp Lys Val Asp
    370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
            420                 425                 430

Gly Leu Ser Ser Pro Val Thr Lys Ser Phe Asn Arg Gly Glu Ser Asp
        435                 440                 445

Lys Thr His Thr Cys Pro Pro Cys Pro Ala Pro Glu Leu Leu Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
    530                 535                 540

Glu Tyr Lys Cys Lys Val Ser Asn Lys Ala Leu Pro Ala Pro Ile Glu
545                 550                 555                 560
```

```
Lys Thr Ile Ser Lys Ala Lys Gly Gln Pro Arg Glu Pro Gln Val Tyr
                565                 570                 575

Thr Leu Pro Pro Cys Arg Glu Glu Met Thr Lys Asn Gln Val Ser Leu
            580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly Gly Gly Gly Gly Ser Gly Gly Gly Gly Ser Thr Pro Val Ser Gln
        675                 680                 685

Thr Thr Thr Ala Ala Thr Ala Ser Val Arg Ser Thr Lys Asp Pro Cys
    690                 695                 700

Pro Ser Gln Pro Pro Val Phe Pro Ala Ala Lys Gln Cys Pro Ala Leu
705                 710                 715                 720

Glu Val Thr Trp Pro Glu Val Glu Val Pro Leu Asn Gly Thr Leu Ser
                725                 730                 735

Leu Ser Cys Val Ala Cys Ser Arg Phe Pro Asn Phe Ser Ile Leu Tyr
            740                 745                 750

Trp Leu Gly Asn Gly Ser Phe Ile Glu His Leu Pro Gly Arg Leu Trp
        755                 760                 765

Glu Gly Ser Thr Ser Arg Glu Arg Gly Ser Thr Gly Thr Gln Leu Cys
    770                 775                 780

Lys Ala Leu Val Leu Glu Gln Leu Thr Pro Ala Leu His Ser Thr Asn
785                 790                 795                 800

Phe Ser Cys Val Leu Val Asp Pro Glu Gln Val Val Gln Arg His Val
                805                 810                 815

Val Leu Ala Gln Leu Trp Ala Gly Leu Arg Ala Thr Leu Pro Pro Thr
            820                 825                 830

Gln Glu Ala Leu Pro Ser Ser His Ser Ser Pro Gln Gln Gln Gly
        835                 840                 845


<210> SEQ ID NO 13
<211> LENGTH: 735
<212> TYPE: PRT
<213> ORGANISM: Artificial Sequence
<220> FEATURE:
<223> OTHER INFORMATION: IL1RAcP-lambda constant region-hinge
      region-CH2-CH3(Y349C, T366S, L368A, Y407V, K447del)-(G4S)2-IL18BP
<220> FEATURE:
<221> NAME/KEY: misc_feature
<222> LOCATION: (1)..(735)
<223> OTHER INFORMATION: IL1RAcP-lambda constant region-hinge
      region-CH2-CH3(Y349C, T366S, L368A, Y407V, K447del)-(G4S)2-IL18BP

<400> SEQUENCE: 13

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45
```

-continued

```
Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Ser Gly Asp
                325                 330                 335

Lys Thr His Thr Cys Pro Pro Cys Pro Ala Pro Glu Leu Leu Gly Gly
            340                 345                 350

Pro Ser Val Phe Leu Phe Pro Pro Lys Pro Lys Asp Thr Leu Met Ile
        355                 360                 365

Ser Arg Thr Pro Glu Val Thr Cys Val Val Val Asp Val Ser His Glu
    370                 375                 380

Asp Pro Glu Val Lys Phe Asn Trp Tyr Val Asp Gly Val Glu Val His
385                 390                 395                 400

Asn Ala Lys Thr Lys Pro Arg Glu Glu Gln Tyr Asn Ser Thr Tyr Arg
                405                 410                 415

Val Val Ser Val Leu Thr Val Leu His Gln Asp Trp Leu Asn Gly Lys
            420                 425                 430

Glu Tyr Lys Cys Lys Val Ser Asn Lys Ala Leu Pro Ala Pro Ile Glu
        435                 440                 445

Lys Thr Ile Ser Lys Ala Lys Gly Gln Pro Arg Glu Pro Gln Val Tyr
    450                 455                 460

Thr Leu Pro Pro Cys Arg Glu Glu Met Thr Lys Asn Gln Val Ser Leu
```

```
465                 470                 475                 480

Trp Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Leu Tyr Ser Lys Leu Thr Val Asp
        515                 520                 525

Lys Ser Arg Trp Gln Gln Gly Asn Val Phe Ser Cys Ser Val Met His
    530                 535                 540

Glu Ala Leu His Asn His Tyr Thr Gln Lys Ser Leu Ser Leu Ser Pro
545                 550                 555                 560

Gly Gly Gly Gly Gly Ser Gly Gly Gly Gly Ser Thr Pro Val Ser Gln
                565                 570                 575

Thr Thr Thr Ala Ala Thr Ala Ser Val Arg Ser Thr Lys Asp Pro Cys
            580                 585                 590

Pro Ser Gln Pro Pro Val Phe Pro Ala Ala Lys Gln Cys Pro Ala Leu
        595                 600                 605

Glu Val Thr Trp Pro Glu Val Glu Val Pro Leu Asn Gly Thr Leu Ser
    610                 615                 620

Leu Ser Cys Val Ala Cys Ser Arg Phe Pro Asn Phe Ser Ile Leu Tyr
625                 630                 635                 640

Trp Leu Gly Asn Gly Ser Phe Ile Glu His Leu Pro Gly Arg Leu Trp
                645                 650                 655

Glu Gly Ser Thr Ser Arg Glu Arg Gly Ser Thr Gly Thr Gln Leu Cys
            660                 665                 670

Lys Ala Leu Val Leu Glu Gln Leu Thr Pro Ala Leu His Ser Thr Asn
        675                 680                 685

Phe Ser Cys Val Leu Val Asp Pro Glu Gln Val Val Gln Arg His Val
    690                 695                 700

Val Leu Ala Gln Leu Trp Ala Gly Leu Arg Ala Thr Leu Pro Pro Thr
705                 710                 715                 720

Gln Glu Ala Leu Pro Ser Ser His Ser Ser Pro Gln Gln Gln Gly
                725                 730                 735
```

```
<210> SEQ ID NO 14
<211> LENGTH: 831
<212> TYPE: PRT
<213> ORGANISM: Artificial Sequence
<220> FEATURE:
<223> OTHER INFORMATION: IL1R-kappa constant region-hinge region-CH2-
      CH3(S354C, T366W, K447A)-(G4S)4G-TGFbetaRII
<220> FEATURE:
<221> NAME/KEY: misc_feature
<223> OTHER INFORMATION: IL1R-kappa constant region-hinge region-CH2-
      CH3(S354C, T366W, K447A)-(G4S)4G-TGFbetaRII
<220> FEATURE:
<221> NAME/KEY: misc_feature
<222> LOCATION: (1)..(831)
<223> OTHER INFORMATION: IL1R-kappa constant region-hinge region-CH2-
      CH3(S354C, T366W, K447A)-(G4S)4G-TGFbetaRII

<400> SEQUENCE: 14

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45
```

```
Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Ser Gly Thr
                325                 330                 335

Val Ala Ala Pro Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
        355                 360                 365

Leu Asn Asn Phe Tyr Pro Arg Glu Ala Lys Val Gln Trp Lys Val Asp
    370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
            420                 425                 430

Gly Leu Ser Ser Pro Val Thr Lys Ser Phe Asn Arg Gly Glu Ser Asp
        435                 440                 445

Lys Thr His Thr Cys Pro Pro Cys Pro Ala Pro Glu Leu Leu Gly Gly
    450                 455                 460

Pro Ser Val Phe Leu Phe Pro Pro Lys Pro Lys Asp Thr Leu Met Ile
```

465 470 475 480

Ser Arg Thr Pro Glu Val Thr Cys Val Val Val Asp Val Ser His Glu
485 490 495

Asp Pro Glu Val Lys Phe Asn Trp Tyr Val Asp Gly Val Glu Val His
500 505 510

Asn Ala Lys Thr Lys Pro Arg Glu Glu Gln Tyr Asn Ser Thr Tyr Arg
515 520 525

Val Val Ser Val Leu Thr Val Leu His Gln Asp Trp Leu Asn Gly Lys
530 535 540

Glu Tyr Lys Cys Lys Val Ser Asn Lys Ala Leu Pro Ala Pro Ile Glu
545 550 555 560

Lys Thr Ile Ser Lys Ala Lys Gly Gln Pro Arg Glu Pro Gln Val Tyr
565 570 575

Thr Leu Pro Pro Cys Arg Glu Glu Met Thr Lys Asn Gln Val Ser Leu
580 585 590

Trp Cys Leu Val Lys Gly Phe Tyr Pro Ser Asp Ile Ala Val Glu Trp
595 600 605

Glu Ser Asn Gly Gln Pro Glu Asn Asn Tyr Lys Thr Thr Pro Pro Val
610 615 620

Leu Asp Ser Asp Gly Ser Phe Phe Leu Tyr Ser Lys Leu Thr Val Asp
625 630 635 640

Lys Ser Arg Trp Gln Gln Gly Asn Val Phe Ser Cys Ser Val Met His
645 650 655

Glu Ala Leu His Asn His Tyr Thr Gln Lys Ser Leu Ser Leu Ser Pro
660 665 670

Gly Ala Gly Gly Gly Gly Ser Gly Gly Gly Gly Ser Gly Gly Gly Gly
675 680 685

Ser Gly Gly Gly Gly Ser Gly Ile Pro Pro His Val Gln Lys Ser Val
690 695 700

Asn Asn Asp Met Ile Val Thr Asp Asn Asn Gly Ala Val Lys Phe Pro
705 710 715 720

Gln Leu Cys Lys Phe Cys Asp Val Arg Phe Ser Thr Cys Asp Asn Gln
725 730 735

Lys Ser Cys Met Ser Asn Cys Ser Ile Thr Ser Ile Cys Glu Lys Pro
740 745 750

Gln Glu Val Cys Val Ala Val Trp Arg Lys Asn Asp Glu Asn Ile Thr
755 760 765

Leu Glu Thr Val Cys His Asp Pro Lys Leu Pro Tyr His Asp Phe Ile
770 775 780

Leu Glu Asp Ala Ala Ser Pro Lys Cys Ile Met Lys Glu Lys Lys Lys
785 790 795 800

Pro Gly Glu Thr Phe Phe Met Cys Ser Cys Ser Ser Asp Glu Cys Asn
805 810 815

Asp Asn Ile Ile Phe Ser Glu Glu Tyr Asn Thr Ser Asn Pro Asp
820 825 830

<210> SEQ ID NO 15
<211> LENGTH: 853
<212> TYPE: PRT
<213> ORGANISM: Artificial Sequence
<220> FEATURE:
<223> OTHER INFORMATION: IL1RAcP-lambda constant region-hinge region-CH2-CH3(Y349C, T366S, L368A, Y407V, K447A)-(G4S)4G-TGFbetaRII
<220> FEATURE:
<221> NAME/KEY: misc_feature
<222> LOCATION: (1)..(853)
<223> OTHER INFORMATION: IL1RAcP-lambda constant region-hinge region-CH2-CH3(Y349C, T366S, L368A, Y407V, K447A)-(G4S)4G-TGFbetaRII

<400> SEQUENCE: 15

Met Thr Arg Leu Thr Val Leu Ala Leu Leu Ala Gly Leu Leu Ala Ser
1 5 10 15

Ser Arg Ala Ser Glu Arg Cys Asp Asp Trp Gly Leu Asp Thr Met Arg
20 25 30

Gln Ile Gln Val Phe Glu Asp Glu Pro Ala Arg Ile Lys Cys Pro Leu
35 40 45

Phe Glu His Phe Leu Lys Phe Asn Tyr Ser Thr Ala His Ser Ala Gly
50 55 60

Leu Thr Leu Ile Trp Tyr Trp Thr Arg Gln Asp Arg Asp Leu Glu Glu
65 70 75 80

Pro Ile Asn Phe Arg Leu Pro Glu Asn Arg Ile Ser Lys Glu Lys Asp
85 90 95

Val Leu Trp Phe Arg Pro Thr Leu Leu Asn Asp Thr Gly Asn Tyr Thr
100 105 110

Cys Met Leu Arg Asn Thr Thr Tyr Cys Ser Lys Val Ala Phe Pro Leu
115 120 125

Glu Val Val Gln Lys Asp Ser Cys Phe Asn Ser Pro Met Lys Leu Pro
130 135 140

Val His Lys Leu Tyr Ile Glu Tyr Gly Ile Gln Arg Ile Thr Cys Pro
145 150 155 160

Asn Val Asp Gly Tyr Phe Pro Ser Ser Val Lys Pro Thr Ile Thr Trp
165 170 175

Tyr Met Gly Cys Tyr Lys Ile Gln Asn Phe Asn Asn Val Ile Pro Glu
180 185 190

Gly Met Asn Leu Ser Phe Leu Ile Ala Leu Ile Ser Asn Asn Gly Asn
195 200 205

Tyr Thr Cys Val Val Thr Tyr Pro Glu Asn Gly Arg Thr Phe His Leu
210 215 220

Thr Arg Thr Leu Thr Val Lys Val Val Gly Ser Pro Lys Asn Ala Val
225 230 235 240

Pro Pro Val Ile His Ser Pro Asn Asp His Val Val Tyr Glu Lys Glu
245 250 255

Pro Gly Glu Glu Leu Leu Ile Pro Cys Thr Val Tyr Phe Ser Phe Leu
260 265 270

Met Asp Ser Arg Asn Glu Val Trp Trp Thr Ile Asp Gly Lys Lys Pro
275 280 285

Asp Asp Ile Thr Ile Asp Val Thr Ile Asn Glu Ser Ile Ser His Ser
290 295 300

Arg Thr Glu Asp Glu Thr Arg Thr Gln Ile Leu Ser Ile Lys Lys Val
305 310 315 320

Thr Ser Glu Asp Leu Lys Arg Ser Tyr Val Cys His Ala Arg Ser Ala
325 330 335

Lys Gly Glu Val Ala Lys Ala Ala Lys Val Lys Gln Lys Val Pro Ala
340 345 350

Pro Arg Tyr Thr Val Glu Gln Pro Lys Ala Ala Pro Gly Gln Pro Lys
355 360 365

Ala Ala Pro Ser Val Thr Leu Phe Pro Pro Ser Ser Glu Glu Leu Gln
370 375 380

```
Ala Asn Lys Ala Thr Leu Val Cys Leu Ile Ser Asp Phe Tyr Pro Gly
385                 390                 395                 400

Ala Val Thr Val Ala Trp Lys Ala Asp Ser Ser Pro Val Lys Ala Gly
                405                 410                 415

Val Glu Thr Thr Thr Pro Ser Lys Gln Ser Asn Asn Lys Tyr Ala Ala
            420                 425                 430

Ser Ser Tyr Leu Ser Leu Thr Pro Glu Gln Trp Lys Ser His Arg Ser
        435                 440                 445

Tyr Ser Cys Gln Val Thr His Glu Gly Ser Thr Val Glu Lys Thr Val
    450                 455                 460

Ala Pro Thr Glu Ser Asp Lys Thr His Thr Cys Pro Pro Cys Pro Ala
465                 470                 475                 480

Pro Glu Leu Leu Gly Gly Pro Ser Val Phe Leu Phe Pro Pro Lys Pro
                485                 490                 495

Lys Asp Thr Leu Met Ile Ser Arg Thr Pro Glu Val Thr Cys Val Val
            500                 505                 510

Val Asp Val Ser His Glu Asp Pro Glu Val Lys Phe Asn Trp Tyr Val
        515                 520                 525

Asp Gly Val Glu Val His Asn Ala Lys Thr Lys Pro Arg Glu Glu Gln
    530                 535                 540

Tyr Asn Ser Thr Tyr Arg Val Val Ser Val Leu Thr Val Leu His Gln
545                 550                 555                 560

Asp Trp Leu Asn Gly Lys Glu Tyr Lys Cys Lys Val Ser Asn Lys Ala
                565                 570                 575

Leu Pro Ala Pro Ile Glu Lys Thr Ile Ser Lys Ala Lys Gly Gln Pro
            580                 585                 590

Arg Glu Pro Gln Val Cys Thr Leu Pro Pro Ser Arg Glu Glu Met Thr
        595                 600                 605

Lys Asn Gln Val Ser Leu Ser Cys Ala Val Lys Gly Phe Tyr Pro Ser
    610                 615                 620

Asp Ile Ala Val Glu Trp Glu Ser Asn Gly Gln Pro Glu Asn Asn Tyr
625                 630                 635                 640

Lys Thr Thr Pro Pro Val Leu Asp Ser Asp Gly Ser Phe Phe Leu Val
                645                 650                 655

Ser Lys Leu Thr Val Asp Lys Ser Arg Trp Gln Gln Gly Asn Val Phe
            660                 665                 670

Ser Cys Ser Val Met His Glu Ala Leu His Asn His Tyr Thr Gln Lys
        675                 680                 685

Ser Leu Ser Leu Ser Pro Gly Ala Gly Gly Gly Gly Ser Gly Gly Gly
    690                 695                 700

Gly Ser Gly Gly Gly Gly Ser Gly Gly Gly Gly Ser Gly Ile Pro Pro
705                 710                 715                 720

His Val Gln Lys Ser Val Asn Asn Asp Met Ile Val Thr Asp Asn Asn
                725                 730                 735

Gly Ala Val Lys Phe Pro Gln Leu Cys Lys Phe Cys Asp Val Arg Phe
            740                 745                 750

Ser Thr Cys Asp Asn Gln Lys Ser Cys Met Ser Asn Cys Ser Ile Thr
        755                 760                 765

Ser Ile Cys Glu Lys Pro Gln Glu Val Cys Val Ala Val Trp Arg Lys
    770                 775                 780

Asn Asp Glu Asn Ile Thr Leu Glu Thr Val Cys His Asp Pro Lys Leu
785                 790                 795                 800

Pro Tyr His Asp Phe Ile Leu Glu Asp Ala Ala Ser Pro Lys Cys Ile
```

```
                805                 810                 815

Met Lys Glu Lys Lys Lys Pro Gly Glu Thr Phe Phe Met Cys Ser Cys
            820                 825                 830

Ser Ser Asp Glu Cys Asn Asp Asn Ile Ile Phe Ser Glu Glu Tyr Asn
        835                 840                 845

Thr Ser Asn Pro Asp
    850


<210> SEQ ID NO 16
<211> LENGTH: 5
<212> TYPE: PRT
<213> ORGANISM: Artificial Sequence
<220> FEATURE:
<223> OTHER INFORMATION: This sequence is repeated 'n' times.
<220> FEATURE:
<221> NAME/KEY: misc_feature
<222> LOCATION: (1)..(5)
<223> OTHER INFORMATION: This sequence is repeated 'n' times.

<400> SEQUENCE: 16

Gly Ser Gly Ser Gly
1               5


<210> SEQ ID NO 17
<211> LENGTH: 5
<212> TYPE: PRT
<213> ORGANISM: Artificial Sequence
<220> FEATURE:
<223> OTHER INFORMATION: a linker

<400> SEQUENCE: 17

Gly Gly Ser Ser Gly
1               5


<210> SEQ ID NO 18
<211> LENGTH: 4
<212> TYPE: PRT
<213> ORGANISM: Artificial Sequence
<220> FEATURE:
<223> OTHER INFORMATION: a linker
<220> FEATURE:
<221> NAME/KEY: misc_feature
<222> LOCATION: (1)..(4)
<223> OTHER INFORMATION: This sequence is repeated 'n' times.

<400> SEQUENCE: 18

Gly Gly Ser Gly
1


<210> SEQ ID NO 19
<211> LENGTH: 4
<212> TYPE: PRT
<213> ORGANISM: Artificial Sequence
<220> FEATURE:
<223> OTHER INFORMATION: a linker
<220> FEATURE:
<221> NAME/KEY: misc_feature
<222> LOCATION: (1)..(4)
<223> OTHER INFORMATION: This sequence is repeated 'n' times.

<400> SEQUENCE: 19

Gly Gly Gly Ser
1


<210> SEQ ID NO 20
<211> LENGTH: 5
<212> TYPE: PRT
```

-continued

```
<213> ORGANISM: Artificial Sequence
<220> FEATURE:
<223> OTHER INFORMATION: a linker
<220> FEATURE:
<221> NAME/KEY: misc_feature
<222> LOCATION: (1)..(5)
<223> OTHER INFORMATION: This sequence is repeated 'n' times.

<400> SEQUENCE: 20

Gly Gly Gly Gly Ser
1               5


<210> SEQ ID NO 21
<211> LENGTH: 6
<212> TYPE: PRT
<213> ORGANISM: Artificial Sequence
<220> FEATURE:
<223> OTHER INFORMATION: a linker
<220> FEATURE:
<221> NAME/KEY: REPEAT
<222> LOCATION: (1)..(5)
<223> OTHER INFORMATION: This sequence is repeated 'n' times.
<220> FEATURE:
<221> NAME/KEY: REPEAT
<222> LOCATION: (6)..(6)
<223> OTHER INFORMATION: This sequence is repeated 'n' times.

<400> SEQUENCE: 21

Gly Gly Ser Gly Gly Gly
1               5


<210> SEQ ID NO 22
<211> LENGTH: 13
<212> TYPE: PRT
<213> ORGANISM: Artificial Sequence
<220> FEATURE:
<223> OTHER INFORMATION: a linker

<400> SEQUENCE: 22

Gly Ser Gly Gly Gly Gly Ser Gly Gly Gly Gly Ser Gly
1               5                   10


<210> SEQ ID NO 23
<211> LENGTH: 10
<212> TYPE: PRT
<213> ORGANISM: Artificial Sequence
<220> FEATURE:
<223> OTHER INFORMATION: a linker

<400> SEQUENCE: 23

Gly Gly Gly Gly Ser Gly Gly Gly Gly Ser
1               5                   10
```